US011839652B2

United States Patent
Gomis et al.

(12) United States Patent
(10) Patent No.: US 11,839,652 B2
(45) Date of Patent: Dec. 12, 2023

(54) METHODS AND COMPOSITIONS FOR INDUCING PROTECTIVE IMMUNITY

(71) Applicant: University of Saskatchewan, Saskatoon (CA)

(72) Inventors: Susantha Gomis, Saskatoon (CA); Shelly Popowich, Saskatoon (CA); Kalhari Venukala Bandara Goonewardene, Saskatoon (CA); Suresh Tikoo, Saskatoon (CA); Marianna Foldvari, Waterloo (CA)

(73) Assignee: University of Saskatchewan, Saskatoon (SK)

( * ) Notice: Subject to any disclaimer, the term of this patent is extended or adjusted under 35 U.S.C. 154(b) by 178 days.

(21) Appl. No.: 16/630,744

(22) PCT Filed: Jul. 17, 2018

(86) PCT No.: PCT/CA2018/050866
§ 371 (c)(1),
(2) Date: Jan. 13, 2020

(87) PCT Pub. No.: WO2019/014761
PCT Pub. Date: Jan. 24, 2019

(65) Prior Publication Data
US 2020/0164066 A1 May 28, 2020

Related U.S. Application Data

(60) Provisional application No. 62/533,373, filed on Jul. 17, 2017.

(51) Int. Cl.
*A61K 39/39* (2006.01)
*A23K 20/153* (2016.01)
(Continued)

(52) U.S. Cl.
CPC ............ *A61K 39/39* (2013.01); *A23K 20/153* (2016.05); *A23K 50/75* (2016.05); *C12N 15/117* (2013.01);
(Continued)

(58) Field of Classification Search
None
See application file for complete search history.

(56) References Cited

U.S. PATENT DOCUMENTS

2003/0087848 A1* 5/2003 Bratzler ............... A61K 31/557 514/44 A
2008/0112915 A1* 5/2008 Foldvari ............ A61K 48/0033 424/78.02
2019/0070313 A1 3/2019 Rafiee

FOREIGN PATENT DOCUMENTS

CA 3009829 A1 3/2019
EP 1985702 A2 10/2008
(Continued)

OTHER PUBLICATIONS

Rankin R, Pontarollo R, Ioannou X, Krieg AM, Hecker R, Babiuk LA, van Drunen Littel-van den Hurk S. CpG motif identification for veterinary and laboratory species demonstrates that sequence recognition is highly conserved. Antisense Nucleic Acid Drug Dev. Oct. 2001;11(5):333-40. (Year: 2001).*
(Continued)

*Primary Examiner* — Michelle S Horning
(74) *Attorney, Agent, or Firm* — Bereskin & Parr LLP; Carmela De Luca

(57) ABSTRACT

This application relates to compositions comprising one or more CpG oligodeoxynucleotides complexed to nanoparticles comprising a gemini surfactant and optionally a mucoadhesive polymer, which can be used for intrapulmonary
(Continued)

delivery to induce immunity in feed animals, and the methods of making and uses thereof.

20 Claims, 13 Drawing Sheets

Specification includes a Sequence Listing.

(51) Int. Cl.

| | |
|---|---|
| ***A23K 50/75*** | (2016.01) |
| ***C12N 15/117*** | (2010.01) |
| ***A61K 47/69*** | (2017.01) |
| ***A61K 47/58*** | (2017.01) |
| ***A61K 47/61*** | (2017.01) |
| ***A61K 9/00*** | (2006.01) |
| ***A61K 47/10*** | (2017.01) |
| ***A61K 47/18*** | (2017.01) |
| ***A61K 47/24*** | (2006.01) |
| ***A61K 39/00*** | (2006.01) |

(52) U.S. Cl.

CPC ............ *A61K 9/0078* (2013.01); *A61K 47/10* (2013.01); *A61K 47/183* (2013.01); *A61K 47/24* (2013.01); *A61K 47/58* (2017.08); *A61K 47/61* (2017.08); *A61K 47/6911* (2017.08); *A61K 47/6929* (2017.08); *A61K 2039/544* (2013.01); *A61K 2039/552* (2013.01); *A61K 2039/58* (2013.01); *A61K 2039/6093* (2013.01); *C12N 2310/17* (2013.01); *C12N 2310/315* (2013.01); *C12N 2320/32* (2013.01)

(56) References Cited

FOREIGN PATENT DOCUMENTS

| | | | |
|---|---|---|---|
| WO | 2003/030656 | A2 | 4/2003 |
| WO | 2005/039642 | A1 | 5/2005 |
| WO | 2006/136460 | A2 | 12/2006 |
| WO | 2014/134698 | A1 | 9/2014 |

OTHER PUBLICATIONS

Moingeon P. Adjuvants for allergy vaccines. Hum Vaccin Immunother. Oct. 2012;8(10):1492-8. doi: 10.4161/hv.21688. Epub Oct. 1, 2012. PMID: 23095872; PMCID: PMC3660771. (Year: 2012).*

Kadajji, V.G.; Betageri, G.V. Water Soluble Polymers for Pharmaceutical Applications. Polymers 2011, 3, 1972-2009. https://doi.org/10.3390/polym3041972 (Year: 2011).*

A.K. Panda, Nanotechnology in vaccine development, Proceedings of the National Academy of Sciences, India Section B: Biological Sciences, 82 (2012) 13-27.

M.-G. Kim, J.Y. Park, Y. Shon, G. Kim, G. Shim, Y.-K. Oh, Nanotechnology and vaccine development, Asian Journal of Pharmaceutical Sciences, 9 (2014) 227-235.

A. Nasir, Nanotechnology in vaccine development: a step forward, Journal of Investigative Dermatology, 129 (2009) 1055-1059.

H. Shirota, D.M. Klinman, Recent progress concerning CpG DNA and its use as a vaccine adjuvant, Expert review of vaccines, 13 (2014) 299-312.

T. Negash, M. Liman, S. Rautenschlein, Mucosal application of cationic poly(D,L-lactide-co-glycolide) microparticles as carriers of DNA vaccine and adjuvants to protect chickens against infectious bursal disease, Vaccine, 31 (2013) 3656-3662.

M. Günbeyaz, A. Faraji, A. Özkul, N. Purall, S. Şenel, Chitosan based delivery systems for mucosal immunization against bovine herpesvirus 1 (BHV-1), European Journal of Pharmaceutical Sciences, 41 (2010) 531-545.

E.N.T. Meeusen, J. Walker, A. Peters, P.-P. Pastoret, G. Jungersen, Current status of veterinary vaccines, Clinical Microbiology Reviews, 20 (2007) 489-510.

C.-J. Chiou, L.-P. Tseng, M.-C. Deng, P.-R. Jiang, S.-L. Tasi, T.-W. Chung, Y.-Y. Huang, D.-Z. Liu, Mucoadhesive liposomes for intranasal immunization with an avian influenza virus vaccine in chickens, Biomaterials, 30 (2009) 5862-5868.

M.A. Volkova, A.V. Irza, I.A. Chvala, S.F. Frolov, V.V. Drygin, D.R. Kapczynski, Adjuvant effects of chitosan and calcium phosphate particles in an inactivated Newcastle disease vaccine, Avian diseases, 58 (2014) 46-52.

L.-P. Tseng, C.-J. Chiou, C.-C. Chen, M.-C. Deng, T.-W. Chung, Y.-Y. Huang, D.-Z. Liu, Effect of lipopolysaccharide on intranasal administration of liposomal Newcastle disease virus vaccine to SPF chickens, Veterinary Immunology and Immunopathology, 131 (2009) 285-289.

K. Yaguchi, T. Ohgitani, T. Noro, T. Kaneshige, Y. Shimizu, Vaccination of chickens with liposomal inactivated avian pathogenic *Escherichia coli* (APEC) vaccine by eye drop or coarse spray administration, Avian diseases, 53 (2009) 245-249.

A. Taghavi, B. Allan, G. Mutwiri, A. Van Kessel, P. Willson, L. Babiuk, A. Potter, S. Gomis, Protection of neonatal broiler chicks against *Salmonella typhimurium* septicemia by DNA containing CpG motifs, Avian diseases, 52 (2008) 398-406.

K.M. Mackinnon, H. He, C.L. Swaggerty, J.L. McReynolds, K.J. Genovese, S.E. Duke, J.R. Nerren, M.H. Kogut, In ovo treatment with CpG oligodeoxynucleotides decreases colonization of *Salmonella enteriditis* in broiler chickens, Veterinary Immunology and Immunopathology, 127 (2009) 371-375.

S. Gomis, L. Babiuk, D.L. Godson, B. Allan, T. Thrush, H. Townsend, P. Willson, E. Waters, R. Hecker, A. Potter, Protection of chickens against *Escherichia coli* infections by DNA containing CpG motifs, Infection and Immunity, 71 (2003) 857-863.

R.B. Hayter, E.L. Besch, Airborne-particle deposition in the respiratory tract of chickens, Poultry science, 53 (1974) 1507-1511.

E.A. Corbanie, M.G. Matthijs, J.H. van Eck, J.P. Remon, W.J. Landman, C. Vervaet, Deposition of differently sized airborne microspheres in the respiratory tract of chickens, Avian Pathol, 35 (2006) 475-485.

M. Look, A. Bandyopadhyay, J.S. Blum, T.M. Fahmy, Application of nanotechnologies for improved immune response against infectious diseases in the developing world, Advanced Drug Delivery Reviews, 62 (2010) 378-393.

H.-Q. Mao, K. Roy, V.L. Troung-Le, K.A. Janes, K.Y. Lin, Y. Wang, J.T. August, K.W. Leong, Chitosan-DNA nanoparticles as gene carriers: synthesis, characterization and transfection efficiency, Journal of Controlled Release, 70 (2001) 399-421.

T. Sato, T. Ishii, Y. Okahata, In vitro gene delivery mediated by chitosan. effect of pH, serum, and molecular mass of chitosan on the transfection efficiency, Biomaterials, 22 (2001) 2075-2080.

P. Erbacher, S. Zou, T. Bettinger, A.M. Steffan, J.S. Remy, Chitosan-based vector/DNA complexes for gene delivery: biophysical characteristics and transfection ability, Pharmaceutical Research, 15 (1998) 1332-1339.

M. Huang, E. Khor, L.-Y. Lim, Uptake and cytotoxicity of chitosan molecules and nanoparticles: effects of molecular weight and degree of deacetylation, Pharmaceutical Research, 21 (2004) 344-353.

S. Mao, W. Sun, T. Kissel, Chitosan-based formulations for delivery of DNA and siRNA, Advanced Drug Delivery Reviews, 62 (2010) 12-27.

M. Koping-Hoggard, I. Tubulekas, H. Guan, K. Edwards, M. Nilsson, K.M. Varum, P. Artursson, Chitosan as a nonviral gene delivery system. Structure-property relationships and characteristics compared with polyethylenimine in vitro and after lung administration in vivo, The Journal of Gene Therapy, 8 (2001) 1108-1121.

Daniella Calderon-Nieva et al. Veterinary vaccine nanotechnology: pulmonary and nasal delivery in livestock animals. Drug Deliv. and Transl. Res. (2017) 7:558-570.

Goonewardene, Kalhari Bandara et al. Intrapulmonary Delivery of CpG-ODN Microdroplets Provides Protection Against *Escherichia coli* septicemia in Neonatal Broiler Chickens. Avian Diseases, 61(4):503-511, 2017.

(56) References Cited

OTHER PUBLICATIONS

Goonewardene, Kalhari Bandara et al. Mucosal delivery of CpG-ODN mimicking bacterial DNA via the intrapulmonary route induces systemic antimicrobial immune responses in neonatal chicks. Scientific Reports, 10:5343, 2020.
Gunawardana, T. et al. "Protection of Neonatal Broiler Chickens Following in ovo Delivery of Oligodeoxynucleotides Containing CpG Motifs (CpG-ODN) Formulated with Carbon Nanotubes or Liposomes." Avian Disease, 59:31-37, Dec. 2014.
Goonewardene, Kalhari Bandara er al. "Intrapulmonary Delivery of CpG-ODN microdroplets provides protection against *Escherichia coli* septicemia in neonatal broiler chickens". Avian Diseases, Oct. 20, 2017 (Sep. 20, 2017), vol. 61, pp. 503-511.
Calderon-Nieva, D. et al. "Veterinary vaccine nanotechnology: pulmonary and nasal delivery in livestock animals." Drug Deliv. and Transl. Res. Jun. 21, 2017. DOI 10.1007/s13346-017-0400-9.
Calderon-Nieva, D. et al. "Improving the delivery and immunogenicity of an inhalable CpG-ODN DNA vaccine by bio-adhesive gemini nanoparticles in neonatal chickens." UWSPACE Waterloo's Institutional Repository. Jan. 5, 2018.
Calderon-Nieva, D. et al. "Pulmonary nanoparticle vaccines as antimicrobial alternatives for poultry." Controlled Release Society Annual Meeting & Exposition, Boston Jul. 16-19, 2017. Abstact only.
Badea, I. et al. "Gemini nanoparticles as a co-delivery system for antigen—CpG oligodeoxynucleotide adjuvant combination." Int. J. Biomedical Nanoscience and Nanotechnology, vol. 1, Nos. 2/3/4, 2010, 290-307.
Wierup, M. The control of microbial diseases in animals: alternatives to the use of antibiotics. Int J Antimicrob Ag 14:315-319. 2000.
Yassin, H., A. G. J. Velthuis, M. Boerjan, and J. van Riel. Field study on broilers' first-week mortality. Poultry Sci 88:798-804. 2009.
Brigden, J. L., and C. Riddell. A survey of mortality in four broiler flocks in western Canada. The Canadian veterinary journal. La revue veterinaire canadienne 16:194-200. 1975.
Casewell, M., C. Friis, E. Marco, P. McMullin, and I. Phillips. The European ban on growth-promoting antibiotics and emerging consequences for human and animal health. J Antimicrob Chemoth 52:159-161. 2003.
Gyles, C. L. Antimicrobial resistance in selected bacteria from poultry. Animal Health Research Reviews 9:149-158. 2008.
Allen, H. K., U. Y. Levine, T. Looft, M. Bandrick, and T. A. Casey. Treatment, promotion, commotion: antibiotic alternatives in food-producing animals. Trends Microbiol 21:114-119. 2013.
Millet, S., and L. Maertens. The European ban on antibiotic growth promoters in animal feed: From challenges to opportunities. The Veterinary Journal 187:143-144. 2011.
Krieg, A. M., A. K. Yi, S. Matson, T. J. Waldschmidt, G. A. Bishop, R. Teasdale, G. A. Koretzky, and D. M. Klinman. CpG motifs in bacterial DNA trigger direct B-cell activation. Nature 374:546-549. 1995.
Neujahr, D. C., C. F. Reich, and D. S. Pisetsky. Immunostimulatory properties of genomic DNA from different bacterial species. Immunobiology 200:106-119. 1999.
Yamamoto, S., T. Yamamoto, T. Kataoka, E. Kuramoto, O. Yano, and T. Tokunaga. Unique Palindromic Sequences in Synthetic Oligonucleotides Are Required to Induce Inf and Augment Inf-Mediated Natural-Killer Activity. J Immunol 148:4072-4076. 1992.
Yamamoto, S., T. Yamamoto, S. Shimada, E. Kuramoto, O. Yano, T. Kataoka, and T. Tokunaga. DNA from Bacteria, but Not from Vertebrates, Induces Interferons, Activates Natural-Killer-Cells and Inhibits Tumor-Growth. Microbiol Immunol 36:983-997. 1992.
Ahmad-Nejad, P., H. Hacker, M. Rutz, S. Bauer, R. M. Vabulas, and H. Wagner. Bacterial CpG-DNA and lipopolysaccharides activate Toll-like receptors at distinct cellular compartments. European journal of immunology 32:1958-1968. 2002.
Hemmi, H., O. Takeuchi, T. Kawai, T. Kaisho, S. Sato, H. Sanjo, M. Matsumoto, K. Hoshino, H. Wagner, K. Takeda, and S. Akira. A Toll-like receptor recognizes bacterial DNA. Nature 408:740-745. 2000.
Sparwasser, T., E. S. Koch, R. M. Vabulas, K. Heeg, G. B. Lipford, J. W. Ellwart, and H. Wagner. Bacterial DNA and immunostimulatory CpG oligonucleotides trigger maturation and activation of murine dendritic cells. European journal of immunology 28:2045-2054. 1998.
Klinman, D. M., A. K. Yi, S. L. Beaucage, J. Conover, and A. M. Krieg. CpG motifs present in bacterial DNA rapidly induce lymphocytes to secrete interleukin 6, interleukin 12, and interferon gamma. P Natl Acad Sci USA 93:2879-2883. 1996.
Krieg, A. M., L. Love-Homan, A. K. Yi, and J. T. Harty. CpG DNA induces sustained IL-12 expression in vivo and resistance to Listeria monocytogenes challenge. J Immunol 161:2428-2434. 1998.
Ray, N. B., and A. M. Krieg. Oral pretreatment of mice with CpG DNA reduces susceptibility to oral or intraperitoneal challenge with virulent Listetia monocytogenes. Infection and immunity 71:4398-4404. 2003.
Lewis, E. J., S. Agrawal, J. Bishop, J. Chadwick, N. D. Cristensen, S. Cuthill, P. Dunford, A. K. Field, J. Francis, V. Gibson, A. K. Greenham, F. Kelly, R. Kilkushie, J. W. Kreider, J. S. Mills, M. Mulqueen, N. A. Roberts, P. Roberts, and D. E. Szymkowski. Non-specific antiviral activity of antisense molecules targeted to the E1 region of human papillomavirus. Antivir Res 48:187-196. 2000.
Zimmermann, S., O. Egeter, S. Hausmann, G. B. Lipford, M. Rocken, H. Wagner, and K. Heeg. Cutting edge: CpG oligodeoxynucleotides trigger protective and curative Th1 responses in lethal murine leishmaniasis. J Immunol 160:3627-3630. 1998.
Brownlie, R., J. Z. Zhu, B. Allan, G. K. Mutwiri, L. A. Babiuk, A. Potter, and P. Griebel. Chicken TLR21 acts as a functional homologue to mammalian TLR9 in the recognition of CpG oligodeoxynucleotides. Molecular immunology 46:3163-3170. 2009.
Keestra, A. M., M. R. de Zoete, L. I. Bouwman, and J. P. M. van Putten. Chicken TLR21 Is an Innate CpG DNA Receptor Distinct from Mammalian TLR9. J Immunol 185:460-467. 2010.
Patel, B. A., S. Gomis, A. Dar, P. J. Willson, L. A. Babiuk, A. Potter, G. Mutwiri, and S. K. Tikoo. Oligodeoxynucleotides containing CpG motifs (CpG-ODN) predominantly induce Th1-type immune response in neonatal chicks. Dev Comp Immunol 32:1041-1049. 2008.
Gomis, S., L. Babiuk, B. Allan, P. Willson, E. Waters, N. Ambrose, R. Hecker, and A. Potter. Protection of neonatal chicks against a lethal challenge of *Escherichia coli* using DNA containing cytosine-phosphodiester-guanine motifs. Avian diseases 48:813-822. 2004.
Taghavi, A., B. Allan, G. Mutwiri, A. Van Kessel, P. Willson, L. Babiuk, A. Potter, and S. Gomis. Protection of neonatal broiler chicks against *Salmonella typhimurium* septicemia by DNA containing CpG motifs. Avian diseases 52:398-406. 2008.
T. Gunawardana, M. Foldvari, T. Zachar, S. Popowich, B. Chow-Lockerbie, M.V. Ivanova, S. Tikoo, S. Kurukulasuriya, P. Willson, S. Gomis, Protection of neonatal broiler chickens following in ovo delivery of oligodeoxynucleotides containing CpG motifs (CpG-ODN) formulated with carbon nanotubes or liposomes, Avian diseases, 59 (2015) 31-37.
S. Gomis, L. Babiuk, B. Allan, P. Willson, E. Waters, N. Ambrose, R. Hecker, A. Potter, Protection of neonatal chicks against a lethal challenge of *Escherichia coli* using DNA containing cytosine-phosphodiester-guanine motifs, Avian diseases, 48 (2004) 813-822.
J.T. van Oirschot, Present and future of veterinary viral vaccinology: a review, The Veterinary quarterly, 23 (2001) 100-108.
M.B. Dolovich, R. Dhand, Aerosol drug delivery: developments in device design and clinical use, 2011 The Lancet, 377 1032-1045.
A. Gautam, J. Clifford Waldrep, C.L. Densmore, Aerosol gene therapy, Molecular Biotechnology, 23 (2003) 51-60.
G.d. Lange, Spray vaccination of day-old-chicks at the hatchery, in, Pas Reform Integrated hatchery solutions, Pas Reform Integrated hatchery solutions (2014).
B. Peeters, W.F. Tonnis, S. Murugappan, P. Rottier, G. Koch, H.W. Frijlink, A. Huckriede, W.L.J. Hinrichs, Pulmonary immunization of chickens using non-adjuvanted spray-freeze dried whole inactivated virus vaccine completely protects against highly pathogenic H5N1 avian influenza virus, Vaccine, 32 (2014) 6445-6450.

(56) References Cited

OTHER PUBLICATIONS

F. Andrade, D. Rafael, M. Videira, D. Ferreira, A. Sosnik, B. Sarmento, Nanotechnology and pulmonary delivery to overcome resistance in infectious diseases, Advanced Drug Delivery Reviews, 65 (2013) 1816-1827.
M.D.I. Manunta, R.J. McAnulty, A. McDowell, J. Jin, D. Ridout, J. Fleming, S.E -. Bottoms, L. Tossici-Bolt, G.J. Laurent, L. Biassoni, C. O'Callaghan, S.L. Hart, Airway deposition of nebulized gene delivery nanocomplexes monitored by radioimaging agents, American Journal of Respiratory Cell and Molecular Biology, 49 (2013) 471-480.
J. McCaskill, R. Singhania, M. Burgess, R. Allavena, S. Wu, A. Blumenthal, N.A.J. McMillan, Efficient biodistribution and gene silencing in the lung epithelium via intravenous liposomal delivery of siRNA, Molecular Therapy Nucleic Acids, 2 (2013) e96.
G. Shim, H.-w. Choi, S. Lee, J. Choi, Y.H. Yu, D.-E. Park, Y. Choi, C.-W. Kim, Y.-K. Oh, Enhanced Intrapulmonary Delivery of Anticancer siRNA for Lung Cancer Therapy Using Cationic Ethylphosphocholine-based Nanolipoplexes, Molecular Therapy, 21 (2013) 816-824.
C. Sawaengsak, Y. Mori, K. Yamanishi, P. Srimanote, W. Chaicumpa, A. Mitrevej, N. Sinchaipanid, Intranasal chitosan-DNA vaccines that protect across influenza virus subtypes, International Journal of Pharmaceutics, 473 (2014) 113-125.
J.S. Suk, A.J. Kim, K. Trehan, C.S. Schneider, L. Cebotaru, O.M. Woodward, N.J. Boylan, M.P. Boyle, S.K. Lai, W.B. Guggino, J. Hanes, Lung gene therapy with highly compacted DNA nanoparticles that overcome the mucus barrier, Journal of Controlled Release, 178 (2014) 8-17.
M. Bivas-Benita, K.E. van Meijgaarden, K.L.M.C. Franken, H.E. Junginger, G. Borchard, T.H.M. Ottenhoff, A. Geluk, Pulmonary delivery of chitosan-DNA nanoparticles enhances the immunogenicity of a DNA vaccine encoding HLA-A*0201-restricted T-cell epitopes of *Mycobacterium tuberculosis*, Vaccine, 22 (2004) 1609-1615.
J.F.S. Mann, P.F. McKay, S. Arokiasamy, R.K. Patel, K. Klein, R.J. Shattock, Pulmonary delivery of DNA vaccine constructs using deacylated PEI elicits immune responses and protects against viral challenge infection, Journal of Controlled Release, 170 (2013) 452-459.
V. Weissig, T.K. Pettinger, N. Murdock, Nanopharmaceuticals (part 1): products on the market, International Journal of Nanomedicine, 9 (2014) 4357-4373.
V. Gerdts, G.K. Mutwiri, S.K. Tikoo, L.A. Babiuk, Mucosal delivery of vaccines in domestic animals, Veterinary research, 37 (2006) 487-510.
A. Taghavi, B. Allan, G. Mutwiri, M. Foldvari, A. Van Kessel, P. Willson, L. Babiuk, A. Potter, S. Gomis, Enhancement of immunoprotective effect of CpG-ODN by formulation with polyphosphazenes against *E. coli* septicemia in neonatal chickens, Current drug delivery, 6 (2009) 76-82.
F. Mansoor, B. Earley, J.P. Cassidy, B. Markey, S. Doherty, M.D. Welsh, Comparing the immune response to a novel intranasal nanoparticle PLGA vaccine and a commercial BPI3V vaccine in dairy calves, BMC Veterinary Research, 11 (2015) 220.
Goonwardene, Kalhari Bandara et al. "Intrapulmonary Delivery of CpG-Odn Microdroplets Provides Protection Against *Escherichia coli* Septicemia in Neonatal Broiler Chickens", Avian Disease 61:503-511, 2017.

* cited by examiner

METHODS AND COMPOSITIONS FOR INDUCING PROTECTIVE IMMUNITY

RELATED APPLICATIONS

This is a PCT application, which claims the benefit of 35 U.S.C. 119 based on the priority of Provisional Patent Application No. 62/533,373 filed Jul. 17, 2017, herein incorporated by reference in its entirety.

SEQUENCE LISTING

A computer readable form of the Sequence Listing "SequenceListing_ST25.txt" (2760 bytes), created on Jul. 17, 2018, is herein incorporated by reference.

The present application relates to compositions for inducing immunity in feed animals, including neonates, using immunostimulatory nucleic acids such as CpG-ODN through intrapulmonary delivery, and uses thereof.

INTRODUCTION

The commercial poultry industry is constantly searching for novel measures to combat infections to ensure the welfare of birds and food safety (1). High mortality associated with bacterial infections during the neonatal stage of a bird's life has devastating impacts on production (2). For example, *Escherichia coli* septicemia is a major cause of first-week mortality in the broiler chicken industry worldwide (3). In addition to high mortality during the flock cycle, these bacterial infections result in a lack of uniformity of a flock, chronic infections and condemnation of carcasses at processing (3, 4). To prevent losses due to bacterial infections in the poultry industry, prophylactic use of antibiotics is in common practice in some areas of the poultry industry. These industry practices risk emergence of resistant strains of bacteria and antibiotic residues in poultry products (5, 6). Given the global concern for antimicrobial resistance, the CDC, FDA, and WHO have announced the importance of regulating and controlling resistance (27). Because of this, in 2014, the Canadian poultry industry eliminated preventative use of category I antibiotics, those most vital to human health, in chickens. They are further working to eliminate category II and III antibiotics.

Given the elimination of these antibiotics, there is a major concern for *Escherichia coli* (*E. coli*) infection in broiler chicks. This is a common infection which plagues the modern broiler chick industry resulting in rapid loss of chicks and massive economic losses (28). In order to prevent diseases in broilers that are primarily treated and controlled with antibiotics, alternative options must be implemented to promote the health and growth of the modern broiler chicken (7, 8).

Vaccination is among the strongest infectious disease prevention strategies in humans. Similarly, broiler chickens and layer hens in the poultry industry are subject to intensive vaccination procedures that protect them against many infectious diseases (29). In order to combat *E. coli* infection in chickens especially chicks, an alternative includes the implementation of large scale immunization with CpG-ODN DNA within poultry farms. Vaccination of neonatal broiler chicks with a DNA sequence adjuvant such as CpG-ODN has been shown to stimulate the avian immune response and protect against pathological events associated with bacterial infection (28).

Earlier studies have reported that specific DNA sequences containing cytosine phosphodiester guanine (CpG) motifs in bacterial DNA as well as their synthetic counterparts, CpG oligonucleotides (CpG-ODN) possess immune stimulatory properties (9-12). In human and other mammalian cells, these bacterial CpG motifs or synthetic CpG-ODNs are recognized by intra-cellular toll-like receptor 9 (TLR9) present in the immune cells (13-16). Upon stimulation of immune cells, CpG-ODNs induce a type 1 helper (Th1) type immune response by stimulating lymphocytes (B cells, T cells and NK cells) to secrete interleukin-6 (IL-6), interleukin-12 (IL-12) and interferon-gamma (IFN-$\gamma$) ensuring the induction of a strong innate immune response (17). This immune response induced by CpG-ODN has been demonstrated to be effective in protecting animals against bacterial (18, 19) viral (20) and protozoan (21) infections.

In chicken, TLR-21 is an intracellular receptor and a functional orthologous to mammalian TLR-9, stimulating macrophages upon binding to bacterial and synthetic DNA containing CpG motifs (22, 23). The immune responses induced by CpG-ODN in chicken are a predominantly Th1 type (23, 24). It has been previously shown that CpG-ODNs induce significant immunoprotection against bacterial septicemias such as *Escherichia coli* and *Salmonella typhimurium* when administered by the parenteral route to broiler chickens or by the in ovo injection to incubating eggs (25, 26). However, these routes of administration are less practical or lack commercial applicability. The immunogenic effect through intramuscular or in ovo administrations is also short. There is therefore need to further explore variations of delivery systems for the administration of CpG-ODN for better immunoprotection.

Studies have found that mucosal delivery of the antigens alone especially DNA, using the pulmonary route is not efficient enough.

In practice, both pulmonary and nasal delivery have highlighted biological challenges that can prevent the proper delivery of vaccine to the lung. The administration of a vaccine or therapeutic via inhalation has presented obstacles in the ability to produce a sufficiently high systemic immune response (30). This has been attributed to the nebulization device, the anatomical, and the physiological features in the airways (30, 31).

For oligonucleotide vaccines, this effect is potentiated since oligonucleotides are highly susceptible to degradation in the lung environment. Although CpG-ODN has proven protective against *E. coli* challenge under experimental conditions, the main challenges include the large dosages necessary for an effective response and the rapid degradation and elimination from the circulation in vivo (32).

Vaccine administration via intramuscular or subcutaneous injection is still the standard today even though an intranasal (i.n.) vaccine against bovine respiratory disease (PMH®IN) released by Merck in 2014 exists for cattle, and spray vaccination also exists in the poultry industry (29). Coarse spray vaccines in the poultry sector are designed for administration to the eye and upper respiratory tract and these can be administered through automation at the hatchery (33).

Aside from the obvious differences that exist between the avian and mammalian respiratory system, interspecies differences also exist (35). The result is differences in rates of biotransformation, differences in breathing pattern, and tissue distributions (35). The consequence of the species differences is that each vaccine delivery system proposed must be specifically designed for a particular species (35).

An inactivated influenza vaccine has been shown to induce protection against lethal influenza challenge in chickens (34).

Nanoparticle (NP) technology has been applied to vaccine delivery and has shown some potential in veterinary medicine. A variety of lipid and biopolymer based formulations have been synthesized by many groups for effective pulmonary aerosol administration (36-43). There are a variety of nano-pharmaceuticals already available on the market (44). No approved particles have been designed for pulmonary or nasal administration.

Several NP delivery vehicles have already been tested in livestock veterinary vaccine development in order to achieve needle-free vaccination for mass immunization (29, 45, 46, 47, 53-55). Specific aerosol devices for drug delivery to the lung in veterinary species have not been described in livestock. Spray vaccination in poultry is standard against New Castle Disease virus (NDV) and Infectious Bronchitis Virus. However, spray vaccination in this regard refers to 100-200 μm liquid particles which do not specifically target inhalation.

Nasal vaccination using NPs in chickens has been tested against NDV and influenza using chitosan (56), liposome (57), and liposome-biopolymer particles (56). Moreover, coarse spray administration of liposomes carrying inactivated avian pathogenic *E. coli* (APEC) showed protection against lethal *E. coli* challenge (58).

NP vaccine formulations have been most commonly tested against *E. coli* infection, particularly with synthetic CpG-ODN adjuvants. Nanoparticle formulations containing CpG-ODNs have been found to protect against several diseases in mice, and *E. coli* and *Salmonella* in chickens (25, 46, 42, 52, 59, 60, 61). However, these particle platforms are not delivered via the pulmonary route, yet they are effective against lethal *E. coli* challenge via in ovo, intramuscular, and subcutaneous routes. NPs for the pulmonary route of vaccination in broilers presents an easier vaccination method at the industrial scale (65-67).

It has been found that particles less than 3 μm are able to bypass the mucociliary transport (62). However, larger particles deposit in the upper airways, particularly the tracheal bifurcation (62, 63). Particle deposition is also dependent on age and it was shown that in comparison to 2 and 4 week old broilers, 1-day old chicks contained more >3 μm particles in the nose and eyes and in the lower respiratory tract, while 1-3 μm particles deposited less compared to older chickens (63).

Synthetic and DNA vaccines have generally not produced strong enough immune responses in clinical trials (51, 48, 49, 50, 64).

The use of a common veterinary antigen Emulsigen® has been tested to determine improvement of CpG-ODN stimulation in terms of protection, but there was not a significant difference in protection (25).

In a recent study, four formulations categorized into single walled carbon nanotubes and lipid surfactant formulations were administered in ovo to compare whether they improved survival of chicks in comparison to unformulated CpG-ODN (32). The formulations improved the survival of chicks and lowered the bacterial counts in comparison to naked CpG-ODN. However, there were differences in the formulations. Additionally, although CpG ODNs may be effective, the window of effectiveness is limited. The formulations described can extend the effectiveness.

Formulations that can be used for intra-pulmonary delivery of CpG-ODNs are desirable.

SUMMARY

It is an object of the present application to develop compositions comprising immunostimulatory oligodeoxynucleotides such as CpG-ODN that can be delivered in a non-invasive, practical and effective manner for the induction of immunity against various infections.

In an embodiment, the present application describes a micro-droplet composition comprising one or more immunostimulatory oligodeoxynucleotides and optionally one or more pharmaceutically acceptable excipients formulated for intrapulmonary delivery.

In some embodiments, the present application includes a composition comprising one or more immunostimulatory oligodeoxynucleotides, a pharmaceutically acceptable muco-adhesive polymer, and optionally one or more pharmaceutically acceptable excipients formulated for intrapulmonary delivery. In some embodiments, the composition is a micro-droplet composition.

In one embodiment, the present application includes the use of a composition of the application comprising administering such composition through micro-droplet intrapulmonary delivery for the induction of immunity.

In some embodiments, the present application includes the use of a nebulizer for the administration of a composition of the application through micro-droplet intrapulmonary delivery for the induction of immunity.

In another embodiment, the present application includes a method for stimulating immunity in a feed animal comprising administering by intrapulmonary delivery an effective amount of micro-droplets of a composition comprising one or more immunostimulatory oligodeoxynucleotides and optionally one or more pharmaceutically acceptable excipients.

In one embodiment, the present application includes an intrapulmonary micro-droplet delivery system comprising a composition comprising one or more immunostimulatory oligodeoxynucleotides and optionally one or more pharmaceutically acceptable excipients.

Other features and advantages of the present disclosure will become apparent from the following detailed description. It should be understood, however, that the detailed description and the specific examples while indicating embodiments of the disclosure are given by way of illustration only, the scope of the claims should not be limited by the embodiments set forth in the examples, but should be given the broadest interpretation consistent with the description as a whole.

DRAWINGS

The embodiments of the application will now be described in greater detail with reference to the attached drawings in which.

DESCRIPTION OF VARIOUS EMBODIMENTS

Figure 1:
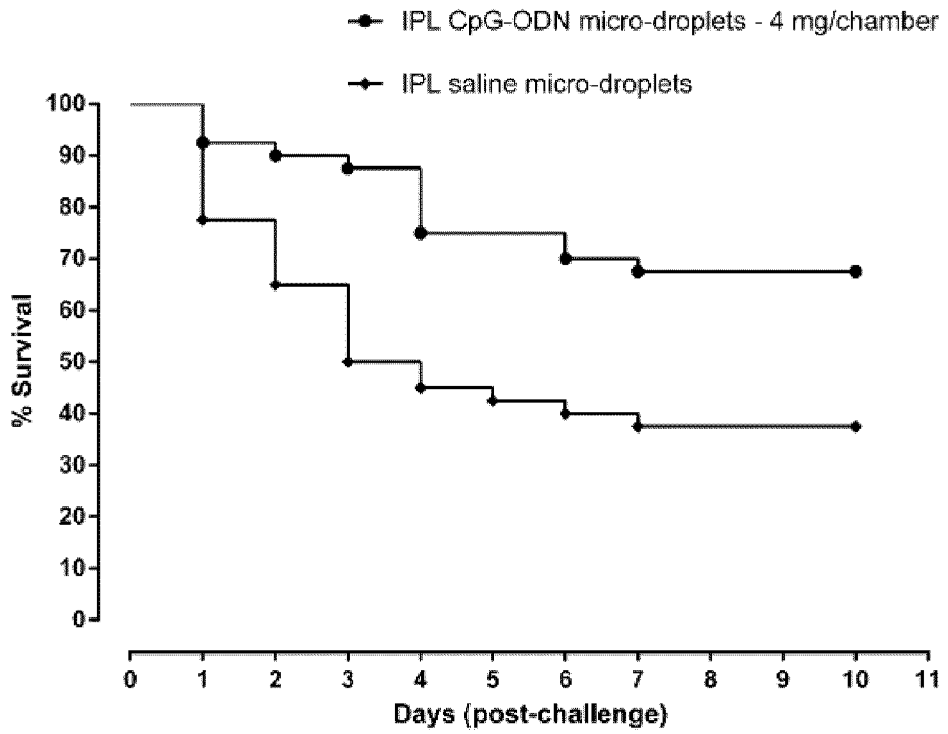
FIG. 1 shows the percent survival of neonatal broiler chickens treated with IPL CpG-ODN micro-droplets prior to a lethal *E. coli* challenge. Saline micro-droplets were used as control.

CpG-ODN DNA is a promising approach to vaccinate vulnerable broiler chicks against bacterial infections common to birds such as *E. coli* infection. Past investigations have shown that NP delivery systems can improve protection of chicks in vivo via in ovo routes of vaccination (46,32). Polyphosphazenes, liposomes, cationic lipid, and Emulsigen®, a common veterinary adjuvant, were investigated for their ability to enhance protection and prolong innate immunity generated against *E. coli* challenge after in ovo administration (46). The polyphosphazene PCPP was the only formulation to improve survival, lower bacterial count, and lower the clinical score in comparison to unformulated (naked CpG-ODN).

Different excipients, ratios, particle size, volume of dose and viscosity considerations may apply to compositions for intrapulmonary (IPL) delivery.

As described herein, gemini surfactants, phospholipids and muco-adhesive polymers, were tested as the foundation for formulation of six types of hybrid NPs for delivering CpG-ODN DNA to the respiratory tract of neonatal chicks via nebulization. Optimization of muco-adhesive polymer concentration and type for example, allowed the determination of formulations that improved CpG-ODN uptake and retention compared to the naked CpG-ODN in HD11 cells in vitro. Additionally, the formulations were able to activate NO production in macrophages, an internal mechanism for intracellular bacterial killing. Of the six formulation groups, gemini containing formulations including $G_{12}$-NPs, $G_{12}$L-NPs, PVP 10,000 $BG_{12}$L-NPs, and 1% $CG_{12,16}$-NPs were the most effective candidates for delivering CpG-ODN vaccine to broiler chicks. All four NP types were detected in the chick respiratory tract. PVP 10,000 $BG_{12}$L-NPs were able to improve protection against *E. coli* in chicks with minimal toxicity with respect to naked CpG-ODN, while hybrid NPs made with another muco-adhesive polymer did not.

Few investigators have studied the biodistribution of particles within the avian respiratory tract after spray vaccination. Of the few studies that exist, spray vaccine particles can provide local and topical treatment in air sacs. The nebulizer used in this study generates 1-5 μM sized aerosol droplets as per the manufacturer. Evidence of $G_{12}$L-NP and $BG_{12}$L-NP deposition was observed in the chick respiratory tract 2 hours after nebulization and confirms that the delivery method effectively administers the vaccine to the lung. $G_{12}$L-NPs and $BG_{12}$L-NPs deposited in the trachea, the tracheal bifurcation, and appeared to diffuse through the connective lung tissue. Accordingly compositions and their use are described.

I. Definitions

Unless otherwise indicated, the definitions and embodiments described in this and other sections are intended to be applicable to all embodiments and aspects of the present application herein described for which they are suitable as would be understood by a person skilled in the art. Each aspect so defined may be combined with any other aspect or aspects unless clearly indicated to the contrary. In particular, any feature indicated as being preferred or advantageous may be combined with any other feature or features indicated as being preferred or advantageous.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of plus or minus 0.1 to 20%, 5-20%, or 10-20%, preferably 5-15%, more preferably 5% or 10%, or of at least ±5% of the modified term if this deviation would not negate the meaning of the word it modifies.

The recitation of numerical ranges by endpoints herein includes all numbers and fractions subsumed within that range (e.g. 1 to 5 includes 1, 1.5, 2, 2.75, 3, 3.90, 4, and 5).

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "subject" as used herein refers to any member of the animal kingdom. In one embodiment, the subject is a mammal, such as a human.

The term "oligonucleotide" used herein refers to a short oligomer comprising nucleic acid residues optionally between about 3 to about 55, or any whole number between and including 3 and 55, about 8 to about 50, about 8 to about 40, 8 to about 30, about 8 to about 24, or any whole number between about 8 to about 24, or between about 13 to about 20, or between about 18 to about 25 nucleotides such as cytosine, guanine, adenine, and thymine. Uracil or modified bases can also be employed. The residues can include a ribose or a deoxyribose sugar. The oligonucleotide can be single stranded or double stranded and the linkage can be for example phosphodiester or phosphorothioate.

The term "oligodeoxynucleotide" or "ODN" used herein refers to a short oligomer comprising nucleotides such as cytosine, guanine, adenine, and thymine that comprise a deoxyribose sugar. The oligodeoxynucleotide can be single stranded or double stranded and the linkage can be for example phosphodiester or phosphorothioate.

The term "immunostimulatory oligonucleotide" as used herein refers to a category of oligonucleotides including CpG ODNs, which contain at least one CpG motif in their sequence, or PyNTTTTGT ODNs, wherein Py is C or T, and N is any deoxynucleotide.

The term "CpG-ODN" used herein refers to a strand of single-stranded synthetic nucleic acid molecule comprising at least one cytosine triphosphate deoxynucleotide followed by a guanine triphosphate deoxynucleotide connected through a phosphodiester or equivalent functional group (e.g. phosphorothioate linkage) motif, wherein the CpG is unmethylated. The strand can be between 3 to 55, for example between 12 to 24, or between 18 to 24, nucleotides long. For example, the nucleic acid molecule can be 3, 4, 5, 6, 7, 8, 9, 10, 11, 12, 13, 14, 15, 16, 17, 18, 19, 20, 21, 22, 23, or 24 nucleotides long or longer. All three classes of CpG-ODN are encompassed, class A, class B and C. Also encompassed are hybrid structures comprising CpG-ODN nucleic acid molecules. Class B CpG-ODNs include a phosphorothioate backbone and one or more CpG dinucleotides, but no poly G motifs. Encompassed by this term are related Class B CpG-ODNs including ODN 2006, ODN 2007, ODN 1668, ODN 1862, ODN BW006, and ODN D-SL01. Class C CpG-ODNs include a phosphorothioate backbone, one or more CpG dinucleotides and a CpG-containing palindromic motif.

As used herein "CpG 2007" refers to a oligonucleotide of at least 14 nucleotides and up to 22 nucleotides, and comprising the sequence TCGTCGTTGTCGTT (SEQ ID NO: 1), optionally a 22-mer having the sequence 5'-TCG TCG TTG TCG TTT TGT CGT T-3' SEQ ID NO: 2) or any part thereof comprising TCGTCGTTGTCGTT (SEQ ID NO: 1) having a phosphorothioate backbone. It is reported to be specific for porcine and bovine immune cells and is shown herein to activate chicken HD11 cells.

As used herein, "Class B CpG 2006" refers to a 24 mer CpG-ODN having the sequence '-TCGTCGTTTTGTCGTTTTGTCGTT-3' (SEQ ID NO: 3) having a phosphorothioate backbone. It is reported to be specific for human macrophages.

As used herein "between" is used inclusive of the start end point of the range and is meant to include each number in the range individually, for example the phrase "between 6 to 10", includes the range 6-10 and includes each individually (e.g. 6, 7, 8, 9 and 10 nucleotides).

The term "nanoparticle", as used herein, is meant to refer to particles, the average dimensions or diameters of which are less than about 1000 nm, preferably less than 500 nm, optionally with at least one dimension in the range of 5 nm to 500 nm.

The term "nanoparticle comprising a gemini surfactant" or "gemini nanoparticle" used herein refers to particles about 1 nm to about 1000 nm in diameter comprising one or more gemini surfactants optionally with at least one dimension in the range of 5 nm to 500 nm.

The term "surfactant" as used herein refers to a compound or mixture of compounds that reduces the surface tension between two liquids or between a liquid and a solid.

The term "gemini surfactant" as used herein refers to a moiety comprising a spacer moiety separating two cationic surfactant moieties, wherein the cationic surfactant moieties comprise a hydrophobic tail group and a cationic head group, in which the two surfactant moieties are the same or different. For example, the cationic head group optionally comprises a quaternary nitrogen group (ammonium moiety) bonded to a hydrophobic tail and the spacer, as well as two other moieties. Encompassed in this term are substituted gemini surfactants. For example, amino acid and peptide-substituted gemini surfactants are encompassed.

The term "derivative" as used herein refers to a substance which comprises the same basic carbon skeleton and functionality as the parent compound, but can also bear one or more substituents or substitutions of the parent compound.

The term "muco-adhesive" used herein refers to the tendency to adhere between two materials, where at least one of which is a mucosal surface. Examples of mucosal surfaces include but are not limited to the mucosa of the respiratory cavities.

The term "micro-droplet" used herein refers to a drop of liquid where the average diameter of the drop is between about 0.3 μm to about 10 μm, or between about 0.5 to about 5 μm. Also included are ranges between 0.3 μm to 10 μm in 0.1 μm increments, for example 1 μm or 5 μm.

The term "nebulization" used herein refers to the process of converting a liquid to the form of a mist, such as a mist containing micro-droplets. The term "nebulizer" used herein refers to a machine capable of converting a liquid to the form of a mist, such as a mist containing micro-droplets.

The term "intrapulmonary" or "IPL" used here in refers to situated within, occurring within, or administered by entering the lungs.

The term "neonatal" used herein refers to a stage of life within the first 4 weeks, or first 3 weeks, or first 2 weeks, or first week, or within the first 3 days or first 2 days or $1^{st}$ day after birth. The term "neonate" used herein refers to baby animals in the neonatal stage.

As used herein "aerosol" refers to liquid droplets (e.g. micro-droplets), that are suspended in air or another gas. Encompassed in this term is liquid suspension, and liquid solutions and combinations thereof.

As used herein, "natural inspiration" refers to delivery of an aerosol through such that the subject inhales the aerosol.

As used herein, "nebulizer" refers to a device that generates aerosols by generating small droplets form a liquid solution or suspension. Encompassed in this definition are nebulizers that generate aerosols by compression, jet nebulization, vibrating mesh or plates, or ultrasonic sound waves, and includes in particular, vibrating mesh and ultrasonic sound wave nebulizers.

As used herein, "bio-adhesive polymer", alternatively "muco-adhesive polymer", refers to a synthetic or organic polymer that is capable of adhering to a mucosal tissue of a subject. Encompassed in this term are polyvinylpyrrolidone (PVP), carboxymethylcellulose (CMC), optionally sodium CMC (CMCNa), sodium alginate, hyaluronic acid, and poly(D-L-lactide-co-glycolide) (PLGA) and combinations thereof.

Examples of PVP include PVP MW 10,000; PVP, MW 25,000; and PVP, MW 40,000. Examples of PEG include PEG 400, optionally PEG 400 N.F. and derivatives of PEG such as polyethylene glycol monomethyl ether (mPEG).

As used herein, "excipient" refers to a non-therapeutic agent added to a pharmaceutical composition to provide a desired consistency or stabilizing effect. Encompassed in this term PEG and PG as well as other excipients that can provide a desired consistency or stabilizing effect such as acetic acid, sodium hydroxide, phosphate buffered saline, pH 7.4, TE buffer, and Tris-EDTA.

As used herein, "humidity" refers to a quantity representing the amount of water vapour in the atmosphere or a gas.

As used herein, "humidex" or "humidity index" refers to a dimensionless index based on the dew point that describes the perceived temperature of a subject based on the temperature and humidity. The humidex is calculated according to the following formula:

wherein $T_{air}$ is the air temperature in ° C.; and $T_{dew}$ is the dewpoint in ° C.

5417.7530 is a rounded constant based on the molecular weight of water, latent heat of evaporation, and the universal gas constant.

As used herein, "phosphatidylcholine" refers to a phospholipid wherein the chemical structure can generally be described as comprising the following: a choline molecule, a phosphate group and glycerol, wherein fatty acyl chains of 2 to 24 carbons long are attached as R groups on the sn-1 and sn-2 positions of the glycerol molecule.

The term "day post-hatch" as used herein means within 24 hours of birth or hatching. Similarly "two day post-hatch" as used herein means within 48 hours of birth or hatching.

II. Compositions, Methods and Uses of the Application

The present disclosure relates to compositions for intrapulmonary delivery and methods of use thereof. The compositions described may in some embodiments extend the currently limited window of effectiveness of immunostimulatory formulations.

In an embodiment, the present application describes a micro-droplet composition comprising one or more immunostimulatory oligodeoxynucleotides and optionally one or more pharmaceutically acceptable excipients formulated for intrapulmonary delivery.

In some embodiments, the micro-droplet composition further comprises a pharmaceutically acceptable muco-adhesive polymer.

In some embodiments, the present application includes a composition comprising one or more immunostimulatory oligodeoxynucleotides, a pharmaceutically acceptable muco-adhesive polymer, and optionally one or more pharmaceutically acceptable excipients. The composition can be formulated for intrapulmonary delivery, particularly by nebulization. In some embodiments, the composition is a micro-droplet composition.

In some embodiments, the immunostimulatory oligodeoxynucleotides comprises a phosphorothioate backbone, a phosphodiester backbone, or a phosphorothioate/phosphodiester chimeric backbone.

In some embodiments, the immunostimulatory oligodeoxynucleotide comprises and/or consists essentially of CpG oligodeoxynucleotides (CpG-ODN).

In some embodiments, the CpG-ODN is a T-rich oligodeoxynucleotide.

Immunostimulatory oligonucleotides are described in WO2003030656 hereby incorporated by reference.

In some embodiments, the CpG-ODN is of the formula: $5'N_1X_1CGX_2N_23'$ (SEQ ID NO: 6), wherein $X_1$ and $X_2$ are nucleotides and N is any nucleotide and $N_1$ and $N_2$ are nucleic acid sequences composed of from about 0-25 N's each. In some embodiments, $X_1$ is adenine, guanine, or thymine and $X_2$ is adenine, cytosine, or thymine. In some embodiments, $X_1$ is cytosine and/or $X_2$ is guanine.

In some embodiments, the CpG-ODN is of the formula: $5'N_1X_1CGX_3X_4N_23'$ (SEQ ID NO: 7), wherein $X_1$, $X_2$, $X_3$, and $X_4$ are nucleotides, and N is any nucleotide and $N_1$ and $N_2$ are nucleic acid sequences composed of from about 0-25 N's each.

In some embodiments, the CpG-ODN has the sequence $5'TCN_1TX_1X_2CGX_3X_43'$, wherein $X_1$, $X_2$, $X_3$, and $X_4$ are nucleotides, and N is any nucleotide and $N_1$ and $N_2$ are nucleic acid sequences composed of from about 0-25 N's each (SEQ ID NO: 8). In some embodiments, $X_1X_2$ are selected from GpT, GpG, GpA, ApA, ApT, ApG, CpT, CpA, CpG, TpA, TpT and TpG. In some embodiments, $X_3X_4$ are selected from TpT, CpT, ApT, TpG, ApG, CpG, TpC, ApC, CpC, TpA, ApA, and CpA. In some embodiments, $X_1X_2$ are GpA or GpT and $X_3X_4$ are TpT.

In some embodiments, $X_1$ or $X_2$ or both are purines, and $X_3$ or $X_4$ or both are pyrimidines.

In some embodiments, $X_1X_2$ are GpA, and $X_3$ or $X_4$ or both are pyrimidines.

In some embodiments, if the immunostimulatory oligonucleotide has a phosphodiester backbone or a phosphorothioate/phosphodiester chimeric backbone, $N_1$ and $N_2$ do not contain a CCGG or a CGCG quadmer, or more than one CCG or CGG trimer or any poly G motifs.

In some embodiments, the CpG-ODN is a class B or class C CpG-ODN.

In other embodiments, the CpG-ODN is a class B CpG-ODN, optionally CpG 2007 or CpG 2006.

In some embodiments, the CpG-ODN has the sequence TCGTCGTTGTCGTTTTGTCGTT (SEQ ID NO: 2), TCGTCGTTGTCGTT (SEQ ID NO: 1), TCGCGTGCGTTTTGTCGTTTTGACGTT (SEQ ID NO: 4); TCGTCGTTTGTCGTTTTGTCGTT (SEQ ID NO: 5).

In one embodiment, the composition comprises one or more muco-adhesive polymer. In a further embodiment, the one or more muco-adhesive polymer is/are selected from PVP, poly(D-L-lactide-co-glycolide) (PLGA), CMC, sodium alginate, and hyaluronic acid. In another embodiment, the one or more muco-adhesive polymer are selected from PVP and CMC. In a preferred embodiment, the one or more muco-adhesive polymers are PVP MW 10,000 and PEG 400 or CMCNa. In a further embodiment, the PVP has a molecular weight of about 10,000 or about 40,000.

In some embodiments, the muco-adhesive polymer is comprised in, complexed with or in the form of nanoparticles or liposomes.

In some embodiments, the nanoparticles comprise a gemini surfactant, and optionally further comprise a lipid and/or muco-adhesive polymer.

Various gemini surfactants can be used. Gemini surfactants as described in Formula II of US 20140113977 and as described in US 20080112915 hereby incorporated by reference may be used in some embodiments.

In a further embodiment, the gemini surfactant has a hydrocarbon tail that is 12 to 18 carbons in length. In another embodiment, the cationic head group bound to the hydrocarbon tail is an ammonium moiety. In another embodiment, the gemini surfactant has a spacer molecule of 3 to 7 carbons in length, preferably 3 carbons in length. In a further embodiment, the gemini surfactant comprises two 12 carbon hydrocarbon tails and a 3 carbon spacer molecule (Gemini 12-3-12) or two 16 carbon hydrocarbon tails and a 2 carbon spacer molecule (Gemini 16-3-16).

In an embodiment, the nanoparticle further includes one or more phospholipids.

Phospholipids such as phosphatidylcholine (PC), and phosphatidylethanolamine (PE) can be incorporated. The PC can be one or more of soybean phosphatidylcholine, egg phosphatidylcholine, and synthetic phosphatidylcholine, as well as hydrogenated phosphatidylcholine.

In an embodiment, the phoshpholipid is 1, 2-dioleoyl-sn-glycero-3-phosphoethanolamine (DOPE), or 1,2-dipalmitoyl-sn-glycero-3-phosphocholine (DPPC). In some embodiments, the phospholipid is pegylated. In further a further embodiment, the pegylated phospholipid is 1,2-Distearoyl-sn-glycero-3-phosphoethanolamine mPEG (mPEG-DSPE).

In one embodiment, the composition comprises nanoparticles comprising one or more gemini surfactant and one or more muco-adhesive polymer. In a further embodiment, the gemini surfactant is Gemini 12-3-12 and the one or more muco-adhesive polymer is selected from PVP, and CMCNa. In a further embodiment, the gemini surfactant is Gemini 12-3-12 and the muco-adhesive polymer is CMCNa. In a preferred embodiment, the gemini surfactant is Gemini 12-3-12 and the muco-adhesive polymer is PVP MW 10,000.

In one embodiment, the composition comprises nanoparticles comprising one or more gemini surfactant, one or more muco-adhesive polymer, and one or more phospholipid. In a further embodiment, the gemini surfactant is Gemini 12-3-12; the one or more muco-adhesive polymer is selected from PVP, and CMCNa; and the one or more phospholipid is phosphatidylcholine (PC), optionally selected from DPPC, soybean phosphatidylcholine, egg phosphatidylcholine, or synthetic phosphatidylcholine, as well as hydrogenated phosphatidylcholine.

In a preferred embodiment, the composition comprises Gemini 12-3-12, CMCNa, PEG, and DPPC.

In a preferred embodiment, the composition comprises Gemini 12-3-12, CMCNa, PEG 400, and DPPC.

In a preferred embodiment, the composition comprises Gemini 12-3-12, PVP MW 10,000; PEG 400; and DPPC.

In one embodiment, the composition comprises one or more excipients. In a further embodiment, the one or more excipients is selected from acetic acid; sodium hydroxide; saline, including sterile saline, optionally phosphate buffered saline; Tris-EDTA; TE buffer, PEG, and PG and combinations thereof. In another embodiment, the excipient is PEG. In a further embodiment, the PEG is PEG 400, or polyethylene glycol monomethyl ether.

In one embodiment, the amount of PC, optionally DPPC in a composition is about 0.1% to about 20% (m/v) of total volume of the final composition, or any 0.1% increment therebetween.

In one embodiment, the amount of gemini surfactant, optionally 12-3-12 or 16-3-16, used in the composition is between about 0.01% to about 5% (m/v) of the total volume of the final composition, or any 0.01% increment therebetween.

In one embodiment, the amount of excipient used in the composition, wherein the excipient used is PG or PEG 400, is between about 1% to about 20% (m/v) of the total volume of the final composition, or any 0.5% increment therebetween.

In one embodiment, the amount of muco-adhesive polymer used in the composition wherein the muco-adhesive polymer used is PVP MW 40,000; PVP MW 10,000; or CMCNa, is between about 0.1% to about 20% (m/v) of the total volume of the final composition, or any 0.1% increment therebetween.

In one embodiment, the amount of CpG in the composition is about 0.001% 0.5 (m/v) of the total volume of the final composition, or any 0.001% increment therebetween.

As shown in the Examples, various nanoparticle compositions were tested. In an embodiment, the composition may be a composition described in the Examples or Drawings, optionally including compositions selected from the compositions described in Tables 1, 2, 4, 9, 10, and 11 and/or in Example 2. In another embodiment, the composition comprises a composition provided in any one of Tables 1 and 4.

The immunostimulatory oligodeoxynucleotide and the gemini nanoparticle can be complexed together into an oligodeoxynucleotide-nanoparticle complex.

In some embodiments, the oligonucleotide-nanoparticle complex has a size similar to a size described herein. In an embodiment, the complex has an average size from about 4 nm to about 1500 nm, optionally less than 500 nm, or less than 300 nm. Preferably the complex has an average size between about 100 to about 500 nm, more preferably between about 100 to about 250 nm, or any whole number therebetween. The diameter can for example be the Z average size measured by DLS. For example, as shown in the Examples the diameter range is between about 145 nm to 185 nm for GL-NP, from about 170 nm to 180 nm GLP-NP and from about 160 nm to 170 nm for G-NP.

In an embodiment, the compositions described herein are used as an adjuvant and can comprise one or more antigens. In a further embodiment, the antigen is an antigen that is when formulated produces an antigen-oligodeoxynucleotide-nanoparticle complex that has an average size from about 4 nm to about 1500 nm, optionally less than 500 nm, or less than 300 nm. Preferably the complex has an average size between about 100 to about 500 nm, more preferably between about 100 to about 250 nm, or any whole number therebetween.

In some embodiments, at least 50% of the micro-droplets have a diameter less than about 5 μm, less than about 4 μm, less than about 3 μm, less than about 2 μm, less than about 1 μm and greater than about 0.5 μm, or from about 0.5 to about 5 μm.

In some embodiments, the pharmaceutically acceptable excipient is saline, such as sterile saline, optionally phosphate buffered saline.

The composition can also comprise one or more carriers.

In some embodiments, the composition is for or comprises a dose that is for immune-stimulation.

In some embodiments, the composition is formulated for a dosage comprising between about 25 μg to about 500 μg of CpG-ODN, 25 μg to about 200 μg of CpG-ODN or at least 25 μg of CpG-ODN, at least 50 μg, at least 75 μg, at least 100 μg, at least 150 μg or at least 200 μg of CpG-ODN. The dosage can for example be comprised as a liquid dosage, for example in a volume of about 50 μL to about 100 μL of solution.

In an embodiment, the composition comprises sufficient CpG-ODNs for about 500, 1000 or 5000 doses or any number of dosages between 100 and 5000, wherein each dose comprises a composition comprising about or at least 25 μg of CpG-ODN or a dosage described herein.

In an embodiment, the composition has an average polydisperity index (PD) of less than 0.5. In another embodiment the PD is less than 0.4, more preferably less than 0.3.

In an embodiment, the composition is a micro-droplet composition. In an embodiment, the composition is a nebulized composition or is suitable for nebulizaiton.

Another aspect of the disclosure includes use of a composition of the disclosure, for example for the promotion and/or induction of immunity. Any of the compositions described herein can be administered.

Also provided in another aspect is a method for stimulating immunity in a feed animal comprising administering by intrapulmonary delivery an effective amount of micro-droplets of a composition comprising one or more immunostimulatory oligodeoxynucleotides and optionally one or more pharmaceutically acceptable excipients. Any of the compositions described herein can be administered.

In some embodiments, the composition has immunostimulatory effect lasting for at least 3, at least 4, at least 5, or at least 6 days.

In another embodiment, the composition is formulated for micro-droplet intrapulmonary delivery. In some embodiments, the composition is administered by or is for administration by a needle-free intrapulmonary delivery.

In an embodiment, the viscosity of the composition is less than about 5000 centipoise (cP), optionally less than about 4000 centipoise, less than about 3000 centipoise, less than about 2000 centipoise or any whole number between 2000 and 5000 centipoise.

In some embodiments, the method or use is for the reduction of infection, such as bacterial infection.

In an embodiment, the composition is administered or for administration through a device that permits natural inspiration. The composition is administered or formulated for administration using for example a nebulizer. In an embodiment, the nebulizer is an ultrasonic sound wave nebulizer. In another embodiment, the nebulizer is a vibrating mesh nebulizer.

Figure 10:
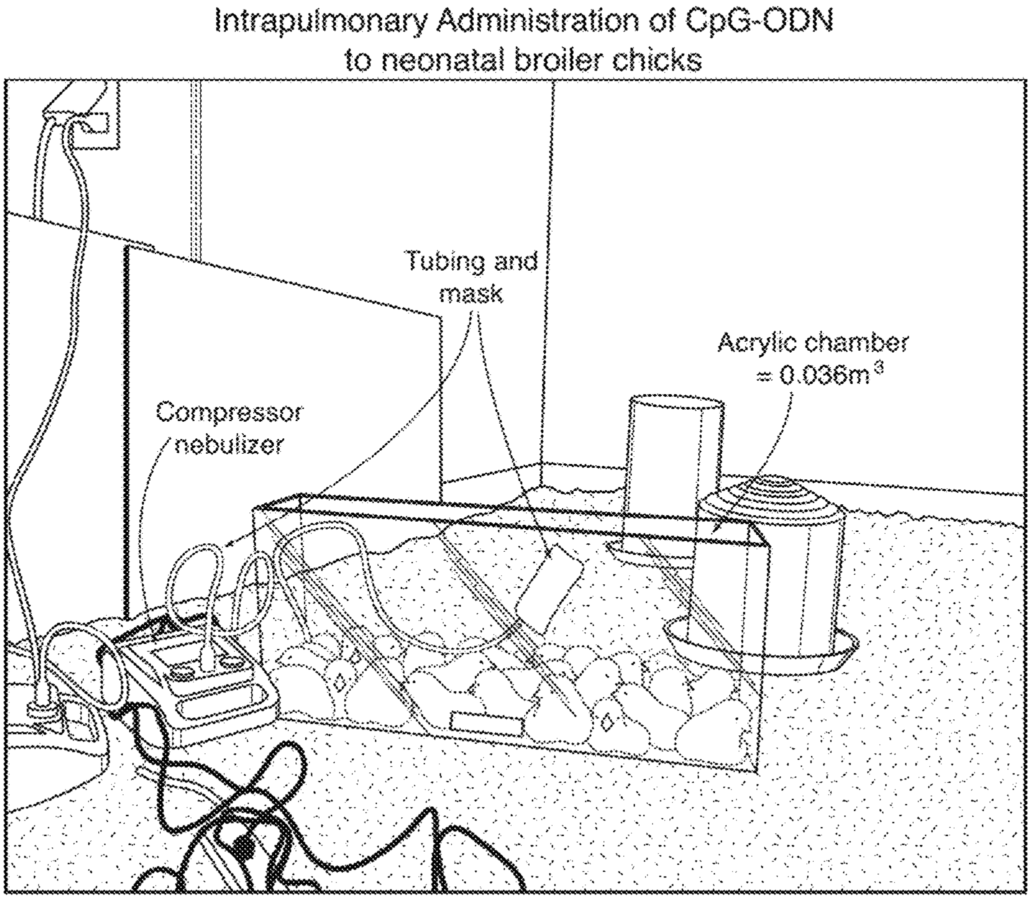
FIG. 10 shows a set-up for the administration of CpG-ODN NP formulations via nebulization that can be used with 1-day old chicks.

In a further embodiment, the composition is administered or for administration using a device as shown in FIG. 10.

Nebulizers capable of providing a desired droplet size, as well as desired temperature, humidity and $CO_2$ level can be used in the methods and uses described herein.

For example, nebulizers that can generate liquid droplets of about 5 μm (for example 0.3 μm to 10 μm), each droplet comprising a plurality of nanoparticles can be used. Spray droplets are typically over 100 μm. The inventors have found that nebulized liquid droplets are able to penetrate deep into the bird lungs. The blood and air barrier at the deep lung level where gaseous exchange takes place is typically a single cell thick. Small particles such as those prepared herein may be able to deliver CpGODN into the blood stream of the subject. In some embodiments, the method or use is for the induction of immunity in a feed animal.

In some embodiments, the feed animal is exposed to the composition for at least about 10 min, at least about 15 min, at least about 20 min, at least about 25 min, at least about 30 min, or at least about 35 min.

In an embodiment, the feed animal is a turkey, layer hen, or broiler chicken. In some embodiments, the feed animal is a broiler chicken.

In some embodiments, the feed animal is a neonate, optionally less than or about 3 days post-hatch, less than or about 2 days post hatch, or less than or about 1 day post-hatch. In a preferred embodiment, the composition is administered to a feed animal at 1 day post hatch. In another embodiment, the administration is repeated. In a preferred embodiment, the administration is repeated after 3 or more, 4 or more, 5 or more or 6 or more days. In a further embodiment, the administration is repeated after 6 or more days.

In an embodiment, the feed animal is administered about 1 mg to about 4 mg of CpG-ODN/0.036 $m^3$ of chamber. In a further embodiment, the feed animal is administered a dose between about 25 μg up to about 500 μg of CpG-ODN or any dosage described herein. In a preferred embodiment, the feed animal is administered a dose of about 25 μg to about 200 μg of CpG-ODN, or about 25 μg to about 100 μg of CpG-ODN, for example in about 50 μL to about 100 μL of solution. For example the solution is 100 μL prior to micro-droplet formation/nebulization.

In an embodiment, the dosage amount of CpG-ODN administered to the feed animal is at least 25 μg. In an embodiment, the amounts provided are based on the molecular weight of the 2007 ODN, and the amounts are adjusted for CpG-ODNs that larger than 2007.

It was also determined by the inventors that humidity and temperature have an effect on the IPL delivery of CpG-ODNS by nanoparticles.

In an embodiment, the feed animal is administered the composition in chamber where the average temperature is about 22° C. to about 24° C. optionally at about 22° C., about 23° C. or about 24° C.

In a further embodiment, the feed animal is administered the composition in chamber or housing where the humidity is less than 70%, less than 65% or less than 60%, optionally between about 40% and about 70%, preferably 40-60%.

In a preferred embodiment, the feed animal is administered the composition in chamber where the humidex is, below or about 28, or below or about 27 or below 26.

As described herein, the micro-droplets are produced using a nebulizer.

In another aspect, the disclosure includes an intrapulmonary micro-droplet delivery system for delivery of and/or comprising a composition described herein. In a further embodiment, the micro-droplet delivery system is a device or container. In a further embodiment, the intrapulmonary micro-droplet delivery device container is a component of a compressor nebulizer. In a further embodiment, the intrapulmonary micro-droplet delivery system comprises a chamber for removably containing feed animals, a nebulizer compressor capable of producing microdroplets, and a tube connecting the nebulizer compressor to the chamber.

In an embodiment, the micro-droplet delivery system is a nebulizer-chamber capable of delivering a composition described herein. In an embodiment, the chamber is capable of nebulizing a composition for administration to for example 5, 100, 500, 1000 feed animals or more (for example up to 1,000 1 day-old chicks).

In some embodiments, the intrapulmonary micro-droplet delivery system is for delivering a composition of the present disclosure.

It is understood that CpG-ODNs used in the present application can be synthesized using methods known to one skilled in the art that are commonly known, or purchased from commercial companies, for example Operon Biotechnologies, Inc, Huntsville, AL, USA. It is understood that all chemicals and starting material can be purchased from commercial sources such as Sigma Aldrich. It is understood that the compounds, compositions of the application such as CpG-ODN, gemini surfactants or CpG-ODN nanoparticles, or compositions comprising thereof can be purchased or made according to methods described herein and known in the art, for example according to the procedures described herein or optionally in "Horizons in Clinical Nanomedicine" Foldvari M, Pan Stanford, 2014, Chapter 6 "Nanopharmaceutics: Structural Design of Cationic Gemini Surfactant-phospholipid-DNA Nanoparticles for Gene Delivery".

In one embodiment the device chosen to administer the composition uses natural inspiration. For example, the device can be a nebulizer. In a preferred embodiment, the device is a compressor nebulizer. For example, the nebulizer can be comprised as part of or connected to an enclosed housing as shown in FIG. 10 to provide subjects therein with the aerosolized composition.

In one embodiment, the composition is administered using a nebulizer. In a further embodiment, the nebulizer creates 0.3-10 μM aerosol droplets. In a preferred embodiment the average size of an aerosol droplet is less than 5 μm or less than 1 μm.

In one embodiment, the dose of CpG-ODN administered per chick is between about 25 μg to 500 μg, optionally between about 25 μg to 200 μg. In another embodiment, the dose administered per chick is about or at least 25 μg, 50, 75, 100, 125, 150, 175, or 200. In a further embodiment, the dosage administered is 100 μg per chick.

A further aspect includes a container comprising 500, 1000, or 5000 doses, wherein each does comprises a composition comprising for example about or at least 25 μg, 50, 75, 100, 150, or 200 of CpG-ODN.

In one embodiment, the composition is administered to poultry. In another embodiment, the composition is administered to turkeys. In another embodiment, the composition is administered to layer hens. In a preferred embodiment, the composition is administered to broiler chickens.

In an embodiment, the ratio of gemini surfactant to immunostimulatory oligodeoxynucleotides is from about 1:1 to 10:1. In a further embodiment, the ratio is about 1.5:1 to 3:1. In a preferred embodiment, the ratio is about 1.8:1, 2:1, or 2.2:1. In a further embodiment, the ratio is about 4:1, 5:1, 6:1, 7:1, 8:1, or 9:1.

As shown in Example 10, the nanoparticle formulations with a zeta potential above 30MV were more stable than those below 30MV. For example it was shown, that the zeta potential of $G_{12}$NP is between 37 and 47MV. In another embodiment, the zeta potential of PVP 10,000 $BG_{12}$L-NP can be between 42 and 43MV and the zeta potential of CMCNa $BG_{12}$L-NP can be between 33 and 39MV. In one embodiment, the nanoparticle formulations have an average zeta potential of at least 32MV, at least 35 MV, at least 38 MV or at least 40 MV.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

CpG-ODN Labeling

The nucleotide was labeled using the Ulysis™ Alexa Fluor™ 647 Nucleic Acid Labeling Kit (Life Technologies, Burlington, Ontario, Canada) according to manufacturer's instructions at a labeling ratio of 100 μg per labeling reaction.

Example 2

Nanoparticle Preparation and Characterization

Several types of NP formulations were prepared: gemini only (G-NPs), gemini-phospholipid (GL-NP), gemini-phospholipid-biopolymer (BGL-NP), phospholipid-another biopolymer (C) (CL-NP), another biopolymer (C)-gemini (CG-NP), another biopolymer (C) (C-NP), hyaluronic acid (HA-NP), and another biopolymer (C)-sodium alginate (CA-NP). The $G_{12}$L-NP (no biopolymer) and PVP 10,000 $BG_{12}$L-NP (PVP 10,000 polymer coating).

The following excipients and materials were used in formulation development. Solvents used included autoclaved MilliQ water (prepared in house) and biotech grade water (Fisher Bioreagents) used to dissolve polymers and CpG-ODN, respectively. The selected polymers included polyvinylpyrrolidone (PVP), MW 10,000, PVP 10,000; Kollidon® 25); PVP, MW 40,000, PVP 40,000 (Sigma Aldrich, St. Louis, Missouri, USA)); Avicel RC-591 sodium carboxymethylcellulose (CMCNa) (FMC Biopolymer, Philadelphia, Pennsylvania, USA); PROTANAL® CR 8133 (sodium alginate), (FMC Biopolymer); hyaluronic acid (Creative PEGWorks); mPEG-DSPE (Creative PEGWorks); propylene glycol USP, (PG) (Spectrum Laboratory Products Inc., Gardena, California, USA); polyethylene glycol 400 N.F. (PEG 400) (Spectrum Laboratory Products Inc.)

Lipids used included 1,2-Dipalmitoyl-sn-glycero-3-phosphocholine (DPPC) (Sigma Aldrich); Phospholipon 100H, Nattermann, Batch #92000300, Identification #13052;

Gemini surfactants included three first generation compounds (without modification): Gemini 12-3-12 (manufactured in house Lot #:120804-3); Gemini 16-3-16 (manufactured in house Lot #:280404); Gemini 18-3-18 (manufactured in house Lot #:070606-3)

Other excipients used were acetic acid (Sigma Aldrich); sodium hydroxide (Sigma Aldrich); phosphate buffered saline, pH 7.4; Tris-EDTA, TE buffer (Thermo Fisher Scientific, Rockford, Illinois, USA)

TABLE 1

Gemini-phospholipid NP formulations ($G_{12}$L-NPS, $BG_{12}$L-NPS)

| Formulation Number in FIG. 19C | Formulation code | Formulation components | Concentration in final formulation |
|---|---|---|---|
| 1 | $G_{12}$L-NP (PEG 400) | DPPC | 10 mg/mL |
| | | Gemini surfactant 12-3-12 | 2.2 mg/mL |
| | | PEG400 | 10 mg/mL |
| | | Water | 4.87 mg/mL |
| | | CpG Solution | 1 mg/mL |
| 3 | PVP 10,000 $BG_{12}$L-NP (PEG 400) | DPPC | 10 mg/mL |
| | | Gemini surfactant 12-3-12 | 2.2 mg/mL |
| | | PEG400 | 10 mg/mL |
| | | PVP 10,000 | 4.87 mg/mL |
| | | CpG Solution | 1 mg/mL |
| 4 | PVP Kollidon 25 $BG_{12}$L-NP (PEG 400) | DPPC | 10 mg/mL |
| | | Gemini surfactant 12-3-12 | 2.2 mg/mL |
| | | PEG400 | 10 mg/mL |
| | | PVP Kollidon 25 | 4.87 mg/mL |
| | | CpG Solution | 1 mg/mL |
| 5 | PVP 40,000 $BG_{12}$L-NP (PEG 400) | DPPC | 10 mg/mL |
| | | Gemini surfactant 12-3-12 | 2.2 mg/mL |
| | | PEG400 | 10 mg/mL |
| | | PVP 40,000 | 4.87 mg/mL |
| | | CpG Solution | 1 mg/mL |
| 6 | CMCNa $BG_{12}$L-NP (PEG 400) | DPPC | 10 mg/mL |
| | | Gemini surfactant 12-3-12 | 2.2 mg/mL |
| | | PEG400 | 10 mg/mL |
| | | CMCNa | 4.87 mg/mL |
| | | CpG Solution | 1 mg/mL |
| 2 | $G_{12}$L-NP (PG) | DPPC | 10 mg/mL |
| | | Gemini surfactant 12-3-12 | 2.2 mg/mL |
| | | Propylene glycol | 10 mg/mL |
| | | Water | 4.87 mg/mL |
| | | CpG Solution | 1 mg/mL |
| 7 | PVP 10,000 $BG_{12}$L-NP (PG) | DPPC | 10 mg/mL |
| | | Gemini surfactant 12-3-12 | 2.2 mg/mL |
| | | Propylene glycol | 10 mg/mL |
| | | PVP 10,000 | 4.87 mg/mL |
| | | CpG Solution | 1 mg/mL |
| 8 | PVP Kollidon 25 $BG_{12}$L-NP (PG) | DPPC | 10 mg/mL |
| | | Gemini surfactant 12-3-12 | 2.2 mg/mL |
| | | Propylene glycol | 10 mg/mL |
| | | PVP Kollidon 25 | 4.87 mg/mL |
| | | CpG Solution | 1 mg/mL |
| 9 | PVP 40,000 $BG_{12}$L-NP (PG) | DPPC | 10 mg/mL |
| | | Gemini surfactant 12-3-12 | 2.2 mg/mL |
| | | Propylene glycol | 10 mg/mL |
| | | PVP 40,000 | 4.87 mg/mL |
| | | CpG Solution | 1 mg/mL |
| 10 | CMCNa $BG_{12}$L-NP (PG) | DPPC | 10 mg/mL |
| | | Gemini surfactant 12-3-12 | 2.2 mg/mL |
| | | Propylene glycol | 10 mg/mL |
| | | CMCNa | 4.87 mg/mL |
| | | CpG Solution | 1 mg/mL |

* CpG-ODN was dissolved in biotech grade water with a final concentration of 4 mg/mL

TABLE 2

| Lipid-gemini PEG hybrid NP formulations | | | |
|---|---|---|---|
| Formulation Number in FIG. 19C | Formulation code | Formulation components | Concentration in final formulation |
| 39 | 7a | DPPC | 10 mg/mL |
| | | mPEG-DSPE | 1 mg/mL |
| | | Gemini 12-3-12 | 2.2 mg/mL |
| | | CpG-ODN | 1 mg/mL |
| | | Sterile water | q.s. to 1 mL |

TABLE 3

| Another biopolymer (C) Lipid NP formulations (CL-NPs) | | | |
|---|---|---|---|
| Formulation Number in FIG. 19C | Formulation code | Formulation components | Concentration in final formulation |
| 40 | CL-NP (T5) | Phospholipon 100H | 25 mg/mL |
| | | Propylene Glycol | 25 mg/mL |
| | | Another biopolymer (C) | 2.2 mg/mL |
| | | CpG-ODN | 1 mg/mL |

TABLE 3-continued

| Another biopolymer (C) Lipid NP formulations (CL-NPs) | | | |
|---|---|---|---|
| Formulation Number in FIG. 19C | Formulation code | Formulation components | Concentration in final formulation |
| | | 4M NaOH | q.s. to pH 5.2 |
| | | Sterile Water | q.s. to 1 mL |

TABLE 4

| Gemini CpG-ODN NP Complexes (G-NPs) | | | |
|---|---|---|---|
| Formulation Number in FIG. 19C | Formulation code | Formulation components | Concentration in final formulation |
| 11 | $G_{12}$-NP | Gemini 12-3-12 | 1.65 mg/mL |
| | | CpG-ODN | 1 mg/mL |
| 12 | $G_{16}$-NP | Gemini 16-3-16 | 1.65 mg/mL |
| | | CpG-ODN | 1 mg/mL |
| 13 | $G_{18}$-NP | Gemini 18-3-18 | 1.65 mg/mL |
| | | CpG-ODN | 1 mg/mL |

* Gemini powder was dissolved in sterile molecular grade water. Starting concentration of gemini solutions were 2.2 mg/mL, CpG-ODN starting concentration was 4 mg/mL

TABLE 5

| Another biopolymer (C) Nanoparticles (C-NPs) | | | |
|---|---|---|---|
| Formulation Number in FIG. 19C | Formulation code | Formulation components | Concentration in final formulation |
| 27 | 0.1% Low MW C-NP (10, 10d) | CpG-ODN | 1 mg/mL |
| | | 0.1% Another biopolymer (C) low MW stock solution in 1% acetic acid | 7.22 mg/mL |
| 29 | 1% ultra-low MW C-NP (16) | CpG-ODN | 1 mg/mL |
| | | 1% Another biopolymer (C) ultra low MW stock solution in 1% acetic acid | 7.5 mg/mL |
| 28 | 1% ultra-low MW C-NP (1f) | CpG-ODN | 1 mg/mL |
| | | 1.5% Another biopolymer (C) ultralow stock solution in 1% acetic acid | 10 mg/mL |

* CpG-ODN was dissolved in biotech grade water at 4 mg/mL prior, final formulations had a pH range of 3.5-4.2

TABLE 6

| Second generation another biopolymer (C) NP formulations (CG-NPs) | | | |
|---|---|---|---|
| Formulation Number in FIG. 19C | Formulation code | Formulation components | Concentration in final formulation |
| 14 | 0.1% $CG_{12}$-NP (11b-12) | Gemini 12-3-12 | 0.44 mg/mL |
| | | CpG-ODN | 1 mg/mL |
| | | 0.1% Another biopolymer (C) stock solution | 0.55 mg/mL |
| 26 | 0.1% $CG_{12}$-NP TE (11b-TE) | Gemini 12-3-12 | 0.44 mg/mL |
| | | CpG-ODN in TE buffer | 1 mg/mL |
| | | 0.1% Another biopolymer (C) stock solution | 0.55 mg/mL |
| 15 | 0.1% $CG_{16}$-NP (11b-16) | Gemini 16-3-16 | 0.44 mg/mL |
| | | CpG-ODN | 1 mg/mL |
| | | 0.1% Another biopolymer (C) stock solution | 0.55 mg/mL |
| 16 | 0.1% $CG_{18}$-NP (11b-18) | Gemini 18-3-18 | 0.44 mg/mL |
| | | CpG-ODN | 1 mg/mL |
| | | 0.1% Another biopolymer (C) stock solution | 0.55 mg/mL |

TABLE 6-continued

Second generation another biopolymer (C) NP formulations (CG-NPs)

| Formulation Number in FIG. 19C | Formulation code | Formulation components | Concentration in final formulation |
|---|---|---|---|
| 17 | 1% $CG_{12}$-NP (11d-12) | Gemini 12-3-12 | 0.44 mg/mL |
| | | CpG-ODN | 1 mg/mL |
| | | 1% Another biopolymer (C) in 1% acetic acid pH 4.0 | 5.5 mg/mL |
| 18 | 1% $CG_{16}$-NP (11d-16) | Gemini 16-3-16 | 0.44 mg/mL |
| | | CpG-ODN | 1 mg/mL |
| | | 1% Another biopolymer (C) stock solution | 5.5 mg/mL |
| 19 | 1% $CG_{18}$-NP (11d-18) | Gemini 18-3-18 | 0.44 mg/mL |
| | | CpG-ODN | 1 mg/mL |
| | | 1% Another biopolymer (C) stock solution | 5.5 mg/mL |
| 23 | 2% $CG_{12}$-NP (11f-12) | Gemini 12-3-12 | 0.44 mg/mL |
| | | CpG-ODN | 1 mg/mL |
| | | 2% Another biopolymer (C) stock solution | 11 mg/mL |
| 24 | 2% $CG_{16}$-NP (11f-16) | Gemini 16-3-16 | 0.44 mg/mL |
| | | CpG-ODN | 1 mg/mL |
| | | 2% Another biopolymer (C) stock solution | 11 mg/mL |
| 25 | 2% $CG_{18}$-NP (11f-18) | Gemini 18-3-18 | 0.44 mg/mL |
| | | CpG-ODN | 1 mg/mL |
| | | 2% Another biopolymer (C) stock solution | 11 mg/mL |
| 20 | 0.1% $CG_{12}$-NP PBS (11e-12) | Gemini 12-3-12 | 0.44 mg/mL |
| | | CpG-ODN | 1 mg/mL |
| | | 0.1% Another biopolymer (C) stock solution | 0.4 mg/mL |
| | | Phosphate buffered Saline | 150 μL/mL |
| 21 | 0.1% $CG_{16}$-NP PBS (11e-16) | Gemini 16-3-16 | 0.44 mg/mL |
| | | CpG-ODN | 1 mg/mL |
| | | 0.1% Another biopolymer (C) stock solution | 0.4 mg/mL |
| | | Phosphate buffered Saline | 150 μL/mL |
| 22 | 0.1% $CG_{18}$-NP PBS (11e-18) | Gemini 18-3-18 | 0.44 mg/mL |
| | | CpG-ODN | 1 mg/mL |
| | | 0.1% Another biopolymer (C) stock solution | 0.4 mg/mL |
| | | Phosphate buffered Saline | 150 μL/mL |

*gemini was dissolved in sterile MilliQ water at 2.2 mg/mL, CpG-ODN was dissolved in biotech grade water at 4 mg/mL.

TABLE 7

Sodium Alginate NP formulations

| Formulation Number in FIG. 19C | Formulation code | Formulation components | Concentration in final formulation |
|---|---|---|---|
| 35 | AC-NP (3-1b) | Sodium Alginate | 0.044 mg/mL |
| | | CpG-ODN | 1 mg/mL |
| | | 1.5% Another biopolymer (C) ultra low stock solution | 10 mg/mL |
| 34 | A-NP (13a) | CpG-ODN | 1 mg/mL |
| | | Sodium alginate | 3.3 mg/mL |
| 36 | $AG_{12}$-NP (13b-12) | Gemini 12-3-12 | 0.44 mg/mL |
| | | CpG-ODN | 1 mg/mL |
| | | Sodium Alginate | 2.42 mg/mL |
| 37 | $AG_{16}$-NP (13b-16) | Gemini 16-3-16 | 0.44 mg/mL |
| | | CpG-ODN | 1 mg/mL |
| | | Sodium Alginate | 2.42 mg/mL |
| 38 | $AG_{18}$-NP (13b-18) | Gemini 18-3-18 | 0.44 mg/mL |
| | | CpG-ODN | 1 mg/mL |
| | | Sodium Alginate | 2.42 mg/mL |

Sodium alginate was dissolved in sterile milliQ water at 4.4 mg/mL. Gemini was dissolved in sterile MilliQ water at 2.2 mg/mL. CpG-ODN was dissolved in biotech grade water at 4 mg/mL.

TABLE 8

Hyaluronic Acid NP formulations

| Formulation Number in FIG. 19C | Formulation code | Formulation components | Concentration in final formulation |
|---|---|---|---|
| 30 | 1c | 0.01% Hyaluronic Acid | 0.01 mg/mL |
| | | CpG-ODN | 1 mg/mL |
| | | 1.5% Another biopolymer (C) ultra low MW solution | 10 mg/mL |
| 31 | 12 | CpG-ODN | 1 mg/mL |
| | | 0.01% Hyaluronic acid | 0.5 mg/mL |
| 32 | 12a | CpG-ODN | 1 mg/mL |
| | | 0.01% Hyaluronic Acid | 0.025 mg/mL |
| | | 0.1% Another biopolymer (C) solution | 0.5 mg/mL |
| 33 | 12aTE | CpG-ODN in TE | 1 mg/mL |
| | | 0.01% Hyaluronic Acid | 0.025 mg/mL |
| | | 0.1% Another biopolymer (C) solution | 0.5 mg/mL |

* Hyaluronic acid was dissolved in sterile milliQ water (m/v).

Formulations were prepared with non-labeled CpG-ODN for characterization purposes and with Alexa Fluor 647 labeled CpG-ODN for further in vitro and in vivo experiments. For blank particles formulations, CpG-ODN solution was replaced with sterile water.

Gemini Phospholipid Nanoparticle Preparation ($G_{12}$L-NPs)

DPPC and the appropriate gemini surfactant, were weighed in a glass scintillation vial. The excipient (PEG400 or PG) was weighed and added to the lipid and surfactant. The contents were heated in a 75° C. water bath and vortex mixed intermittently with heating until all ingredients were uniformly mixed (lipid phase).

Variation of Biopolymer

Polymer solutions were dissolved in sterile MilliQ water. Each biopolymer was diluted as a stock solution of 100 mg in 15 mL water. The polymer solution (or water for non-biopolymer formulation) was heated to 40° C. and added to the lipid phase and vortex mixed and heated intermittently in a 75° C. water bath until the mixture was homogeneous and uniform until there were no visible particles. The solution was cooled to 40° C. and CpG-ODN was added to the vesicles and vortex mixed and warmed intermittently until formulation was translucent, uniform and there were no visible particles. Final formulation was bath sonicated for 5 minutes to evenly distribute particles.

Gemini CpG-ODN NP Complexes (G-NPs)

Gemini 12-3-12, 16-3-16, 18-3-18 solutions were also prepared in MilliQ water at room temperature, with the exception of gemini 16-3-16 and 18-3-18 which were heated briefly to 60° C. in order to uniformly dissolve.

CpG-ODN lyophilized powder was reconstituted using sterile biotech grade water to make a stock solution of 4 mg/mL. Appropriate volumes of the stock solution were used for the formulations. The final CpG-ODN concentration in the NP formulations was 1 mg/mL, unless otherwise noted.

Gemini complexes with CpG-ODN were formed at room temperature by the addition of CpG-ODN solution to gemini solution while stirring with magnetic stir bar at 900 rpm. NP complexes were sonicated for 10 minutes or until the formulation was translucent (Table 4).

Another Biopolymer (C) NP Preparation

Stock Solution Preparation 0.1%, 1%, 2% m/v were dissolved in 1% v/v acetic acid in order to produce Another biopolymer (C) NPs and tested.

Gemini 12-3-12 solutions were also prepared in MilliQ water at room temperature. Gemini 16-3-16 and 18-3-18 were heated at 60° C.

CpG-ODN stock solution was made at 4 mg/mL. The final CpG-ODN concentration in the NP formulation was 1 mg/mL.

Another Biopolymer (C) Only NPs (C-NPs)

A low MW another biopolymer (C) based on viscosity and an ultra-low MW another biopolymer (C) were used.

1% w/v another biopolymer (C) solution was also used to develop another biopolymer (C)-CpG-ODN NPs, however uniform NP dispersion was not achieved.

The ultra-low MW another biopolymer (C) was formulated in the same manner, without overnight stir (5).

Another Biopolymer (C)—Gemini NPs (CG-NPs)

Stock solutions of another biopolymer (C) (low MW, Sigma) were prepared in 1% acetic acid. The stock solution of CpG-ODN (4 mg/mL in sterile water) was added to the gemini solution, swirled to mix and vortexed intermittently at room temperature. The complex was then bath sonicated 25 minutes at room temperature. (Table).

Sodium Alginate, Hyaluronic Acid NP Preparation

Stock solutions of sodium alginate and hyaluronic acid were prepared in sterile MilliQ water.

Sodium Alginate Particles

Sodium alginate solution was added to CpG-ODN solution and vortexed to mix evenly (A-NPs). For another biopolymer (C)-sodium alginate formulation (AC-NPs), ultra-low MW another biopolymer (C) solution was added at once and vortexed to mix until a uniform solution was observed (Table 7).

Sodium Alginate—Gemini Particles (AG-NPs)

Gemini—CpG-ODN complexes were first formed by adding CpG-ODN solution to gemini 12-3-12, 16-3-16, or 18-3-18 solutions and vortexing until a translucent uniform solution was observed. Appropriate volume of sodium alginate solution was added to the gemini—CpG-ODN complexes and vortexed to mix until uniform (Table 7).

Hyaluronic Acid-Another Biopolymer (C) Particles (HAC-NPs)

Appropriate volume of hyaluronic acid solution was added to CpG-ODN solution and vortexed. The corresponding volume of low MW another biopolymer (C) solution was added with intermittent vortexing. The solution was bath sonicated at 40° C. for 10 minutes until translucent and uniform (Table 8).

Example 3

Assessment of Particle Size, Polydispersity and Zeta Potential

Size (hydrodynamic diameter), polydispersity index and zeta (ζ) potential measurements were carried out on all particle formulations. Aliquots of 100 μL and 1000 μL of each formulation were prepared for size and zeta potential measurements, respectively. Measurements were performed using the Nano ZS Zetasizer (Malvern Instruments, Worcestershire, UK) which measures the hydrodynamic diameter of particles using dynamic light scattering (DLS). Measurements were carried out in triplicates for each condition. Z-average values as expression of mean particle size are considered valid for samples with a PDI index <0.5 (according to manufacturer's protocol).

Example 4

Materials and Methods

Animal Housing and Maintenance:

This work was approved by the Animal Research Ethics Board, University of Saskatchewan and adhered to the guidelines of the Canadian Council on Animal Care. Day-old broiler chickens or broiler hatching eggs were obtained from commercial hatcheries in Saskatchewan or British Columbia, Canada. Eggs were incubated at the Animal Care Unit (ACU) at the Western College of Veterinary Medicine, University of Saskatchewan. Groups of chicks were allocated randomly into animal isolation rooms at the ACU. Water and commercial broiler ration were provided ad libitum. Air from each room was exhausted through a HEPA filter and non-recirculated intake air was provided at a rate of 15-20 air changes/h. Air pressure differentials and strict sanitation was maintained in this isolation facility. Broilers were raised at 32° C. for the first week of life; thereafter the temperature was decreased 0.5° C. per day until a room temperature of 27.5° C. was reached. Light was provided for 24 h/d during days 0 to 2 post-hatch. Darkness was introduced at 3 d post-hatch with 1 h of dark added daily until 4 h of darkness was achieved.

*E. coli* Culture and Animal Model:

A field isolate of *E. coli* from a turkey with septicemia was used as the challenge strain. Briefly, one colony of *E. coli* was added to 100 ml of Luria broth (Difco LB broth, Miller, Becton Dickinson and Company; Sparks, MD, USA) in a 250 ml Erlenmeyer flask. The culture was grown at 37° C. for 16-18 h, shaking at 150 rpm. This stationary phase culture contained approximately 1x109 colony forming units (cfu) of bacteria per ml which was then further diluted into saline to the concentration of bacteria required to challenge birds. The *E. coli* challenge dose was confirmed by plating serial dilutions of the diluted culture in duplicate on 5% Columbia sheep blood agar plates, incubating for 18 h at 37° C. then counting the number of colonies. Briefly, birds were challenged with either 1×104 or 1×105 cfu of *E. coli* by the subcutaneous route in the neck. Two doses of *E. coli* were given to groups of birds to simulate field conditions since all birds in a commercial poultry barn will not be exposed to a consistent dose of *E. coli*. Birds were evaluated three times daily at the critical stage (until 3 d post-challenge) and twice thereafter for 7 d post-challenge. Each bird was observed for clinical signs and a daily clinical score was assigned: 0=normal; 0.5=slightly abnormal appearance, slow to move; 1=depressed, reluctant to move; 1.5=reluctant to move, may take a drink and peck some; 2=unable to stand or reach for food or water; and 3=found dead. Birds that received a clinical score of 2 were euthanized by cervical dislocation. At the end of the trial, each bird was given a cumulative clinical score (CCS) as a sum of daily clinical scores. Chicks that were found dead or euthanized were necropsied immediately. On day 7 post-challenge, the remaining birds were euthanized by cervical dislocation. Bacterial swabs were taken from the air sacs of dead and euthanized birds and cultured on 5% Columbia sheep blood agar according to the quadrant streaking technique. A semi quantitative estimate of *E. coli* isolation was conducted according to the growth on blood agar. Growth on these plates was recorded on a scale from 0 to 4+, where 0=no growth; few=less than 5 colonies; 1+=growth of bacteria on area 1; 2+=growth of the bacteria on areas 1 and 2; 3+=growth of bacteria on areas 1, 2, and 3; and 4+=growth of bacteria on areas 1, 2, 3, and 4.

CpG-ODN and Intrapulmonary (IPL) Delivery:

The CpG-ODN was free of endotoxin and produced with a phosphorothioate backbone (Operon Biotechnologies, Inc; Huntsville, AL, USA). Synthetic CpG-ODN was diluted in sterile, non-pyrogenic saline. CpG-ODN was delivered by IPL route, CpG-ODN was aerosolized as micro-droplets (particle size of 0.5-5 μm) using a Compressor Nebulizer (705-470) unit (AMG Medical Inc; Montreal, QC, Canada). Three doses (4 mg or 2 mg or 0.4 mg/chamber) of CpG-ODN were aerosolized in a closed 0.036 $m^3$ acrylic chamber for 15 or 30 min. The control group of birds was aerosolized with saline for 30 min in the acrylic chamber using the Compressor Nebulizer. The temperature was maintained at 28-30° C. in the acrylic chamber during administration of CpG-ODN or saline.

Formulations Comprising CpG-ODN Used

F1-PU-CpG12P: CpG-ODN with PVP

F2-PU-CpG12M: CpG-ODN with CMCNa

F3-PU-CpG-12P: CpG-ODN with PVP and NBC-PC as fluorescent marker [

F4-PU-CpG-12nP: CpG-ODN without PVP and NBC-PC as fluorescent marker

CpG-ODN (non-formulated)

Saline

Gemini-PVP-CpG-ODN complexes

The formulations were prepared in the following manner for example.

Step 1: Aqueous Phase

The CpG solution was prepared by adding 5 mL sterile water for injection (WFI) to make a stock of 4 mg/mL.

The PVP (polyvinyl pyrrolidone) Lot 95264/4017 BDH solution was prepared as 100 mg/15 mL in sterile WFI The lipid phase was prepared by melting DPPC, gemini surfactant and PEG400 at 70° C. and intermittent vortexing until homogeneous and dissolved. Concentrations are presented in Table 9.

TABLE 9

| Concentrations | |
|---|---|
| Ingredient | Concentration in finished formulation |
| DPPC | 10 mg/mL (1% w/v) |
| Gemini surfactant* 12-3-12 | 2.2 mg/mL |
| PEG400 (Spectrum) Lot# VK0042 | 10 mg/mL |

*(weight ratio of 2.2:1 gemini:DNA)

Preparation of Gemini-PVP-Complex (GP) (without CpG):

Ingredients and amounts used in the preparation of GP are listed in Table 10.

TABLE 10

| Concentrations | |
|---|---|
| | 1 mL |
| Lipid phase | 22.2 mg |
| PVP solution in sterile water (100 mg/15 mL) | 730 μL |
| CMCNa solution in sterile water 100 mg/15 mL | 730 μL |

The CpG-ODN solution reconstituted original stock 4 mg/mL was added to the previously prepared GP

TABLE 11

| Ingredients for GP-NP and CpG-ODN complexation and amounts used | |
|---|---|
| | 1 mL |
| Lipid phase | 22.2 mg |
| PVP solution in sterile water (100 mg/15 mL) | 730 μL |
| CpG-ODN solution 4 mg/mL | 250 μL |

75 μL of GP was mixed with 25 μL of CpG solution (4 mg/mL) to make the formulation for testing vesicle formation Example 5

Immunoprotective Effects of CpG-ODN as Intrapulmonary Micro-Droplets Against *E. coli* Septicemia The experiment consisted of two experimental groups: (a) IPL CpG-ODN (4 mg/chamber) micro-droplets for 30 min at 1 d post-hatch (n=40) and; (b) IPL saline for 30 min at 1 d post-hatch (n=40). Both groups were challenged with either $1\times10^4$ (n=20) or $1\times10^5$ (n=20) cfu of *E. coli* at 3 d post-hatch (2-days post-IPL delivery). Birds were examined for clinical signs for 10 d post *E. coli* challenge. The clinical signs and bacterial isolations were recorded as described Example 4.

Figure 2:
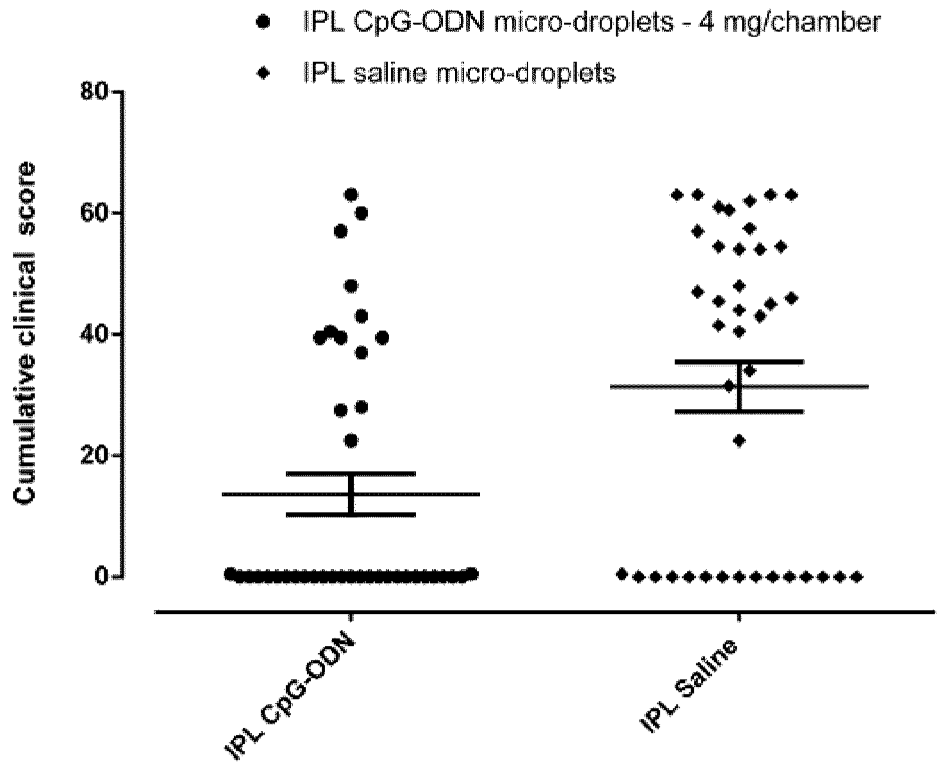
FIG. 2 shows the cumulative clinical score of neonatal broiler chickens following CpG-ODN micro-droplet treatment and *E. coli* challenge in Example 5.
Figure 3:
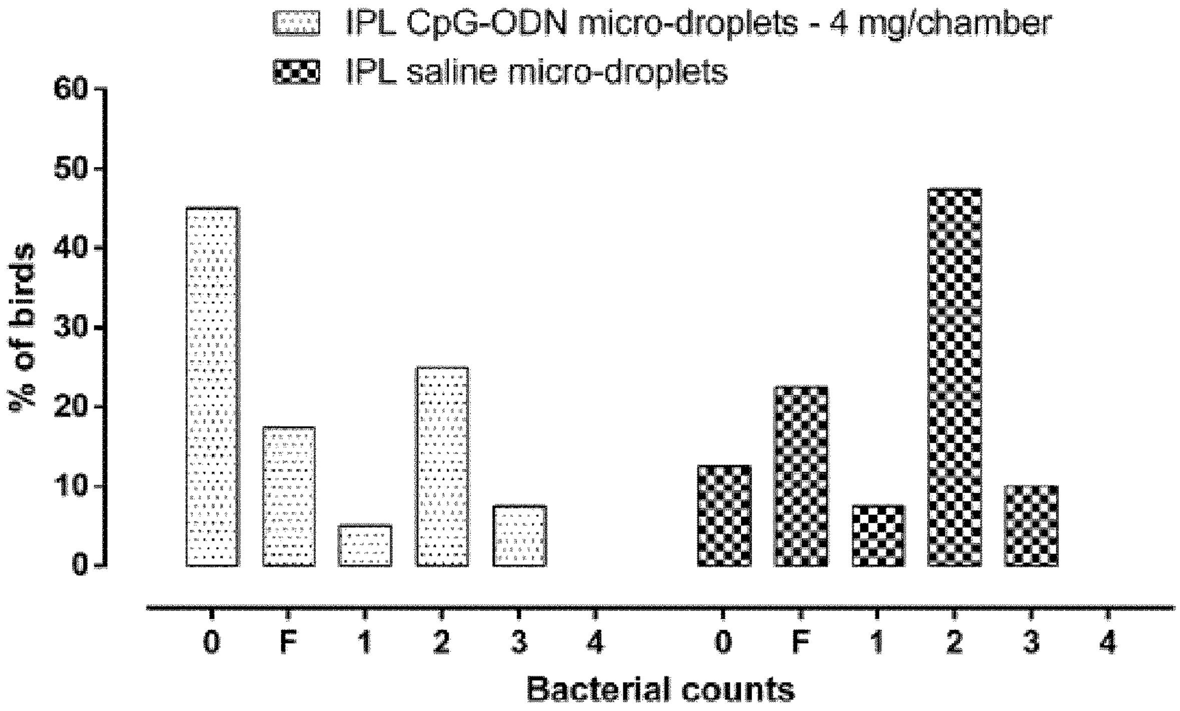
FIG. 3 shows the bacterial counts from bacterial isolations from air sacs of neonatal broiler chicken following CpG-ODN micro-droplet treatment and *E. coli* challenge in Example 5.

The results are shown in FIGS. 1-3. A significantly higher survival proportion in the IPL CpG-ODN as micro-droplets was noted when compared to the IPL saline as micro-droplets group (P<0.005) (FIG. 1). This group of birds experienced about half of the relative risk of mortality as did the birds that received saline (52%, P=0.0072). The groups that received IPL CpG-ODN as micro-droplets had significantly lower CCS (P<0.05) compared to IPL saline as micro-droplets (FIG. 2). Low counts of bacteria were isolated from the groups that received IPL CpG-ODN as micro-droplets compared to IPL saline (FIG. 3). These data clearly showed that CpG-ODN micro-droplets delivery by IPL route significantly protected neonatal chicks against *E. coli* septicemia.

Example 6

Exposure Time and Dose Titration of CpG-ODN in Neonatal Broiler Chickens for Intrapulmonary Micro-Droplets Delivery Experiments were performed to identify the exposure time of intrapulmonary CpG-ODN as micro-droplets required to obtain significant immunoprotection against *E. coli* septicemia. Three groups of 1 d post-hatch birds were used: (a) IPL CpG-ODN (4 mg/chamber) as micro-droplets for 15 min (n=40); (b) IPL CpG-ODN (4 mg/chamber) as micro-droplets for 30 min (n=40) and (c) IPL saline micro-droplets for 30 min (n=40). All groups were challenged with *E. coli* at 3 d post-administration of CpG-ODN with either $1\times10^4$ (n=20) or $1\times10^5$ (n=20) cfu of *E. coli*. The clinical signs and bacterial counts from air sacs were recorded as described above.

CpG-ODN was aerosolized using various doses, 4 mg/chamber or 2 mg/chamber or 0.4 mg/chamber, in closed 0.036 $m^3$ acrylic chamber. The objective of this experiment was to identify the minimum effective dose of CpG-ODN that could provide protection against *E. coli*. The experimental groups of 1 d post-hatch birds included: (a) IPL CpG-ODN as micro-droplets for 30 min using CpG-ODN 4 mg/chamber; (b) IPL CpG-ODN as micro-droplets for 30 min at a concentration of 2 mg/chamber; (c) IPL CpG-ODN as micro-droplets for 30 min using CpG-ODN 0.4 mg/chamber and (d) IPL saline micro-droplets for 30 min. All groups were challenged with *E. coli* at 3 d post-administration of CpG-ODN with either $1\times10^4$ (n=20) or $1\times10^5$ (n=20) cfu of *E. coli*. The clinical signs and bacterial counts from air sacs were recorded as described above.

Figure 4:
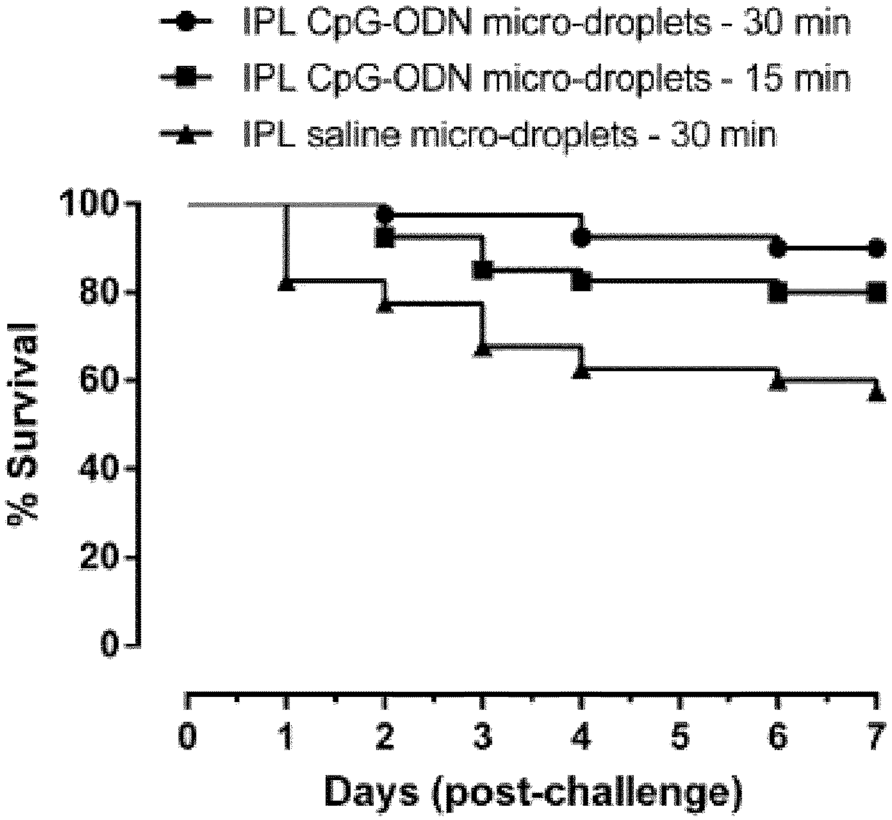
FIG. 4 shows the percent survival of birds treated with IPL CpG-ODN micro-droplets at different exposure time prior to a lethal *E. coli* challenge, as described in Example 6.
Figure 5:
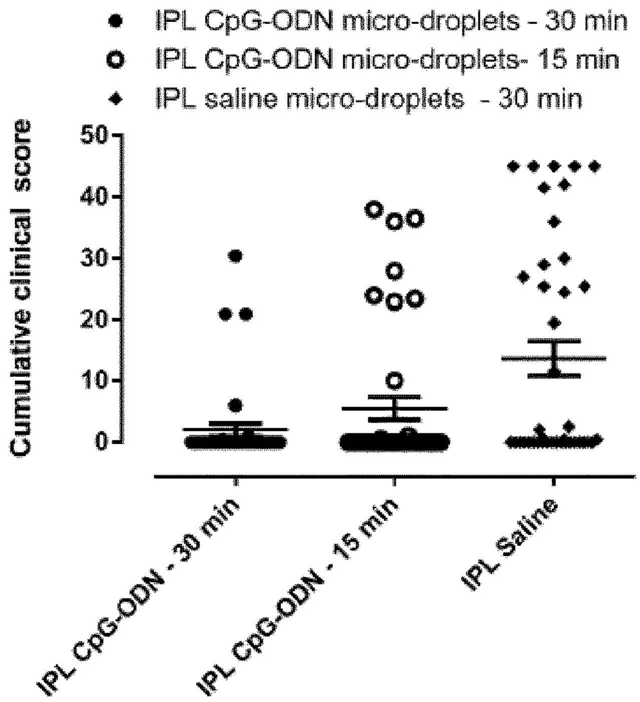
FIG. 5 shows the cumulative clinical score of birds treated with IPL CpG-ODN micro-droplets at different exposure time prior to a lethal *E. coli* challenge, as described in Example 6.
Figure 6:
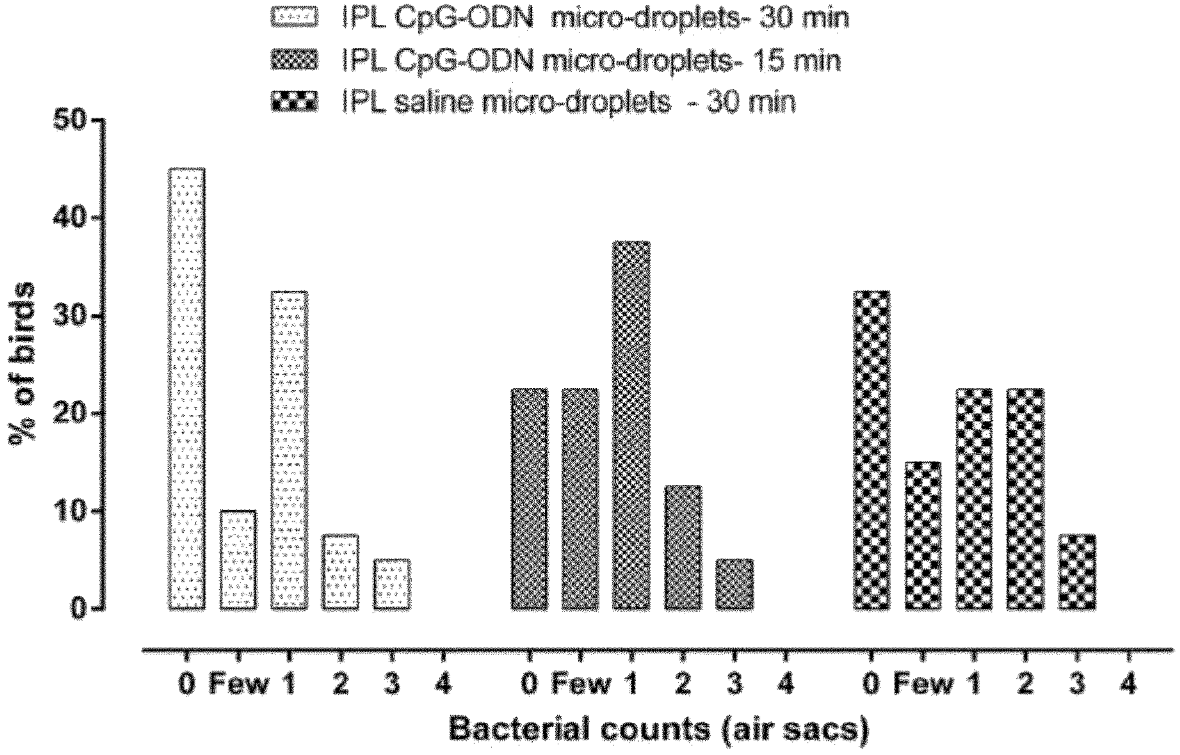
FIG. 6 shows percentage of birds with different bacterial counts score for neonatal broiler chicken following CpG-ODN micro-droplet treatment and *E. coli* challenge as described in Example 6. Scores 0 to 4 correspond to bacterial counts low to high.
Figure 7:
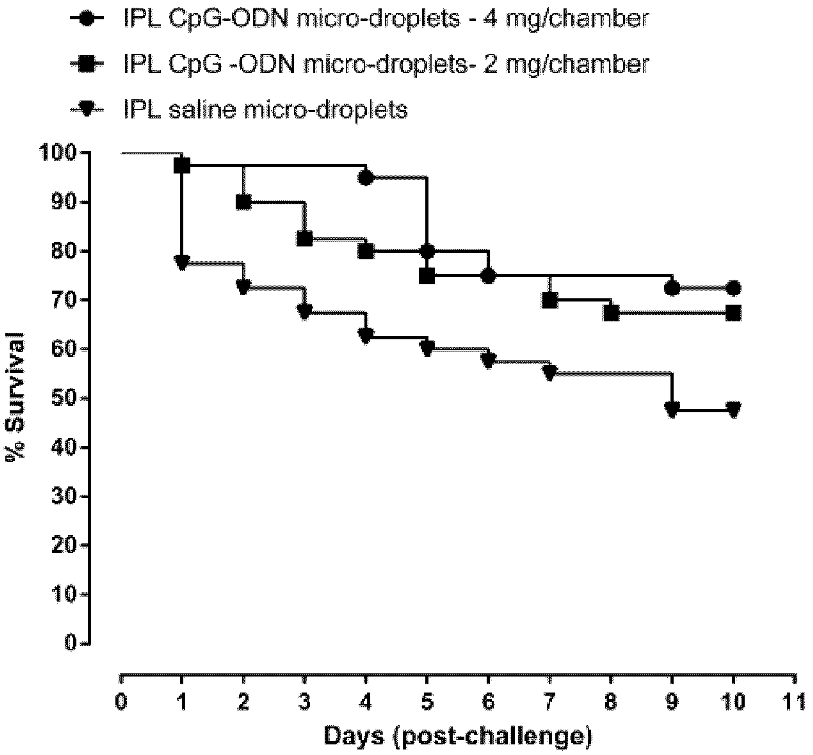
FIG. 7 shows percent survival rate of birds treated with IPL CpG-ODN micro-droplets at different doses (2 mg, 4 mg) prior to a lethal *E. coli* challenge, as described in Example 7.

The results are presented in FIGS. 4-7. Exposure of birds to IPL CpG-ODN as micro-droplets for 15 or 30 min showed significantly higher survivability compared to control group IPL saline (P<0.05) (FIG. 4). The birds that were exposed to 15 min of CpG-ODN by the IPL route experienced about half the relative risk of mortality (47%, P=0.029) compared to the IPL saline group. In this experiment, when the birds were exposed to CpG-ODN for 30 min by the IPL route, they experienced approximately a quarter of the relative risk of mortality (24%, P=0.001) as did the IPL saline control birds. Although birds that were given 30 min exposure to IPL CpG-ODN as micro-droplets had numerically better survival compared to those with 15 min of IPL CpG-ODN as micro-droplets, the difference was not statistically significant. The CCS of birds exposed to IPL CpG-ODN as micro-droplets at either 15 or 30 minutes was significantly lower compared to the IPL saline control group (P<0.05) (FIG. 5). More birds had lower bacterial counts in the group treated with IPL CpG-ODN as micro-droplets (FIG. 6) than in the other groups. Birds exposed to IPL CpG-ODN as micro-droplets at the concentration of 4 mg/chamber or 2 mg/chamber had significantly higher survival compared to the IPL saline as micro-droplet group (P<0.05) (FIG. 7). The clinical signs and bacterial counts in the 2 groups that received IPL CpG-ODN as micro-droplets were similar, which were significantly lower when compared to the IPL saline control group (P<0.05). Birds exposed to the concentration of 0.4 mg/chamber of IPL CpG-ODN as micro-droplets for 30 min were not protected from the *E. coli* challenge (P>0.05).

The results suggest that CpG-ODN exposure time, a correlate of dose, does influence the disease outcome. Overall, this experiment suggests that even 15 min exposure of chicks to CpG-ODN by IPL route can significantly provide protection against *E. coli* septicemia.

Example 7

Duration of Immunoprotective Effects of CpG-ODN as IPL Micro-Droplets Against *E. coli* Septicemia The objective of this experiment was to study the duration of immunoprotective effects of CpG-ODN following IPL micro-droplet delivery. Broiler chickens at 1 d post-hatch were randomly allocated into 10 groups (n=40). Of these 10 groups, 5 received IPL CpG-ODN (4 mg/chamber) as micro-droplets for 30 min while the other 5 groups received IPL saline as micro-droplets for 30 min. Within each group, birds were challenged with *E. coli* at $1\times10^4$ (n=20) or $1\times10^5$ (n=20) cfu subcutaneously in the neck at the following time points: (a) 6 h; (b) 1 d; (c) 3 d; (d) 5 d, and (e) 7 d post-administration of either IPL CpG-ODN or IPL saline as micro-droplets. The clinical signs and bacterial counts were recorded as described above.

Figure 8:
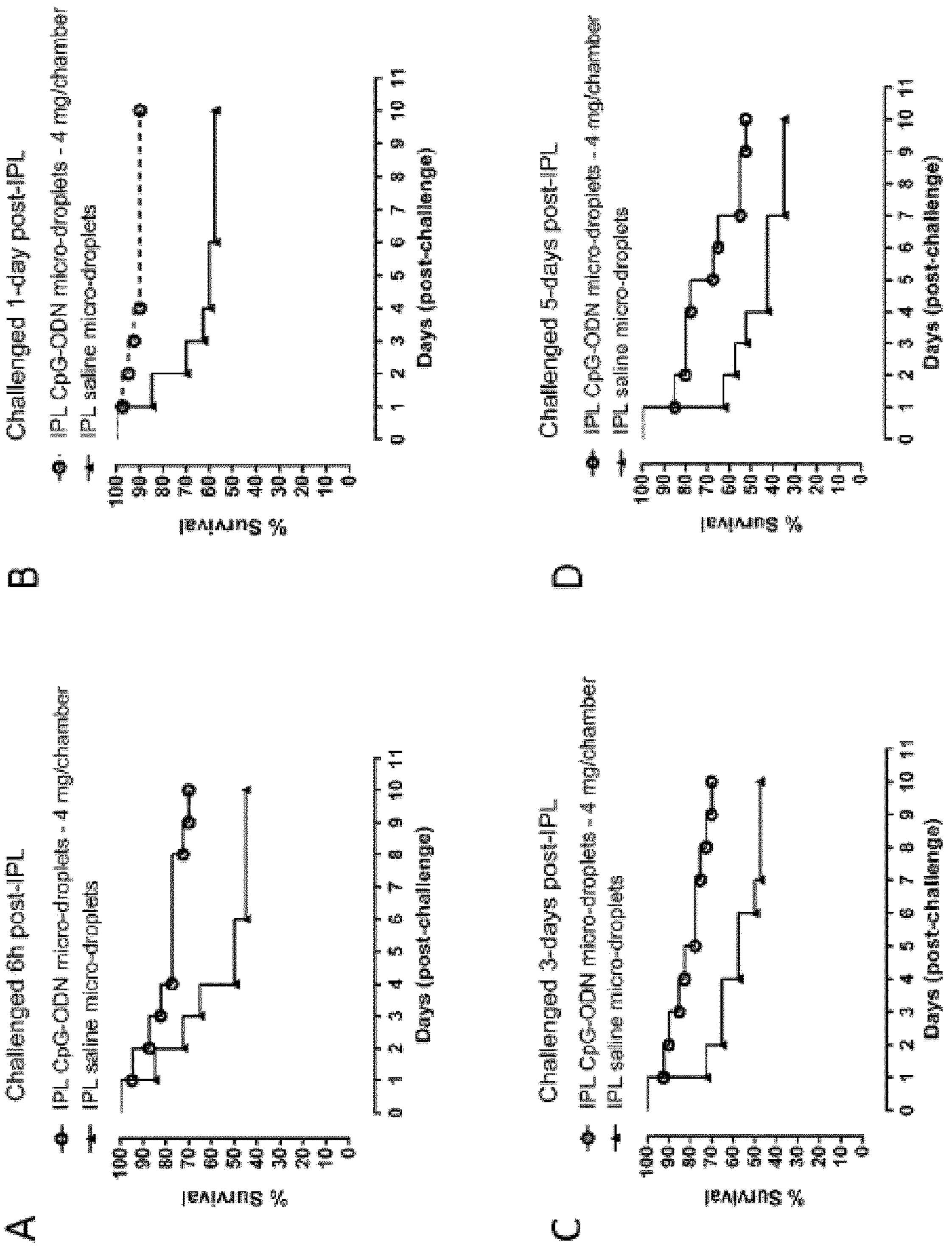
FIG. 8 shows percent survival of birds that were treated with IPL CpG-ODN micro-droplets at 4 mg/chamber, and then challenged with a lethal dose of *E. coli* at various time points post treatment (A: 6 h, B: 1 day, C: 3 days and D: 5 days) as described in Example 8.

The results are presented in FIG. 8. Groups that received IPL CpG-ODN as micro-droplets for 30 min showed significantly higher survival against *E. coli* challenge as early as 6 h (FIG. 8A) post-administration of CpG-ODN, and continued to have statistically significant protection until 5 d (FIG. 8D) post-administration, compared to the IPL saline control (P<0.05) (FIG. 8).

Example 8

Cellular Infiltration in the Lungs and Growth Rate of Broiler Chickens Following CpG-ODN IPL Micro-Droplet Delivery Two groups of broiler chickens at 1 d post hatch were exposed to (a) IPL CpG-ODN (4 mg/chamber) as micro-droplets for 30 min (n=40) or (b) IPL saline as micro-droplets for 30 min (n=40). All birds used for histopathology of lungs were raised in the same manner. In order to evaluate the pulmonary parenchyma at the microscopic level, sections of lungs were collected from 5 birds per group at 0, 3, 6, 12, 24, 48 and 72 h post-administration of IPL CpG-ODN. These samples were preserved in 10% neutral buffered formalin, embedded in paraffin, sectioned in 5 microns and stained with hematoxylin and eosin (H&E) using standard methods. Remaining birds (5 birds/group) were monitored for health and clinical signs and at 42 d, were euthanized. At the time of euthanasia, tissue samples (lung, liver, spleen, heart, bursa of Fabricius, thymus and muscle) were collected for histopathological examination. Body weight and bursal weight to body weight ratio (BBW) was calculated.

Figure 9:
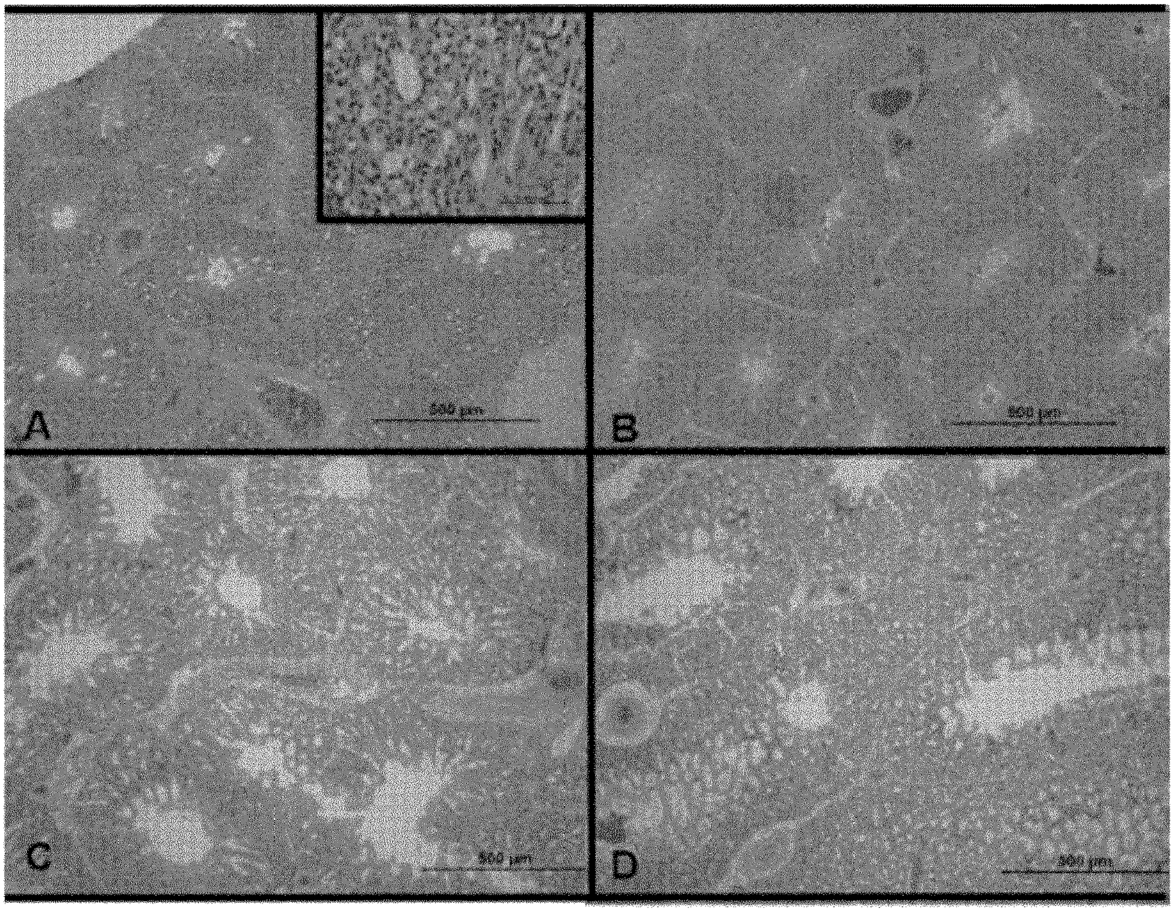
FIG. 9 shows microscopy images of lung tissues of birds treated with micro-droplets of IPL CpG-ODN or IPL saline at different time points post treatment (panel A=24 h with IPL CpG-ODN; panel B=72 h IPL CpG-ODN; panel C=24 h with IPL saline; panel D=72 h with IPL saline.

The results are presented in FIG. 9. Histopathological examination of the lungs revealed infiltration of inflammatory cells, predominantly mononuclear cells with occasional heterophils in the pulmonary parenchyma in groups treated with IPL CpG-ODN as micro-droplets at 24 h post-administration of CpG-ODN (FIG. 9). No microscopic changes were detected by histopathology in any of the organs (i.e. lungs, liver, spleen, heart, bursa, thymus and muscle) when they were examined 42 d following IPL CpG-ODN as micro-droplets. The BBW did not have a significant difference (P>0.05) between the IPL CpG-ODN as micro-droplet and IPL saline control groups. The average body weight of IPL CpG-ODN as micro-droplets was 2.39 kg (SD 353.7) while the IPL saline group was 2.37 kg (SD. 284.2) by the end of 42 d post-hatch. Total mortality was zero in both the IPL CpG-ODN and IPL saline control groups.

Example 9

Clinical scores of each bird for the 10 d period were summed to generate a CCS and the significance of differences among groups was tested using Kruskal Wallis non-parametric analysis of variance. The significance of difference in Survival analysis, bacteriological scoring and CCS were analyzed using Prism (Prism 5.0, GraphPad Software Inc; San Diego, CA, USA). The relative risks of mortality compared to control subjects were calculated using Fisher's exact test in Prism. The significance of differences among groups in survival patterns and median survival times were analyzed using the log-rank test and chi-square statistics.

Example 10

Testing the Nanoparticle Delivery Vehicle in a Chicken Macrophage Cell Model

CpG-ODN Uptake Assay in the HD11 Cell Line

Avian macrophages were used for an in vitro screening model of nanoparticle formulations prepared. HD11 chicken macrophages are a heterogeneous non-adherent cell population containing mainly round hybridoma like cells (HD11) and a small population of long fibroblast cells.

Cell Culture and Dose Application

HD11 cell culture: HD11 cells were cultured in T75 flasks with RPMI 1640 media with L-glutamine (basic media) (HyClone™, GE Healthcare Life Sciences, Logan, Utah) supplemented with 10% FBS and 1:1000 gentamicin (complete media). Cells were grown to confluency $5\times10^5$ cells/ml and passaged every 2 days.

Cell Dosing:

HD11 cells were re-suspended in RPMI 1640 media with L-glutamine (basic media). Cells were counted and seeded into a non-treated 96-well U-bottom plate at 30,000 cells per well and suspended in 250 μL basic media.

Cells were transfected in triplicate using a dose of 1 μg CpG-ODN per well (1 μL of formulation) and incubated at 37° C. for 2 hours in basic media. After 12-hour incubation, supernatants were transferred to a 96-well clear bottom plate pre-filled with 130 μL sterile water for the Greiss assay. Three hundred μL of complete media was added to each well, the cells were re-suspended, and incubated further for 12 hours.

At the end of the second 12-hour incubation (total=24 hours) supernatant from each well was collected and transferred to a clear bottom glass 96-well plate with each well pre-filled with 130 μL sterile water for the Greiss assay.

Cells were re-suspended in PBS mixed with either MitoTracker™ Green FM (Life Technologies), cell viability stain for flow cytometry.

Fluorescence Flow Cytometry

The CpG-ODN NP uptake and toxicity of various prepared NPs were assessed using the Attune® Acoustic Focusing Flow Cytometer (Applied Biosystems, Life Technologies, Carlsbad, California, USA). The CpG-ODN uptake was calculated based on the percentage of viable cells that exhibited a fluorescence signal above the threshold signal. The threshold value was determined based on the background fluorescence of untreated cells.

Statistical analysis was performed using the GraphPad Prism software (GraphPad Software, La Jolla, CA, USA). Two-way ANOVA in conjunction with Tukey post hoc tests were used to analyze CpG-uptake for multi-variable analysis.

Assessment of NP's Toxicity in HD11 Cells

Cell viability after stimulation with different CpG-ODN NP formulations was assessed by measuring viability fluorescence following treatment with MitoTracker™ Green FM.

Assessment of Immune Activation in HD11 Cells: Greiss Assay

Nitrite concentration produced by cells treated with the various NP formulations was measured in triplicate using the standard Greiss Assay Kit (Life Technologies). Absorbance at 548 nm was read using a microplate reader and nitrite concentration was assessed using a nitrite standard curve (1-100 μM).

Statistical analysis was performed using the GraphPad Prism software (GraphPad Software, La Jolla, CA, USA). Two-way ANOVA in conjunction with Tukey post hoc tests were used to analyze nitrite production for multi-variable analysis. A p-value of less than 0.05 was considered as statistically significant.

Localization of CpG-ODN During Immune Stimulation: Confocal Imaging

Selected formulations were chosen for further study including confocal imaging and testing formulation stability after nebulization.

To determine localization of DNA upon transfection of HD11 macrophages at the cellular level, fluorescence imaging of Alexa Fluor 647 CpG-ODN was performed using the Zeiss 710 CLSM (Carl Zeiss, Oberkochen, Germany). Uptake of CpG-ODN NPs were imaged after 2 and 24 hours post stimulation containing labeled CpG-ODN with Alexa Fluor 647 only.

Nebulization Model for Testing Formulation Stability and Functionality

Selected NP formulations were nebulized using the Med-Pro Compressor Nebulizer (AMG Medical Inc., Montreal, Quebec, Canada). The formulation was nebulized for 2 minutes. The nebulizer was turned off and the nebulized formulation was collected from the glass vial and the medication holder. Analysis of nebulized formulations was performed using DLS for measuring size and potential.

Assessing Delivery and Effectiveness of CpG-ODN Nanoparticles in a Live Chick Model The purpose of this experiment was to investigate biodistribution patterns and the improvement in protection of CpG-ODN against *E. coli* challenge resulting from NP formulations in 1-day old chicks.

Animals and In Vivo Experimental Design

Neonatal 1-day old broiler chicks were randomly assigned to different experimental groups: I) saline negative control (2 chicks), II) chicks nebulized with naked CpG-ODN (5 animals for biodistribution assessment, 40 birds for *E. coli* challenge protection), III) chicks nebulized with selected CpG-ODN formulations (5 animals for biodistribution assessment, 40 birds for *E. coli* challenge protection).

CpG-ODN NPs Preparation for Biodistribution and Protection Assessment

Selected formulations for protection assessment were prepared as previously mentioned in Example 2. For formulations for assessing biodistribution, CpG-ODN containing 12.5% of CpG-ODN labeled with Alexa Fluor 647 was used as a tag to identify distribution within the respiratory tract. Additionally, the particles themselves were also labeled with 5% fluorescent lipid: Oregon Green™ 488 1,2-dihexadecanoyl-sn-Glycero-3-phosphoethanolamine (DHPE) Lipid (Life Technologies) or 1-palmitoyl-2-{6-[(7-nitro-2-1,3-benzoxadiazol-4-yl)amino]hexanoyl}-sn-glycero-3-phosphocholine (NBD-PC) lipid (Avanti Polar Lipids Inc.) for gemini-phospholipid formulations. For formulations containing another biopolymer (C), 2% of fluorescent Fluorescein isothiocyanate (FITC)-another biopolymer (C) was used as a tag. The formulations were prepared so that chicks were nebulized with a dose of 100 μL of formulation containing 100 μg CpG-ODN per chick.

Experimental Design for In Vivo Pulmonary Delivery of NP Formulations

On the day of hatch, formulation doses were administered by nebulization (Med-Pro Compressor Nebulizer) to commercial 1-day old broiler chicks in a nebulization chamber (FIG. 10).

Groups of 1-day old commercial broiler chicks were nebulized in an acrylic chamber for 15 minutes with a dose of 100 μg/100 μL per chick. Chicks nebulized with fluorescent formulations were sacrificed at 2 and 24 hours post nebulization.

For the biodistribution assessment, chicks were euthanized at 2 hours (n=5) and 24 hours (n=5) post nebulization. The respiratory organs were harvested at each time point for each formulation. The trachea, syrinx, and lung respiratory organs were isolated and snap frozen in optimal cutting temperature (OCT) compound (Thermo scientific, Waltham, MA, USA), ensuring right orientation for longitudinal lung sections after harvesting. Tissues were stored at −80° C. until they were sectioned. 80 μm tissue sections were sectioned with a cryo-stat and observed by CLSM at appropriate excitation and emission wavelengths for Alexa Fluor 647, NBD-PC, Oregon Green 488 and FITC to determine localization of NP and CpG-ODN within the chick respiratory tract.

In Vivo Protection Experiments in 1-Day Old Chicks

For protection studies against lethal *E. coli* infection, non-fluorescent formulations were administered to chicks on the day of hatch (n=40 per group). The chicks were challenged with *E. coli* at 2 days after immunization and another group at 5 days after immunization for each formulation. Chicks were monitored and evaluated for clinical signs of *E. coli* infection and survival after challenge and sections from euthanized birds were sectioned for histopathological analysis.

Results

Nanoparticle Characterization

Particle Characterization by Zetasizer

Particle size for all formulations was measured and reported as Z-average diameter (n=3).

Effect of Biopolymer and Other Excipients on the Size and Zeta Potential of $G_{12}$L-NPs and $BG_{12}$L-NPs The size range of all $G_{12}$L-NP particles, including biopolymer coated $G_{12}$L-NPs ($BG_{12}$L-NPs) complexed with CpG-ODN ranged generally from 160-250 nm although some were larger. This represents a large increase in size from vesicles un-complexed with CpG-ODN that were under 20 nm in size. The one exception is the $BG_{12}$L-NP formulated with CMCNa which decreased in size upon complexation with CpG-ODN in PEG 400 excipient. However, due to a high polydispersity index >0.5, the average diameter of the vesicles is not representative of the particle population. The effect of changing the excipient from PEG400 to PG to form gemini phospholipid vesicles decreases the size of $G_{12}$L-NPs and $BG_{12}$L-NPs blank particles. Although the change in size is limited to a maximum of 4 nm difference.

The addition of a biopolymer coating to $G_{12}$L-NPs did not have a significant effect on the size of the particles formulated in both PEG 400 and PG excipients. All formulations with the exception of those formulated with PVP Kollidon 25 and CMCNa polymers had a PDI of ~0.2, indicating that the size distribution of particles within the formulation was relatively uniform.

TABLE 12

Z-average hydrodynamic diameter and PDI measurements of gemini 12-3-12 phospholipid particles with and without CpG-ODN complexation*

| Formulation | Measurement | PEG 400 blank particles | PEG400 Final Formulation | PG blank particles | PG Final Formulation |
|---|---|---|---|---|---|
| $G_{12}$L-NP | Size (nm) ± S.D. | 11.2 ± 0.1 | 161.7 ± 15.8 | 9.9 ± 0.1 | 194.9 ± 8.4 |
| n = 3 | PDI ± S.D. | 0.258 ± 0.003 | 0.211 ± 0.005 | 0.186 ± 0.022 | 0.185 ± 0.019 |
| PVP 10,000 | Size (nm) ± S.D. | 12.5 ± 0.1 | 173.0 ± 1.5 | 11.6 ± 0.3 | 177.1 ± 22.3 |

TABLE 12-continued

Z-average hydrodynamic diameter and PDI measurements of gemini 12-3-12 phospholipid particles with and without CpG-ODN complexation*

| Formulation | Measurement | PEG 400 blank particles | PEG400 Final Formulation | PG blank particles | PG Final Formulation |
|---|---|---|---|---|---|
| $BG_{12}$L-NP n = 3 | PDI ± S.D. | 0.171 ± 0.006 | 0.256 ± 0.013 | 0.150 ± 0.014 | 0.703 ± 0.035 |
| PVP Kollidon25 | Size (nm) ± S.D. | 17.5 ± 0.2 | 250.2 ± 85.3 | 13.4 ± 0.3 | 177.9 ± 8.8 |
| $BG_{12}$L-NP n = 3 | PDI ± S.D. | 0.154 ± 0.006 | 0.620 ± 0.077 | 0.198 ± 0.003 | 0.236 ± 0.031 |
| PVP40000 | Size (nm) ± S.D. | 14.2 ± 0.2 | 172.5 ± 4.4 | 12.4 ± 0.2 | 213.2 ± 16.6 |
| $BG_{12}$L-NP n = 3 | PDI ± S.D. | 0.183 ± 0.008 | 0.178 ± 0.01 | 0.202 ± 0.007 | 0.225 ± 0.031 |
| CMCNa | Size (nm) ± S.D. | 616.4 ± 170.8 | 174.7 ± 9.0 | 1.3 ± 1.5 | 139.8 ± 5.5 |
| $BG_{12}$L-NP n = 3 | PDI ± S.D. | 0.705 ± 0.018 | 0.226 ± 0.020 | 0.775 ± 0.043 | 0.236 ± 0.024 |

Upon complexation with CpG-ODN, the zeta potential of the original particles decreases indicating complexation with negatively charged CpG-ODN DNA. The zeta potential of the $G_{12}$L-NP (+53.2 mV) is the highest in comparison to all other formulated $BG_{12}$L-NPs, and relatively similar to uncomplexed $G_{12}$L-NP. Overall, the zeta potential of final formulations in PEG400 excipient is higher than those formulated with PG. This is most evident for the $G_{12}$L-NP and PVP 10,000 $BG_{12}$L-NP.

TABLE 13

ζ potential measurements of empty gemini 12-3-12 phospholipid and CpG-ODN complexed with different biopolymers using PEG400 excipient or PG excipient
Mean ζ potential (mV) ± S.D.

| | PEG 400 | | PG | |
|---|---|---|---|---|
| Formulation code | Gemini-phospholipid vesicles | Final formulation (with CpG) | Gemini-phospholipid vesicles | Final formulation (with CpG) |
| $G_{12}$L-NP | +48.1 ± 11.6 | +53.2 ± 1.0 | +32.8 ± 5.8 | +35.7 ± 0.2 |
| PVP 10,000 $BG_{12}$L-NP | +33.1 ± 15.7 | +42.8 ± 0.4 | +39.8 ± 1.6 | +28.9 ± 0.9 |
| PVP Kollidon 25 $BG_{12}$L-NP | +29.8 ± 6.0 | +23.8 ± 1.6 | +36.9 ± 3.4 | +22.1 ± 2.7 |
| PVT 40,000 $BG_{12}$L-NP | +63.2 ± 3.6 | +34.4 ± 1.2 | +39.4 ± 3.3 | +31.8 ± 4.0 |
| CMCNa $BG_{12}$L-NP | +41.0 ± 12.3 | +36.4 ± 2.5 | +38.8 ± 0.2 | +33.7 ± 0.9 |

* pH range of 6.6-7 corresponds to pH of formulation at the time of zeta potential measurement
Values expressed as mean ± S.D.;
n = 3

Gemini Nanoparticle Characterization (G-NPs)

The sizes of complexes formed with first generation gemini surfactant with three different tail lengths (12,16,18). The average diameter of G-NPs increased proportionally from 175.2 nm, 290.5 nm, to 1429 nm corresponding with increasing tail length from 12, 16, 18 respectively.

TABLE 14

Z-Average hydrodynamic diameter and PDI measurements of three different gemini-CpG-ODN complexes and gemini micelles

| Sample | Formulation Code | Measurement | Gemini micelles | Final Formulation (with CpG-ODN) |
|---|---|---|---|---|
| gemini 12-3-12 | $G_{12}$-NP | Size (nm) ± S.D. | 298.4 ± 164.1 | 175.2 ± 2.6 |
| | | PDI ± S.D. | 0.446 ± 0.087 | 0.249 ± 0.016 |
| gemini 16-3-16 | $G_{16}$-NP | Size (nm) ± S.D. | 86.8 ± 4.1 | 290.5 ± 8.2 |
| | | PDI + S.D. | 0.555 ± 0.128 | 0.299 ± 0.021 |

TABLE 14-continued

Z-Average hydrodynamic diameter and PDI measurements of three different gemini-CpG-ODN complexes and gemini micelles

| Sample | Formulation Code | Measurement | Gemini micelles | Final Formulation (with CpG-ODN) |
|---|---|---|---|---|
| gemini 18-3-18 | $G_{18}$-NP | Size (nm) ± S.D. | 292.2 ± 26.1 | 1429 ± 219.2 |
| | | PDI ± S.D. | 0.560 ± 0.063 | 0.954 ± 0.056 |

Values expressed as mean ± S.D.;
n = 3

Complexation of CpG-ODN with gemini surfactant resulted in the formation of stable particles. All had a zeta potential above the +30 mV threshold. The zeta potential increased with longer gemini tail length with gemini 18-3-18 having the highest zeta potential corresponding to +54.9 mV. Additionally, gemini surfactant micelles also exhibited >+30 mV zeta potential indicating the colloidal stability of the gemini aggregates.

Substitution of the cationic gemini component from GL-NPs for another cationic biopolymer (C) in CL-NPs resulted in an increase of particle size distribution from ~160 nm to 1060.9 nm the zeta potential of the CL-NP was less than +30 mV at +12.7 mV Particle Reproducibility The preparation method for each particle was evaluated by determining batch to batch differences in NP hydrodynamic diameter. The preparation of blank $G_{12}$L-NP and $BG_{12}$L-NP vesicles in both PEG400 and PG excipients were very reproducible, giving similar sizes at each separate preparation. PVP Kollidon 25 and CMCNa $BG_{12}$L-NPs produced variable sizes for each preparation. Upon complexation with CpG-ODN, PEG400 excipient resulted in more consistent NP formulation than PG. Variability of PVP Kollidon 25 and CMCNa $BG_{12}$L-NPs also translated into the final formulation and $G_{12}$L-NP and PVP 10,000 $BG_{12}$L-NP generated the most consistent formulations.

$G_{12}$-NPs produced the most consistent particles from batch to batch and was more consistent than the s CG-NPs were more variable batch to batch Particle Size Stability of $G_{12}$L-NPs and $BG_{12}$L-NPs Size distribution of blank GL-NPs was monitored over 30 days of storage at 4° C. to identify changes in NP size, aggregation and sedimentation. Blank $G_{12}$L-NPs and $BG_{12}$L-NPs showed a similar size distribution throughout the 30-day period. The only exception was the blank $BG_{12}$L-NP formulated with biopolymer PVP Kollidon 25 and PEG 400 excipient, which showed variable particle size and aggregation by day 15 of storage at 4° C.

Upon complexation with CpG-ODN, the particle size over the 30-day period was more variable especially with the NPs formulated in PEG400 excipient. The change in size ranged from 200 nm to 350 nm by the end of the 30-day period. Of the PEG 400 formulations, PVP 10,000 $BG_{12}$L-NP aggregated the least ranging from 200 nm at day 1 to 280 nm by day 30. The NPs formulated with PG showed similar size over the 30-day period.

The PDI over the 30-day storage period was measured. The blank $G_{12}$-NPs and $BG_{12}$-NPs had more uniform PDIs and only PVP Kollidon 25 $BG_{12}$-NP in PEG 400 had variable polydispersity over the time period. Final formulations had more variable polydispersity and were above the 0.5 threshold of the Zetasizer by day 15.

Particle Characterization by FCS

Assessing NPs as an Effective CpG-ODN Delivery Vehicle in HD11 Chicken Macrophage Cells HD11 cells were incubated with varying quantities of free or naked CpG-ODN for varying time points ranging from 1-4 hours. The percentage of cells with CpG-ODN uptake as detected by the Alexa Fluor 647 fluorescent label was determined at the end of each stimulation time point. Cellular uptake was dose and time dependent between 0.1-20 μg of CpG-ODN, reaching 50% uptake at 20 μg dose after 4 hours of stimulation. Dosing cells for 4 hours was chosen for preliminary NP uptake experiments.

Figure 11:
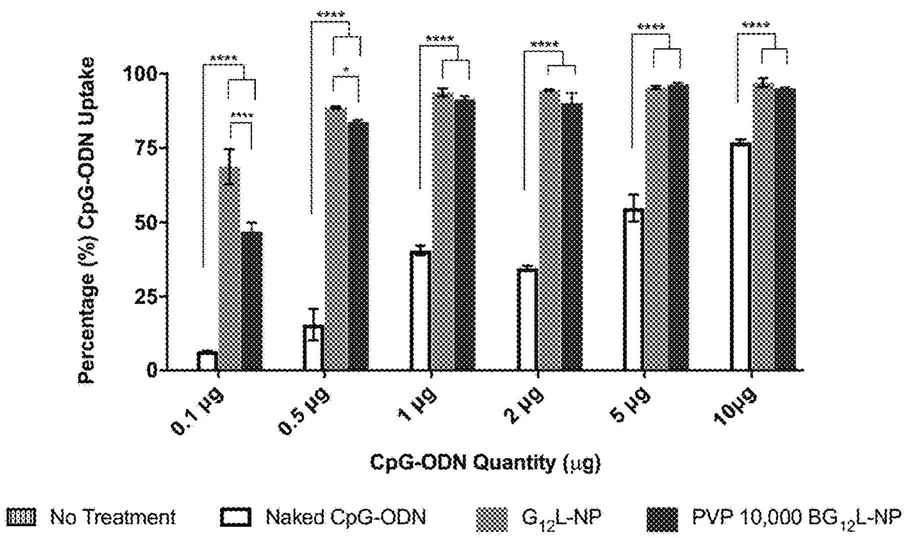
FIG. 11 shows assessment of CpG-ODN uptake after 4 hours dosing associated with $G_{12}$LP-NPs and $BG_{12}$LP-NPs in comparison to naked CpG-ODN.

Evaluating the Capacity of $G_{12}$L-NPs and $BG_{12}$L-NPs to Improve Uptake of CpG-ODN in HD11 Chicken Macrophages To determine whether $G_{12}$L-NPs and $BG_{12}$L-NPs could enhance CpG-ODN uptake in comparison to naked CpG-ODN, HD11 macrophages were stimulated with increasing doses of CpG-ODN NPs and naked CpG-ODN for 4 hours. After 4 hours of dosing, $G_{12}$L-NPs and PVP 10,000 $BG_{12}$L-NPs were able to significantly increase the number of HD11 macrophages containing CpG-ODN in comparison to naked CpG-ODN (FIG. 11). In fact, it only took the equivalent of 0.5 μg of both CpG-ODN NPs to reach near 100% cell uptake. Conversely, it took 5 μg of naked CpG-ODN to reach 50% uptake and 10 μg of naked CpG-ODN to reach a comparable level of uptake associated with $G_{12}$L-NPs and $BG_{12}$L-NPs. The PVP 10,000 biopolymer component of the $BG_{12}$L-NP performed similar to the $G_{12}$L-NP without biopolymer also reaching near 100% cell uptake at 1 μg CpG-ODN dose.

HD11 cells were incubated with CpG-ODN formulations in RPMI 1640 media for 4 hours and % CpG-ODN uptake was measured immediately after incubation, n=3. Error bars represent mean±S.D. Statistically significant differences between experimental groups were determined by two-way ANOVA with Tukey's multiple comparison test. Statistics were performed between naked CpG-ODN and formulations at each dose where * $p<0.05$, **** $p<0.0001$.

The extent of CpG-ODN uptake in cells dosed with NP formulations for different amounts of time over 4 hours was also tested.

Figure 12:
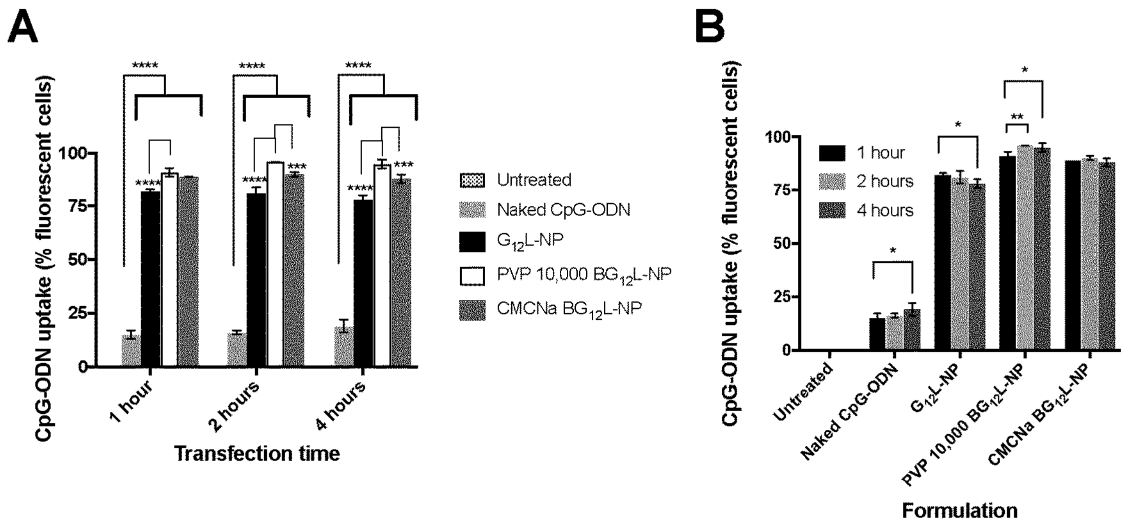
FIG. 12 shows Time dependent uptake of CpG-ODN after dosing with $G_{12}$L-NPs and $BG_{12}$L-NPs in comparison to naked CpG-ODN DNA.

One μg CpG-ODN was used for dosing cells at each time point and was evaluated. CpG-ODN uptake was detectable at all dosing times from 1-4 hours (FIG. 12A). Like the previous experiment, all formulations again significantly improved uptake of CpG-ODN in HD11 cells at all time points compared to stimulation with naked CpG-ODN (FIG. 12A). Additionally, the PVP 10,000 $BG_{12}$L-NP formulation in this experiment produced more uptake at all time points than the $G_{12}$L-NP formulation without biopolymer. It also performed better in comparison to CMCNa $BG_{12}$L-NP after 2 and 4 hours of dosing. Time of dosing had a minimal effect on uptake and was mainly evident comparing dosing of 1 and 4 hours (FIG. 12B). CpG-ODN uptake was measured immediately after dosing (n=3). The same data is transposed in B to outline changes in CpG-ODN uptake resulting from the increase of dosing time. Error bars represent mean±S.D. Statistically significant differences between experimental groups were determined by two-way ANOVA with Tukey's multiple comparison test. Statistics were performed between naked CpG-ODN and formulations at each dose where * $p<0.05$,  $p<0.001$, * $p=0.001$ **** $p<0.0001$.

Evaluating the Capacity of $G_{12}L$-NPs and $BG_{12}L$-NPs to Improve CpG-ODN Retention in HD11 Macrophages The retention of CpG-ODN 24 hours post dosing with $G_{12}L$-NPs and $BG_{12}L$-NPs was also evaluated in HD11 cells. Retention, refers to whether CpG-ODN can still be detected 24 hours later in cells after the initial dosing for 2 hours.

New $G_{12}L$-NP and $BG_{12}L$-NP formulations using 4 different biopolymers of different molecular weights (PVP 10,000; PVP Kollidon 25; PVP 40,000, CMCNa), formulated in 2 different excipients (PEG 400, PG) were tested for their ability to retain CpG-ODN within cells. All $G_{12}L$-NPs and $BG_{12}L$-NPs resulted in significantly higher retention of CpG-ODN uptake 24 hours after initial dosing for 2 hours in comparison to naked CpG-ODN, ≥30% versus 10%, respectively. The PVP 10,000 $BG_{12}L$-NP formulation which has the lowest MW of the polymers, resulted in the highest retention of CpG-ODN uptake in comparison to the other formulations. PVP 10,000 $BG_{12}L$-NP formulated in PEG 400 did perform significantly better than PVP Kollidon 25 $BG_{12}L$-NP in PEG 400 and the $G_{12}L$-NP in PG. PVP 10,000 $BG_{12}L$-NP resulted in similar CpG-ODN uptake in comparison to $G_{12}L$-NP without biopolymer. Using PEG400 versus PG excipient did not significantly affect the retention of CpG-ODN in the different formulations.

Assessment of HD11 Cell Toxicity after CpG-ODN NP Stimulation

Viability in HD11 Cells after Naked CpG-ODN Stimulation

The viability of HD11 cells after naked CpG-ODN stimulation was compared to HD11 cells stimulated with CpG-ODN NPs. The viability of HD11 cells remained above 90% after 1, 2, and 4 hours of stimulation across all CpG-ODN quantities.

Cell Viability and Mitochondrial Activity after NP Transfection

Gemini 12-3-12 Phospholipid Formulations Maintain High Mitochondrial Activity

Figure 13:
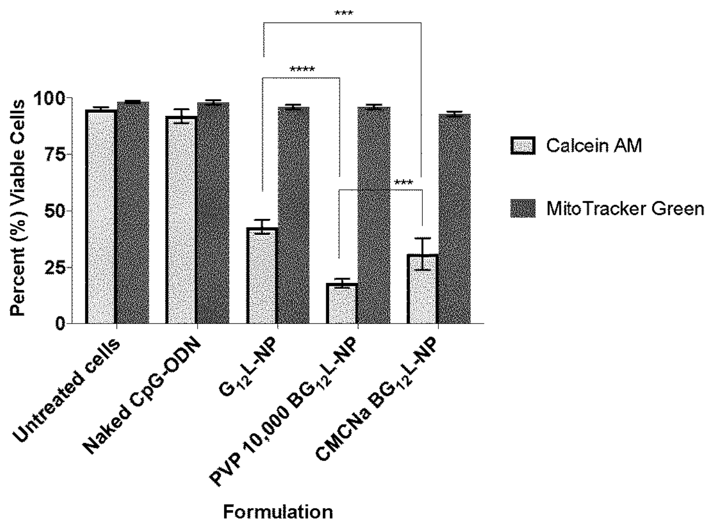
FIG. 13 shows Comparison of cell viability measured by MitoTracker Green FM viability dyes after 4 hours stimulation with $G_{12}$L-NP and $BG_{12}$L-NP formulations.

MitoTracker Green FM viability dye was used to assess viability. After 4 hours of stimulation, all formulations maintained high mitochondrial activity and had near 100% viability similar to untreated cells and cells stimulated with naked CpG-ODN (FIG. 13). Values expressed represent mean±S.D. (n=3). Statistically significant differences between experimental groups were determined by two-way ANOVA with Tukey's multiple comparison test. Statistics were performed between untreated cells and cells dosed with NP formulations, where ** $p<0.0001$, * $p<0.001$.

The viability of HD11 chicken macrophages was also measured 24 hours after initial dosing. Once again $G_{12}L$-NPs and $BG_{12}L$-NPs in both excipients (PEG400 and PG) maintained high mitochondrial activity comparable to cells stimulated with naked CpG-ODN and untreated cells. They all maintained a viability above 95%). The same viability was also maintained when cells were stimulated with blank $G_{12}L$-NPs and $BG_{12}L$-NPs.

HD11 Cell Viability after Transfection with G-NPs

After transfection with G-NPs and gemini micelles (blank NP), cells showed near 100% viability 24 hours after initial cell dosing.

HD11 Cell Viability after Transfection with C-NPs or CG-NPs

After transfection with C-NPs or CG-NPs no difference in viability was observed in comparison to untreated cells and naked CpG-ODN. Neither MW of another biopolymer (C) were harmful to cells.

HD11 Cell Viability after Transfection with CL-NPs

Unlike other formulations, CL-NPs were very toxic to HD11 cells. A low percentage of the cell population had mitochondrial activity at 2 and 24 hours post dosing in comparison to untreated cells and cells transfected with naked CpG-ODN. In fact, the flow cytometry scatter data revealed a high density of cells having lower cell forward and side scatter, as well as a dramatic increase in the number of events indicative of a high presence of cellular debris.

Effect of Nebulization on Particle Characteristics and In Vitro Performance

Figure 14:
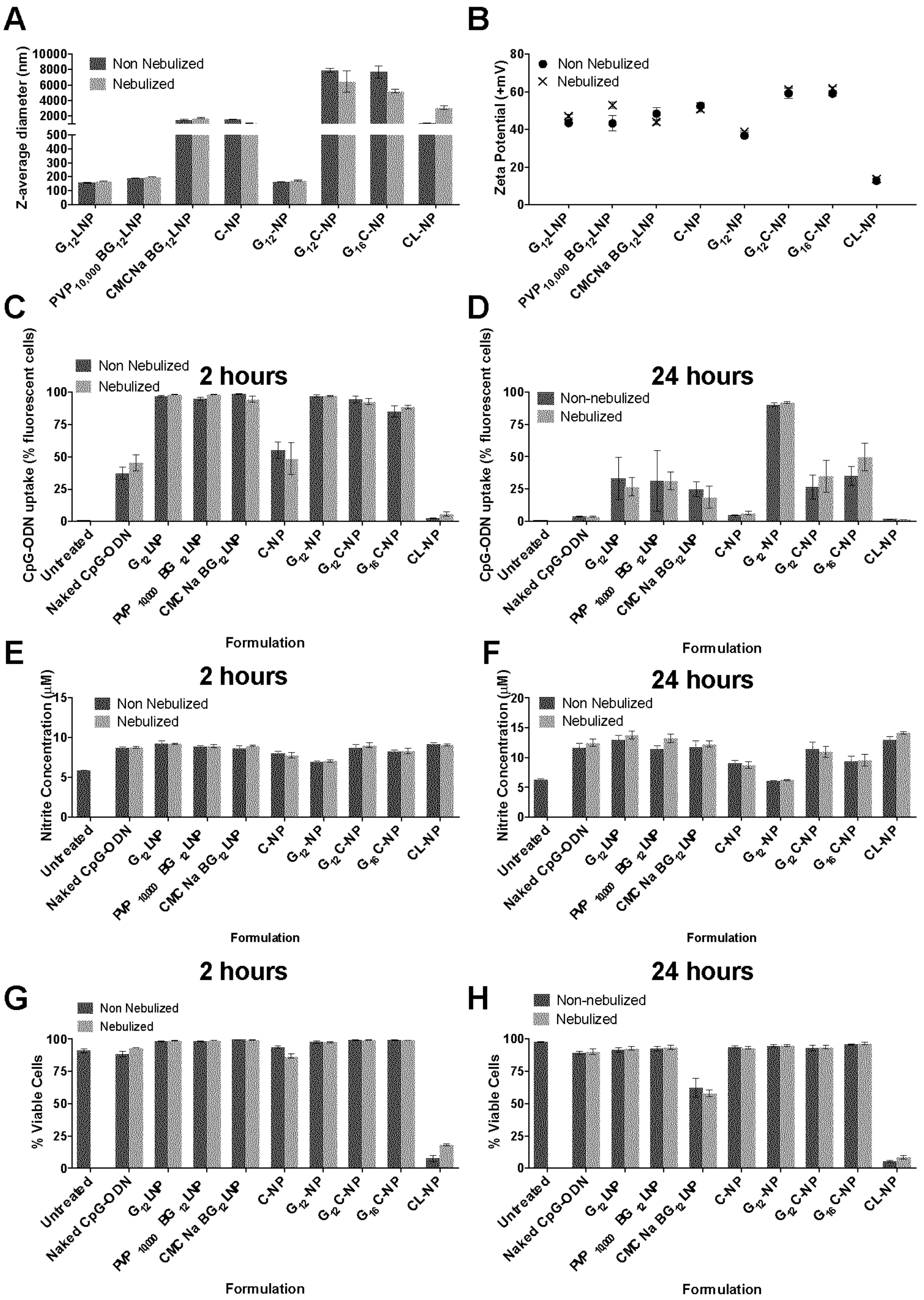
FIG. 14 shows effect of nebulization on physicochemical characteristics and performance of NP formulations.

Selected formulations based on CpG-ODN uptake, ease and reproducibility of formulation, were tested in vitro after nebulization and compared to non-nebulized formulations. Nebulization had no effect on particle characteristics as the average hydrodynamic diameter and zeta potential were very similar before and after nebulization for all formulations (FIG. 14 A, B). The in vitro performance of nebulized formulations was also similar with respect to CpG-ODN uptake, nitrite production, and viability at 2 and 24 hours in comparison to non-nebulized formulations (FIG. 14 C-H).

NP formulations were nebulized with a compressor nebulizer and subsequently collected for characterization and testing in vitro in HD11 cells. Differences in Z-average hydrodynamic diameter size (A), zeta potential (B) and effect on CpG-ODN uptake (C, D), nitrite production (E, F), and viability (G, H) in HD11 cells were compared to non-nebulized formulations. Effects nebulization on CpG-ODN uptake, nitrite production, and viability were measured 2 hours post dosing and 24 hours post dosing. Values expressed represent mean±S.D., n=3.

Cellular CpG-ODN Localization Post Transfection

Figure 15:
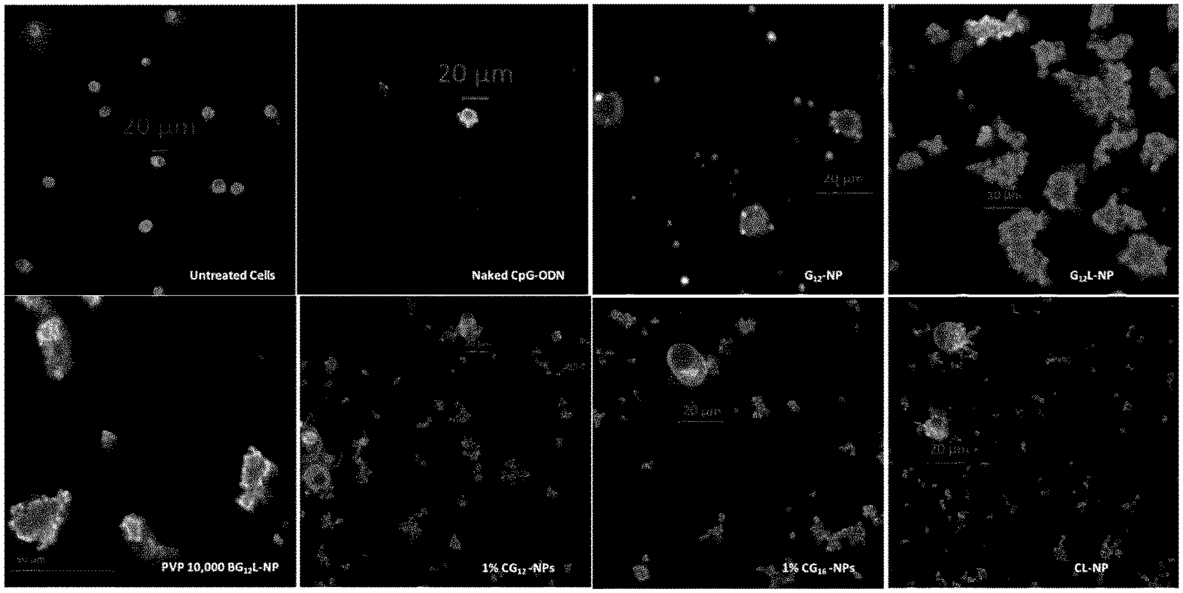
FIG. 15 shows Localization of CpG-ODN uptake in HD11 cells transfected with naked CpG-ODN and NP formulations 2 hours post dosing.
Figure 16:
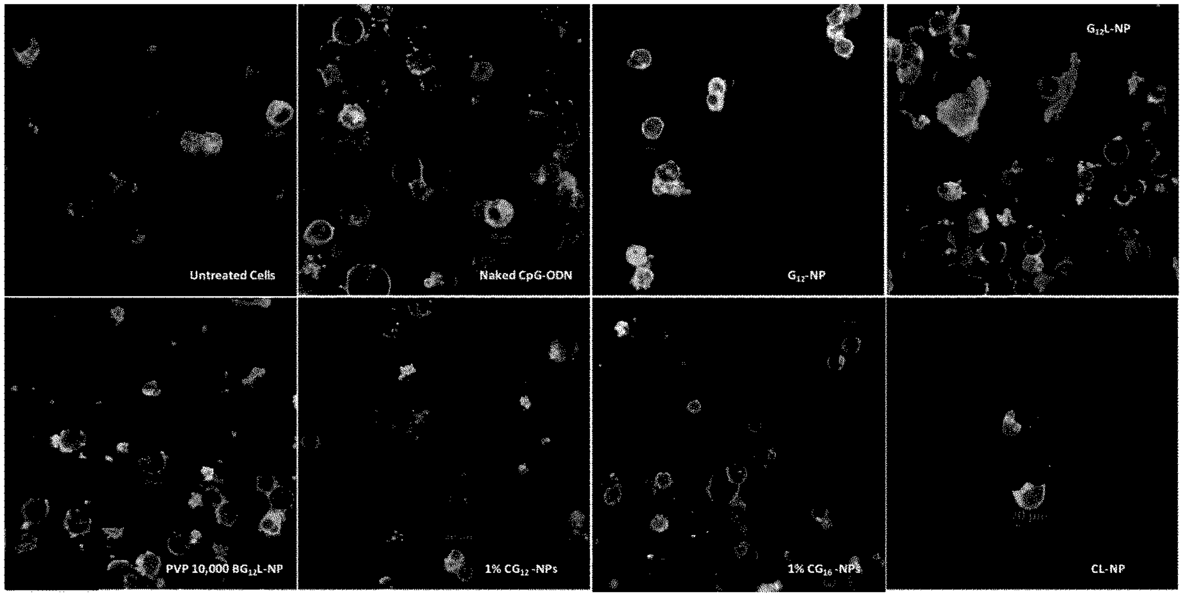
FIG. 16 shows Localization of CpG-ODN uptake in HD11 cells transfected with naked CpG-ODN and NP formulations 24 hours post dosing.

The localization of Alexa Fluor 647 labeled CpG-ODN during transfection of HD11 cells was tracked by confocal microscopy immediately after dosing for 2 hours (FIG. 15), and 24 hours after dosing (FIG. 16). Cells were labeled with Vybrant™ green Dil cell membrane dye (green) in order to determine whether CpG-ODN was membrane bound or intracellular.

Two hours after transfection with naked CpG-ODN it was evident that the CpG-ODN was surrounding the cell membrane. Cells transfected with $G_{12}L$-NPs and $BG_{12}L$-NPs showed CpG-ODN bound to the cell membrane and inside the cells. $G_{12}$-NPs and $CG_{12}$-NPs show CpG-ODN also interacting with the cell membrane, but no CpG-ODN was visible within the cytoplasm of the cells, as opposed to $G_{12}L$-NP and $BG_{12}L$-NP treated cells, which showed intracellular CpG-ODN. After treatment with each of these NPs, cell morphology noticeably changed. Transfection with the CL-NP formulation was the most toxic to cells, as a significant amount of cellular debris was present after 2 hours of dosing. These morphological observations were consistent with the results of flow cytometry which detected an increase in cellular debris and changes in cell size and granularity.

HD11 cells were transfected with NPs containing Alexa Fluor 647 labelled CpG-ODN for 2 hours. Cell membrane was stained with Vybrant™ green Dil for localization (green). Images were taken immediately after 2-hour dosing and evaluated for presence of red fluorescence resulting from CpG-ODN (pink).

Twenty-four hours after initial dosing, CpG-ODN was intracellularly located with all NP formulations (FIG. 16). The confocal microscopic images confirm intracellular CpG-ODN uptake and reveal that the cells recovered from the initial toxic effects at the 2-hour time point (see FIG. 15 versus FIG. 16). Additionally, the $G_{12}$-NP formulation appears to result in the most significant amount of CpG-ODN retention. In $G_{12}$-NP treated cells, CpG-ODN is present throughout the cellular cytoplasm in comparison to other formulations and naked CpG-ODN, which had only concentrated areas of CpG-ODN within the cytoplasm.

HD11 cells were transfected with NPs containing Alexa Fluor 647 labelled CpG-ODN for 2 hours. Cell media was replaced and cell membrane was stained with Vybrant™ green Dil for localization 24 hours later (green). Images were taken 24 hours post dosing and evaluated for presence of red fluorescence resulting from CpG-ODN (pink).

In Vivo Biodistribution of CpG-ODN NP Formulations Versus Naked CpG-ODN Solution NPs were selected for in vivo evaluation based on physicochemical properties and in vitro data. One formulation from each different type of NP was evaluated with the exception of C-NPs, since they were inferior to G-NPs, $G_{12}$L-NPs, $BG_{12}$L-NPs, and CG-NPs based on CpG-ODN uptake and retention in vitro studies. The formulation from each group was chosen based on colloidal stability, ease of formulation, and highest retention, and uptake.

Figure 17:
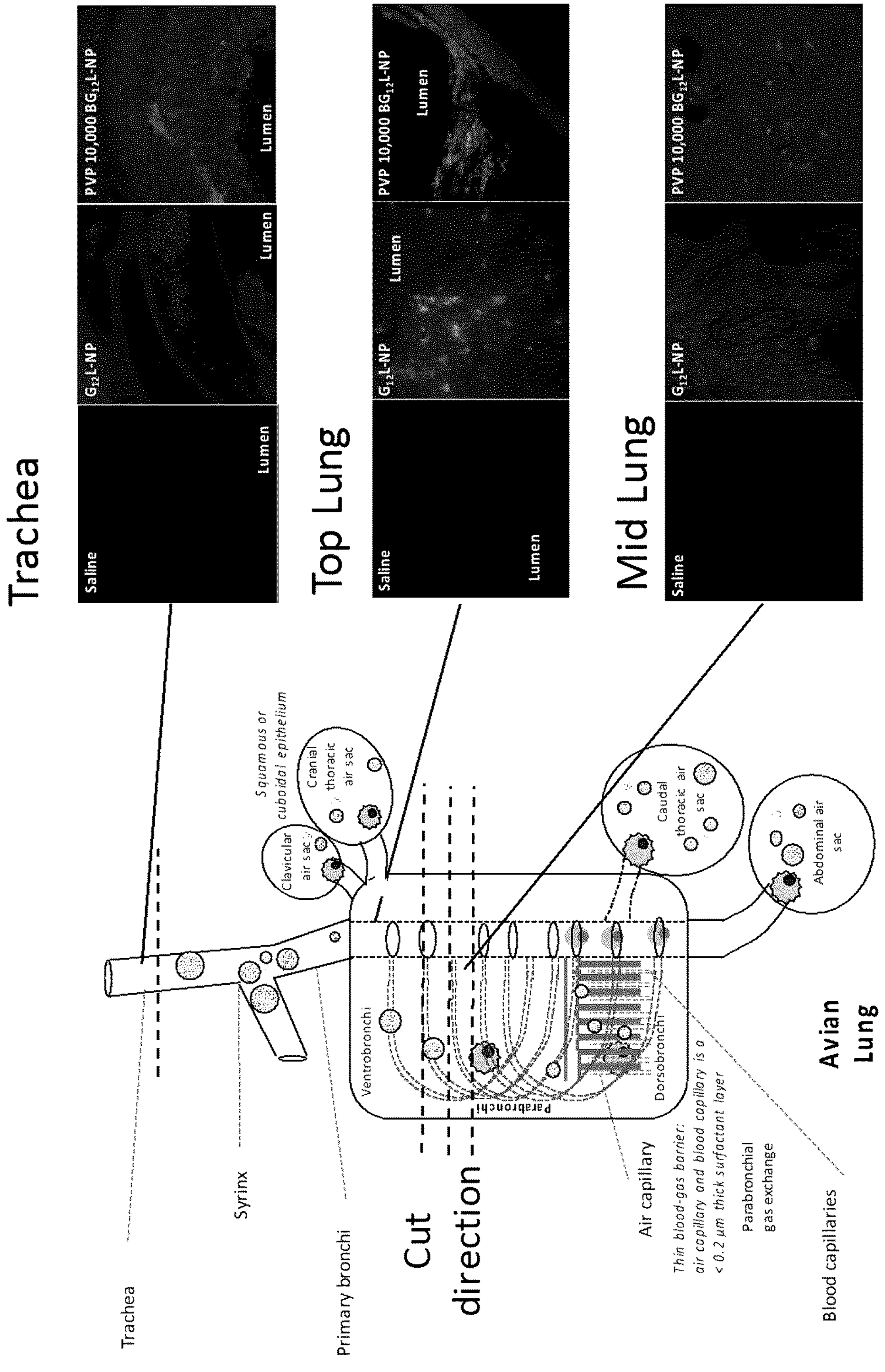
FIG. 17 shows biodistribution of $G_{12}$L-NPs and PVP 10,000 $BG_{12}$L-NPs in the respiratory tract of 1-day old chicks 2 hours post nebulization.

Two separate biodistribution experiments were performed. In the first set of experiments the biodistribution of $G_{12}$L-NP and $BG_{12}$L-NP formulations after 2 hours of NP administration in the chick respiratory tract were compared. Since $G_{12}$L-NPs and PVP 10,000 $BG_{12}$L-NPs in PEG 400 excipient were the most uniform, had >+40 mV zeta potential, were stable over a 20-day period, reproducible, and increased uptake and retention of CpG-ODN, they were chosen for biodistribution in chick lungs. The objective of the first experiment was to determine the extent of short term biodistribution (2 hours post nebulization) in different areas of the chick respiratory tract. Formulations were tagged with NBD-PC lipid for detecting NP distribution. Serial cross sections along the chick respiratory tract were cut and examined for evidence of NP deposition. After two hours of dosing, particles could be identified in the tracheal epithelium near the lumen (FIG. 17). Particles were also present in the top of the lung cranially located near the lumen primary bronchi in the cranial lung (FIG. 17). Here, distinct cluster areas of fluorescence were present. Towards the middle of the lung, distinct areas of fluorescence were seen among the bronchi. Sections caudally located in the lung were also examined for evidence of particle deposition, although minimal particle deposition was observed. A summary of areas of the lung were particles were located is shown in Table 15.

TABLE 15

Summary of evidence of particle distribution in the respiratory tract of day old chicks post nebulization with $G_{12}$L-NPs and PVP 10,000 $BG_{12}$L-NPs

| Section | Nanoparticle Type | Time Point (minutes) | Area of particle deposition | Total Number of Images | # of times present | # of birds it occured in/ total # of birds analyzed |
|---|---|---|---|---|---|---|
| Tracheal bifurcation | Saline Control | 120 | no immediate signs | 10 | 5 | 2/2 |
| | Saline Control | 120 | some signs of autofluorescence, some chondrocyte cell structures /stained | | 2 | 1 (bird control 2) |
| | PVP 10,000 $BG_{12}$L-NP | 15 | chondrocytes within trachea near lumen | 20 | 16 | 5/5 |
| | PVP 10,000 $BG_{12}$L-NP | 15 | mucosal lining of trachea near lumen | | 1 | 2/5 |
| | PVP 10,000 $BG_{12}$L-NP | 120 | chondrocytes within trachea | 27 | 15 | 4/5 |
| | PVP 10,000 $BG_{12}$L-NP | 120 | mucosal lining of trachea near lumen | | 6 | 2/5 |
| | $G_{12}$L-NP | 15 | chondrocytes within trachea | 18 | 13 | 4/5 |
| | $G_{12}$L-NP | 15 | mucosal lining of trachea near lumen | | 2 | 3/5 |
| | $G_{12}$L-NP | 120 | chondrocytes within trachea | 16 | 8 | 4/5 |
| | $G_{12}$L-np | 120 | mucosal lining of rachea near lumen | | 3 | 3/5 |
| Top Lung | Saline Control | 120 | no immediate signs | 17 | 12 | 2/2 |
| | Saline Control | 120 | some signs of autofluorescence (diffuse) | | 5 | 2/2 (only in bird control 2 top lung section 1) |
| | PVP 10,000 $BG_{12}$L-NP | 15 | within primary bronchus mucosal tissue | 17 | 12 | 3/5 |
| | PVP 10,000 $BG_{12}$L-NP | 15 | within lung tissue | | 3 | |
| | PVP 10,000 $BG_{12}$L-NP | 120 | within primary bronchus mucosal tissue | 24 | 22 | 3/5 |
| | $G_{12}$L-NP | 15 | Primary bronchus (diffuse fluorescence) | 11 | 9 | 3/5 |
| | $G_{12}$L-NP | 120 | | 13 | 12 | 1/4 |

TABLE 15-continued

Summary of evidence of particle distribution in the respiratory tract of day old chicks post nebulization with $G_{12}$L-NPs and PVP 10,000 $BG_{12}$L-NPs

| Section | Nanoparticle Type | Time Point (minutes) | Area of particle deposition | Total Number of Images | # of times present | # of birds it occured in/ total # of birds analyzed |
|---|---|---|---|---|---|---|
| Mid Lung | Saline Control | 120 | no immediate sign, faint autofluorescence | 7 | 7 | 2/2 |
| | PVP 10,000 $BG_{12}$L-NP | 15 | tissue between bronchi (scattered) | 7 | 5 | 4/5 |
| | PVP 10,000 $BG_{12}$L-NP | 120 | fluorescent areas near bronchi lumen | 21 | 20 | 3/5 |
| | $G_{12}$L-NP | 15 | lung tissue near bronchi/parabronchi? (scattered/diffuse) | 23 | 12 | 2/5 |
| | $G_{12}$L-NP | 15 | lung tissue near bronchi/parabronchi? (localized) | | 10 | 3/5 |
| | $G_{12}$L-NP | 120 | lung tissue near bronchi/parabronchi? (scattered/diffuse) | 14 | 9 | 2/5 |
| | $G_{12}$L-NP | 120 | lung tissue near bronchi/parabronchi? (localized) | | 7 | 3/5 |
| Lower Lung | Saline Control | 120 | no immediate signs | 22 | 18 | 1/1 |
| | PVP 10,000 $BG_{12}$L-NP | 15 | fluorescent areas near bronchi lumen (very faint, rare) | 13 | 4 | 1/2 |
| | $G_{12}$L-NP | 15 | autofluorescence? | 1 | 1 | 1/1 |
| | $G_{12}$L-NP | 120 | lung tissue near bronchi/parabronchi? (scattered/diffuse) | 1 | 1 | 1/1 |

Lung sections of birds were imaged using CLSM. Particles were labelled with fluorescent NBD-PC lipid tag for detection in the respiratory tract. Description of observations are outlined.

1-day old chicks were nebulized in a chamber for 15 minutes with selected NP formulation. Respiratory tract tissues including the trachea and lung were isolated 2 hours post nebulization. NP formulations were labeled with NBD-PC lipid.

1-day old chicks were nebulized in a chamber for 15 minutes with corresponding NP formulation. The chick lung was isolated 2 hours post nebulization. NP formulations were labeled with FITC-another biopolymer (C) and Alexa Fluor 647 CpG-ODN.

Evaluation of Protection Against *E. coli* Challenge

Figure 18:
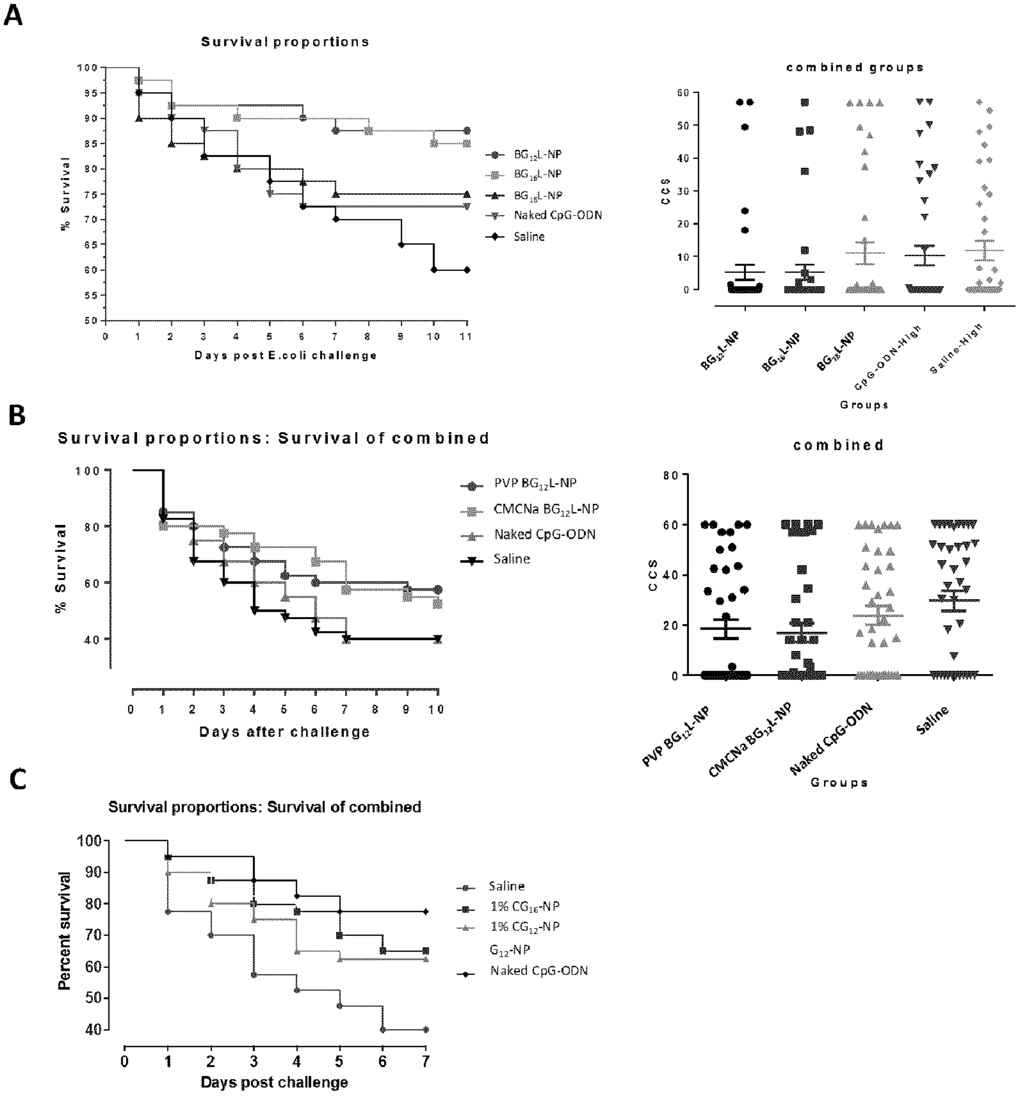
FIG. 18 shows In vivo protection of neonatal chicks from *E. coli* challenge after intrapulmonary treatment with CpG-ODN in various NP delivery systems.

NP formulations that were able to elicit innate immune activation, i.e. retain the highest in vitro uptake after 24 hours of dosing, and maintain reproducible formulation characteristics were chosen to evaluate the extent of protection in 1-day old chicks. Several in vivo experiments were conducted to evaluate formulations in a step by step manner (FIG. 18). Data shown is the result of combined challenge with high and low *E. coli* dose for clarity.

In the first experiment, the effect of gemini-tail length on BGL-NPs efficacy was evaluated. BGL-NPs constructed with gemini 12-3-12 and 16-3-16 resulted in 90% survival and reduced combined clinical score, whereas naked CpG-ODN and gemini 18-3-18 BGL-NPs produced about 75% survival rate. The saline control was at a 40% survival rate using a 2-day post-treatment challenge protocol (FIG. 18 A).

In the next experiment, the biopolymer of BGL-NPs was evaluated. Both PVP and CMCNa polymers had similar effects in improving survival and clinical score compared to naked CpG-ODN and saline control (60% survival for each polymer group vs. 40% for naked CpG-ODN and saline, respectively) (FIG. 18 B). These survival scores are lower compared to the first experiment, which is attributed to the timing of the challenge (3 days vs 2 days post-treatment in the previous experiment).

Given enhanced retention, $G_{12}$-NPs, 1% $CG_{12}$-NPs, and 1% $CG_{16}$-NPs were also tested for their ability to improve bird survival after infection. All three NP formulations were able to enhance bird survival in comparison to the saline control (FIG. 18 C). The effect of gemini tail length of 1% CG-NPs on percent survival was not significant (both about 65% survival rate). In comparison, $G_{12}$-NPs provided about 80% survival rate. This was similar to naked CpG-ODN using a 2-day post-treatment challenge protocol. The saline control was at a 40% survival rate.

FIG. 18 shows in vivo protection of neonatal chicks from *E. coli* challenge after intrapulmonary treatment with CpG-ODN in various NP delivery systems. Protection was evaluated by measuring chick survival and monitoring clinical signs (combined clinical score, CCS). The in vivo screening selected delivery systems are shown. NP formulations were nebulized with Medpro compressor nebulizer to groups of 1-day old chicks followed by challenge with *E. coli.*

FIG. 18 A shows screening of BGL-NPs to compare the effect of gemini structure on efficacy. Gemini surfactants 12-3-12, 16-3-16 and 18-3-18 were evaluated with PVP Kollidon 25 as the biopolymer. Neonatal broiler chicks were given CpG-ODN solution or NP formulations by nebulization at the age of day 1. Chicks were challenged with two lethal doses of *E. coli* 2 days post CpG-ODN administration. Data were collected on daily mortality, bacteriological scoring and daily clinical scoring. CpG-ODN dose was 100 µg/100 µL/bird; n=40; challenge was performed with *E. coli* $1\times10^5$ CFU/bird on Day 2 after treatment.

FIG. 18 B shows screening of BGL-NPs to compare the effect of two different biopolymers on efficacy. Gemini surfactants 12-3-12 with two different biopolymers (PVP and CMCNa) were evaluated. Neonatal broiler chicks were given CpG-ODN solution or NP formulations by nebulization at the age of day 1. Data were collected on daily mortality, bacteriological scoring and daily clinical scoring. CpG-ODN dose was 100 µg/100 µL/bird; n=40; challenge was performed with *E. coli* $1\times10^5$ CFU/bird on Day 3 after treatment. FIG. 18 C shows evaluation of G-NPs (12-3-12) and 1% CG NPs prepared with gemini surfactant 12-3-12 or 16-3-16. Neonatal broiler chicks were given CpG-ODN solution or NP formulations by nebulization at the age of day 1. Data were collected on daily mortality, bacteriological scoring and daily clinical scoring. CpG-ODN dose was 100 μg/100 μL/bird; n=40; challenge was performed with *E. coli* $1\times10^5$ CFU/bird on Day 2 after treatment.

A gemini NP delivery system was employed for a CpG-ODN vaccine in attempt to improve the stimulation of innate immunity and protective properties of CpG-ODN in broiler chicks against bacterial infection such as *E. coli*. Previous studies have proven that CpG-ODN is a protective vaccine against *E. coli* infection and other bacterial infections common in broilers [25, 27, 26, 61]. Moreover, the incorporation of CpG-ODN in NPs has improved the protective effects of CpG-ODN in broiler chicks in vivo through subcutaneous and in ovo routes of vaccination [46, 27]. By developing a novel gemini-biopolymer NP delivery system, it was expected that improved delivery and immune stimulation will occur in broiler chicks via the pulmonary route, a cost-effective immunization method in poultry. Since macrophages migrate into the chicken respiratory system upon recognition of foreign pathogens and act as antigen presenting cells to induce an innate immune response, the chicken macrophage cell line HD11 was chosen to investigate immune-stimulatory properties of the CpG-ODN NP vaccines formulated.

NP modification is a popular method to improve gene delivery by lipid and polymer based NPs that have shown limited gene transfection in vivo. Techniques to achieve superior multifunctional NPs include chemical modification of materials, antibody/aptamer conjugation, peptide functionalization, and multi-material incorporation. This results presented here are directed to several hybrid NP formulations made up of different classes of biocompatible materials, a much simpler method than chemical modification. For each of the 6 types of NP groups investigated ($G_{12}$L-NPs, $BG_{12}$L-NPs, G-NPs, C-NPs, CG-NPs, CL-NPs), characterization was undertaken based on reproducibility, colloidal stability, and manufacturing capacity. Moreover, the different NP groups were characterized and compared in their ability to improve transfection in vivo.

Characterization of Nanoparticle Formulations

The effect of PVP biopolymer MW on the size and zeta potential of the $BG_{12}$L-NPs formulated in PEG400, was monitored. The MW of the polymer did not affect the size of the particles, and gave a relatively uniform size distribution around 200 nm. The formulation preparation for the $G_{12}$L-NPs/$BG_{12}$L-NPs particles involved formation of blank NP vesicles prior to CpG-ODN addition. The polymer did not influence particle size with any of the blank NPs, all were about 15-20 nm.

the $G_{12}$L-NP and PVP 10,000 $BG_{12}$L-NP formulations in PEG 400 excipient were selected for further testing owing to reproducibility of particle size from batch to batch. They also had a positive zeta potential (+53.2 and +42.8 mV, respectively), well above the +30 mV threshold for colloidal stability.

G-NPs were also tested to compare the basic micellar NP with the lipid and polymeric hybrid components ($G_{12}$L-NPs/$BG_{12}$L-NPs and CG-NPs, respectively). G Increasing tail length of the gemini surfactant affected the size and zeta potential of G-NPs which has also been previously observed in plasmid-gemini complexation with a charge ratio (+/−) 10:1 [68]. Similar to plasmid-gemini complexes, an increase in zeta potential with increasing tail length of G-NPs was observed. Unlike the plasmid-gemini complexation, an increase in size with increasing gemini tail length was observed with CpG-ODN oligonucleotides.

Of the C-NPs tested, two types of low molecular weight another biopolymer (C) were used with a relatively high DD since these characteristics have been reported as factors that improve gene transfection [69, 70, 71, 72]. The ultra-low molecular weight another biopolymer (C) produced smaller NPs in comparison to the low molecular weight another biopolymer (C), similar to previous observations in [73, 72]. However, unlike other investigations, the size of C-NPs were in the micron size range, not in the NP size range of <1000 nm. This is not likely due to incomplete formation of complexes and low stability, as has been previously reported when a low charge ratio is used for complexation of DNA-another biopolymer (C) particles [75, 76], as the high zeta potential of C-NPs in this project indicated colloidal stability. Instead, perhaps particle aggregation occurred which resulted in the sedimentation of the formulation over time.

The incorporation of another biopolymer (C) into gemini delivery systems was tested as a means to improve stability in biological media and improve transfection. Increasing another biopolymer (C) concentration was the main factor influencing the final size and zeta potential of the CG-NPs to increase, but gave very polydisperse populations and micron sized particles. All CG-NPs were stable colloids in acidic conditions (pH 3.3-4.8). However, 1% $CG_{12}$-NP and 1% $CG_{16}$-NP were chosen for further characterization due to lower PDI indexes (<0.3) indicating more uniform formulations.

Similar to C-NPs and CG-NPs, CG-NPs had a size of −1 μm. However, in contrast to C-NPs and CG-NPs, it had a low zeta potential (+12.7 mV) which indicated a formulation with low stability.

NP Characterization in Biological Buffers

An important aspect of NP delivery systems is the ability to maintain stability within the biological environment in order to provide protection against enzymatic degradation prior to reaching the target site. In terms of vaccine development, the protein-NP interactions could also affect antigen presentation. Yet, most analyses characterize size and zeta potential of NP formulations in its prepared state. The zeta potential for all groups of formulations (G-NPs, $G_{12}$L-NPs/$BG_{12}$L-NPs, C-NPs, CG-NPs, CL-NPs) in all biological media decreased below +20 mV. This indicated a decrease in stability of formulations upon entering the biological environment. Unlike the another biopolymer (C) formulations, the $G_{12}$L-NPs and PVP 10,000 $BG_{12}$L-NPs maintained a positive charge around +10 mV which could help improve transfection and retention.

Correlation of Particle Characteristics with Cellular Uptake

The transfection ability of naked CpG-ODN in HD11 cells prior to testing NP formulations was monitored to establish proper transfection parameters.

CpG-ODN uptake over 4 hours was monitored in HD11 cells at different quantities of naked CpG-ODN. $G_{12}$L-NPs and $BG_{12}$L-NPs consistently and significantly improved the percentage of cells transfected with CpG-ODN in comparison to naked CpG-ODN over the 4 hours. Moreover, $G_{12}$L-NPs and $BG_{12}$L-NPs were able to increase the percentage of cells with CpG-ODN uptake within the same time period despite incubation with a lower amount of CpG-ODN. Additionally, uptake was observed only 1 hour after incubation. Because of this, subsequent experiments were executed with a dosing/incubation time of 2 hours with naked CpG-ODN and formulations.

Of the six groups of formulations ($G_{12}$-L-NPs, $BG_{12}$-L-NPs, G-NPs, C-NPs, CG-NPs, CL-NPs), all were able to improve transfection efficiency with CpG-ODN uptake after 2 hours when compared to naked CpG-ODN with the exception of CL-NPs (see FIG. 19A). Comparatively, all formulations that contained gemini surfactant performed better than C-NP and CL-NP formulations without gemini. C-NP was only able to transfect half the cell population in comparison to gemini containing formulations.

Figure 19:
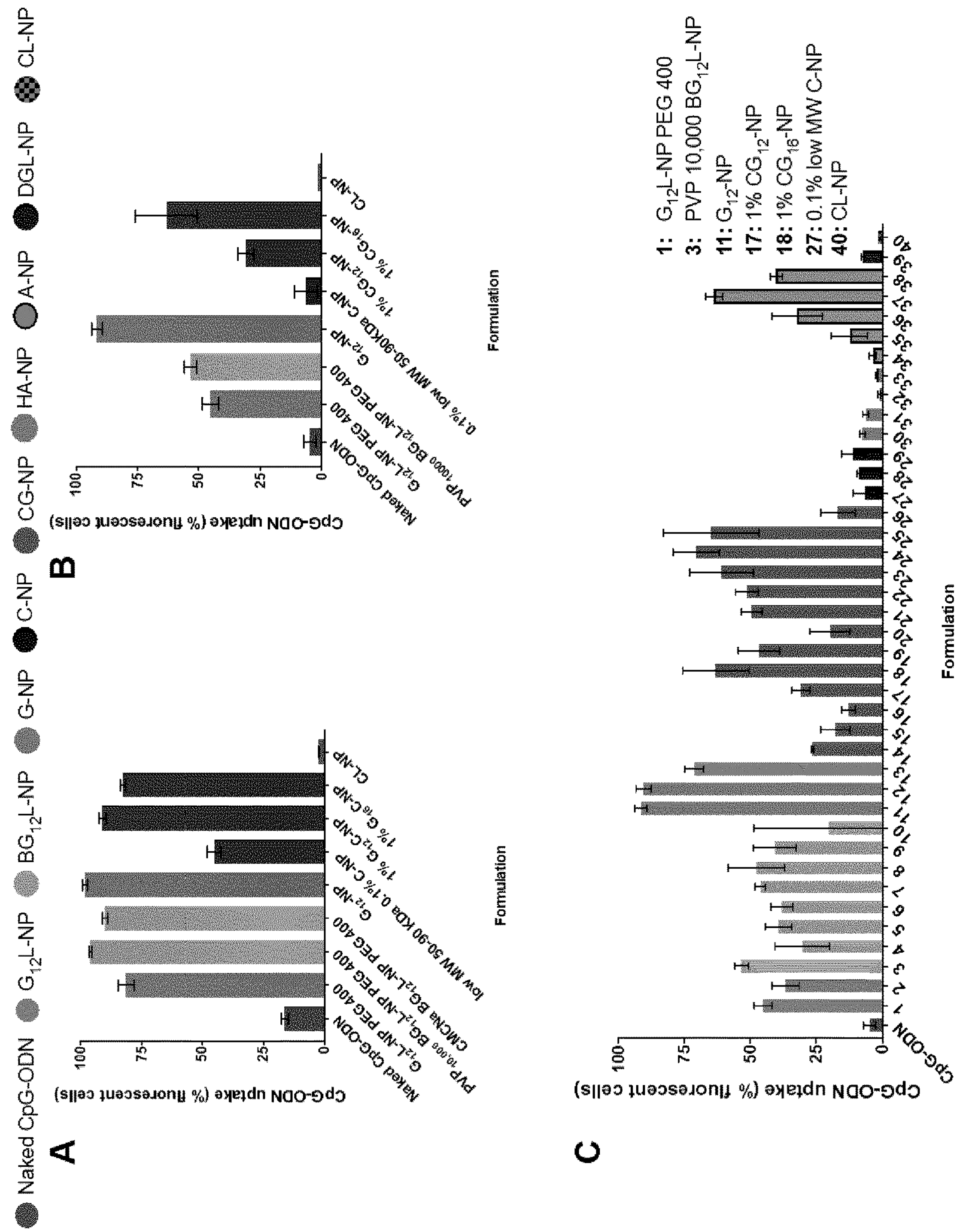
FIG. 19 shows overall comparison of CpG-ODN uptake and retention in HD11 cells resulting from transfection with different types of NPs.

Another aspect explored was slow or sustained release of CpG-ODN for lasting immune activation. The retention of CpG-ODN was also observed 24 hours after the removal of transfection media following the initial uptake after 2 hours of treatment (FIG. 19 B, C). Distinctions between formulations were more easily obtainable when analyzing retention of CpG-ODN following transfection. In fact, several formulation groups (HA-NP, A-NP, DGL-NP) not discussed here were not further investigated since they performed inferior to the formulations highlighted in FIG. 19 A, B.

The formulation groups: $G_{12}$-L-NPs, $BG_{12}$-L-NPs, G-NPs, and CG-NPs were all able to sustain CpG-ODN within the cellular environment up to 24 hours post dosing. G-NPs were best at retaining CpG-ODN within HD11 macrophages and had similar percentage of cells with CpG-ODN at 2 hours and 24 hours. This indicated a high stability of G-NP formulations. Hybrid NP groups $G_{12}$L-NPs, $BG_{12}$L-NPs, and CG-NPs performed similarly. Given the greater detection of CpG-ODN in cells treated with NP formulations, this could indicate a sustained release property from the NPs. This sustained release effect could prolong an active innate immune response in vivo. C-NPs and CL-NPs were not able to retain a significant amount of CpG-ODN in comparison to naked CpG-ODN.

All formulations were compared in their ability to enhance CpG-ODN uptake in comparison to naked CpG-ODN. Best formulations based on method preparation and CpG-ODN uptake were compared at 2 hours post dosing (A) and 24 hours post dosing (B). Retained level of CpG-ODN uptake 24 hours post dosing of all formulations generated in this project categorized by group are also compared (C). Values expressed represent mean±S.D., n=3.

Whether or not gene transfection by NPs is successful at the cellular level, has been attributed to size and zeta potential. Effects of zeta potential on HD11 macrophage uptake was also explored using NP characterization data in its prepared state and in RPMI 1640 basic transfection media. Generally, preparation of formulations with ζ potential above +40 mV resulted in higher CpG-ODN uptake. Characterization of ζ potential in biological buffers may mimic the environment of the lung more closely. From the data collected both negative and positively charged NPs resulted in high NP uptake corresponding to the $G_{12}$-NP, $G_{12}$L-NP, and $BG_{12}$L-NPs. NPs with greater negative charge (1% $CG_{16}$-NP) in basic media also achieved relatively high uptake while near neutral formulations (C-NPs) did not.

It is demonstrated herein that G-NPs, C-NPs, $G_{12}$L-NPs, $BG_{12}$L-NPs, and CG-NPs are able to overcome barriers to cellular internalization and improve CpG-ODN uptake. Furthermore, with the exception of C-NPs, these formulations are able to retain more CpG-ODN intracellularly 24 hours post dosing. A high uptake in HD11 cells could translate into an improvement in antigen presentation and increased phagocytic activity in antigen presenting cells in the chicken immune system. The capacity to retain CpG-ODN could translate into extended release vaccine formulations that could promote formation of long-term immunity in chickens. From an economic standpoint, increased uptake and retention of CpG-ODN by NPs could reduce the amount of CpG-ODN needed in a single vaccine dose and reduce costs.

Comparing Immune Stimulation Effects from Different Nanoparticle Formulations

Unlike other applications of gene delivery systems that require gene translation in the cytoplasm, in chickens a CpG-ODN molecule interacts intracellularly with its receptor TLR 21 within the endo-lysosome. CpG-ODN NP delivery could change intracellular trafficking of CpG-ODN within the cell and possibly mask innate immune activation or BGL-NPs, G-NPs, and CG-NPs could result in extended release of the CpG-ODN antigen and prolong effects of immunity against infection given their high retention capacity. Activation of HD11 macrophages was also investigated post dosing.

Of the formulations tested in this project, a significant amount of nitrite production in vitro was observed 12 and 24 hours post dosing in relation to untreated cells. In general, nitrite concentration doubled from 12 to 24 hours post dosing. Of the 6 formulation groups, PVP 10,000 $BG_{12}$L-NPs, C-NPs, and CG-NPs resulted in cells producing the greatest amount of nitrite in comparison to untreated cells.

$G_{12}$L-NPs, $BG_{12}$L-NPs, C-NPs, and CG-NP formulations developed herein were well tolerated.

The dramatic increase in SSC, indicative of high cell granularity resulting from uptake of CpG-ODN $G_{12}$L-NPs, $BG_{12}$L-NPs, G-NPs, CG-NPs may be the consequence of a high number of endosomes within cells containing NPs. In contrast, naked CpG-ODN and C-NP transfected cells did not have as dramatic a shift due to lower levels of CpG-ODN uptake.

Local Lung Biodistribution of NPs

Few investigators have studied the biodistribution of particles within the avian respiratory tract after spray vaccination. Of the few studies that exist, spray vaccine particles can provide local and topical treatment in air sacs. The nebulizer used in this study theoretically generates 1-5 μM sized aerosol droplets as per the manufacturer and therefore should bypass mucociliary transport to a certain extent. Evidence of $G_{12}$L-NP and $BG_{12}$L-NP deposition was observed in the chick respiratory tract 2 hours after nebulization and can confirm that the delivery method effectively administers the vaccine to the lung. $G_{12}$L-NPs and $BG_{12}$L-NPs deposited in the trachea, the tracheal bifurcation, and appeared to diffuse through the connective lung tissue.

In general, extensive in vivo mammalian studies of NP distribution in the lung environment are performed with more controlled dose administration by intra-tracheal instillation or inhaler administration to individual animals. However, not many groups have attempted to investigate whether NPs and DNA dissociate within the lung environment. Evidence of intact CpG-ODN NPs within the lung environment were found using 1% $CG_{12}$-NPs along the mid lung region. However, 1% $CG_{12}$-NPs and 1% $CG_{16}$-NPs mainly appeared to dissociate from CpG-ODN within the first 2 hours of being in the lung environment.

Confirmation of the presence of $G_{12}$L-NP, $BG_{12}$L-NP, $G_{12}$-NP, and 1% CG-NP biodistribution in the chick lung confirms delivery of the vaccine to the chick respiratory system, and initiation of an immune response at the site of infection.

Evaluation of Protection in 1-Day Old Chicks Against *E. coli* Challenge

Applications of NP drugs/vaccines could theoretically reduce dosing frequency due to the increased accumulation of drug per particle at specific sites. Evidence of this phenomenon was seen in HD11 cellular CpG-ODN uptake studies. Based on CpG-ODN uptake and retention data, viability, nebulization compatibility, and cellular toxicity, $G_{12}$-NPs and $BG_{12}L$-NPs appear the most compatible and effective for the intrapulmonary delivery of CpG-ODN.

Using intrapulmonary administration, PVP BGL-NPs were also able to enhance protection in chicks against *E. coli* challenge in comparison to naked CpG-ODN. This is advantageous as spray vaccination does not require needle administration and targets mucosal immunity which can produce local and systemic effects. In the first NP group tested, gemini tail length affected vaccine effectiveness in the following order of effectiveness in protecting chicks: 12-3-12≥16-3-16>18-3-18. Subsequently, $BG_{12}L$-NPs with either PVP or CMCNa showed that both biopolymers were equally effective in enhancing survival rates. This may be explained by similarities in NP uptake, NO production and particle characteristics. For example, the number of CpG-ODN molecules per NP was similar in both types of NP formulations.

As an overall assessment, the survival experimental settings were designed to gain some information about the optimum timing of the challenge and duration of protective effect of the naked CpG-ODN and NP formulations in order to help rank formulations and develop an understanding of the effect of NP composition on protection. It was previously found that naked CpG-ODN solution can protect chicks up to 5 days. However the extent of protection decreased significantly by Day 4-5 [67], indicating that the later the chicks are challenged with *E. coli* after the vaccination, the lower the rate of survival.

In the NP screening experiments, we have used Day 2, 3, or 4 post vaccination for administering the *E. coli* challenge. This experimental variable indicated that PVP BGL-NPs improved protection of chicks compared to naked CpG-ODN when challenged on Day 2 or 3, (FIG. 18 A, B).

Example 11

Temperature and Humidity During Administration

Broiler chicks were placed in a chamber for 30 minutes and received water or CpG-ODN by the intrapulmonary route. The temperature was adjusted to between 22° C. to 24° C. to achieve humidity of 50% to 60% and humidex of 28. To ensure chicks receive an adequate amount of CpG-ODN by the IPL route, it was determined that inside the chamber, humidex must be at 28 or thereabouts and relative humidity between 40-60%. To test the efficacy of the chamber, chicks were collected from the chamber and given a lethal dose of *E. coli* to determine survivability. Survivability of the chicks following a lethal *E. coli* challenge showed significant protection between the negative control (distilled water) and CpG-ODN treated birds collected from all locations in the chamber.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

LIST OF REFERENCES

1. Wierup, M. The control of microbial diseases in animals: alternatives to the use of antibiotics. Int J Antimicrob Ag 14:315-319. 2000.
2. Yassin, H., A. G. J. Velthuis, M. Boerjan, and J. van Riel. Field study on broilers' first-week mortality. Poultry Sci 88:798-804. 2009.
3. H. John Barnes, L. K. N., Jean-Pierre Vaillancourt. Colibacillosis. In: Diseases of Poultry, 12th edition ed. A. M. F. Y. M. Saif, J. R. Glisson, L. R. McDougald, L. K. Nolan, D. E. Swayne, ed. Blacwell Publishing Professional, Iowa. p 691. 2008.
4. Brigden, J. L., and C. Riddell. A survey of mortality in four broiler flocks in western Canada. The Canadian veterinary journal. La revue veterinaire canadienne 16:194-200. 1975.
5. Casewell, M., C. Friis, E. Marco, P. McMullin, and I. Phillips. The European ban on growth-promoting antibiotics and emerging consequences for human and animal health. J Antimicrob Chemoth 52:159-161. 2003.
6. Gyles, C. L. Antimicrobial resistance in selected bacteria from poultry. Animal Health Research Reviews 9:149-158. 2008.
7. Allen, H. K., U. Y. Levine, T. Looft, M. Bandrick, and T. A. Casey. Treatment, promotion, commotion: antibiotic alternatives in food-producing animals. Trends Microbiol 21:114-119. 2013.
8. Millet, S., and L. Maertens. The European ban on antibiotic growth promoters in animal feed: From challenges to opportunities. The Veterinary Journal 187:143-144. 2011.
9. Krieg, A. M., A. K. Yi, S. Matson, T. J. Waldschmidt, G. A. Bishop, R. Teasdale, G. A. Koretzky, and D. M. Klinman. CpG motifs in bacterial DNA trigger direct B-cell activation. Nature 374:546-549. 1995.
10. Neujahr, D. C., C. F. Reich, and D. S. Pisetsky. Immunostimulatory properties of genomic DNA from different bacterial species. Immunobiology 200:106-119. 1999.
11. Yamamoto, S., T. Yamamoto, T. Kataoka, E. Kuramoto, O. Yano, and T. Tokunaga. Unique Palindromic Sequences in Synthetic Oligonucleotides Are Required to Induce Inf and Augment Inf-Mediated Natural-Killer Activity. J Immunol 148:4072-4076. 1992.
12. Yamamoto, S., T. Yamamoto, S. Shimada, E. Kuramoto, O. Yano, T. Kataoka, and T. Tokunaga. DNA from Bacteria, but Not from Vertebrates, Induces Interferons, Activates Natural-Killer-Cells and Inhibits Tumor-Growth. Microbiol Immunol 36:983-997. 1992.
13. Ahmad-Nejad, P., H. Hacker, M. Rutz, S. Bauer, R. M. Vabulas, and H. Wagner. Bacterial CpG-DNA and lipopolysaccharides activate Toll-like receptors at distinct cellular compartments. European journal of immunology 32:1958-1968. 2002.
14. Hemmi, H., O. Takeuchi, T. Kawai, T. Kaisho, S. Sato, H. Sanjo, M. Matsumoto, K. Hoshino, H. Wagner, K. Takeda, and S. Akira. A Toll-like receptor recognizes bacterial DNA. Nature 408:740-745. 2000.

15. Jakob, T., P. S. Walker, A. M. Krieg, M. C. Udey, and J. Vogel. Activation of cutaneous dendritic cells by bacterial DNA and CpG-oligodeoxynucleotides: Implications for the induction of Th1 responses by immunostimulatory DNA. J Leukocyte Biol: 36-36. 1998.
16. Sparwasser, T., E. S. Koch, R. M. Vabulas, K. Heeg, G. B. Lipford, J. W. Ellwart, and H. Wagner. Bacterial DNA and immunostimulatory CpG oligonucleotides trigger maturation and activation of murine dendritic cells. European journal of immunology 28:2045-2054. 1998.
17. Klinman, D. M., A. K. Yi, S. L. Beaucage, J. Conover, and A. M. Krieg. CpG motifs present in bacterial DNA rapidly induce lymphocytes to secrete interleukin 6, interleukin 12, and interferon gamma. P Natl Acad Sci USA 93:2879-2883. 1996.
18. Krieg, A. M., L. Love-Homan, A. K. Yi, and J. T. Harty. CpG DNA induces sustained IL-12 expression in vivo and resistance to *Listeria monocytogenes* challenge. J Immunol 161:2428-2434. 1998.
19. Ray, N. B., and A. M. Krieg. Oral pretreatment of mice with CpG DNA reduces susceptibility to oral or intraperitoneal challenge with virulent *Listeria monocytogenes*. Infection and immunity 71:4398-4404. 2003.
20. Lewis, E. J., S. Agrawal, J. Bishop, J. Chadwick, N. D. Cristensen, S. Cuthill, P. Dunford, A. K. Field, J. Francis, V. Gibson, A. K. Greenham, F. Kelly, R. Kilkushie, J. W. Kreider, J. S. Mills, M. Mulqueen, N. A. Roberts, P. Roberts, and D. E. Szymkowski. Non-specific antiviral activity of antisense molecules targeted to the E1 region of human papillomavirus. Antivir Res 48:187-196. 2000.
21. Zimmermann, S., O. Egeter, S. Hausmann, G. B. Lipford, M. Rocken, H. Wagner, and K. Heeg. Cutting edge: CpG oligodeoxynucleotides trigger protective and curative Th1 responses in lethal murine leishmaniasis. J Immunol 160:3627-3630. 1998.
22. Brownlie, R., J. Z. Zhu, B. Allan, G. K. Mutwiri, L. A. Babiuk, A. Potter, and P. Griebel. Chicken TLR21 acts as a functional homologue to mammalian TLR9 in the recognition of CpG oligodeoxynucleotides. Molecular immunology 46:3163-3170. 2009.
23. Keestra, A. M., M. R. de Zoete, L. I. Bouwman, and J. P. M. van Putten. Chicken TLR21 Is an Innate CpG DNA Receptor Distinct from Mammalian TLR9. J Immunol 185:460-467. 2010.
24. Patel, B. A., S. Gomis, A. Dar, P. J. Willson, L. A. Babiuk, A. Potter, G. Mutwiri, and S. K. Tikoo. Oligodeoxynucleotides containing CpG motifs (CpG-ODN) predominantly induce Th1-type immune response in neonatal chicks. Dev Comp Immunol 32:1041-1049. 2008.
25. Gomis, S., L. Babiuk, B. Allan, P. Willson, E. Waters, N. Ambrose, R. Hecker, and A. Potter. Protection of neonatal chicks against a lethal challenge of *Escherichia coli* using DNA containing cytosine-phosphodiester-guanine motifs. Avian diseases 48:813-822. 2004.
26. Taghavi, A., B. Allan, G. Mutwiri, A. Van Kessel, P. Willson, L. Babiuk, A. Potter, and S. Gomis. Protection of neonatal broiler chicks against *Salmonella Typhimurium* septicemia by DNA containing CpG motifs. Avian diseases 52:398-406. 2008.
27. T. Gunawardana, M. Foldvari, T. Zachar, S. Popowich, B. Chow-Lockerbie, M. V. Ivanova, S. Tikoo, S. Kurukulasuriya, P. Willson, S. Gomis, Protection of neonatal broiler chickens following in ovo delivery of oligodeoxynucleotides containing CpG motifs (CpG-ODN) formulated with carbon nanotubes or liposomes, Avian diseases, 59 (2015) 31-37.
28. S. Gomis, L. Babiuk, B. Allan, P. Willson, E. Waters, N. Ambrose, R. Hecker, A. Potter, Protection of neonatal chicks against a lethal challenge of *Escherichia coli* using DNA containing cytosine-phosphodiester-guanine motifs, Avian diseases, 48 (2004) 813-822.
29. J. T. van Oirschot, Present and future of veterinary viral vaccinology: a review, The Veterinary quarterly, 23 (2001) 100-108.
30. M. B. Dolovich, R. Dhand, Aerosol drug delivery: developments in device design and clinical use, 2011 The Lancet, 377 1032-1045.
31. A. Gautam, J. Clifford Waldrep, C. L. Densmore, Aerosol gene therapy, Molecular Biotechnology, 23 (2003) 51-60.
32. T. Gunawardana, M. Foldvari, T. Zachar, S. Popowich, B. Chow-Lockerbie, M. V. Ivanova, S. Tikoo, S. Kurukulasuriya, P. Willson, S. Gomis, Protection of neonatal broiler chickens following in ovo delivery of oligodeoxynucleotides containing CpG motifs (CpG-ODN) formulated with carbon nanotubes or liposomes, Avian diseases, 59 (2015) 31-37.
33. G. d. Lange, Spray vaccination of day-old-chicks at the hatchery, in, Pas Reform Integrated hatchery solutions, Pas Reform Integrated hatchery solutions.
34. B. Peeters, W. F. Tonnis, S. Murugappan, P. Rottier, G. Koch, H. W. Frijlink, A. Huckriede, W. L. J. Hinrichs, Pulmonary immunization of chickens using non-adjuvanted spray-freeze dried whole inactivated virus vaccine completely protects against highly pathogenic H5N1 avian influenza virus, Vaccine, 32 (2014) 6445-6450.
35. M. J. Rathbone, M. N. Martinez, Modified release drug delivery in veterinary medicine, Drug Discovery Today, 7 (2002) 823-829.
36. F. Andrade, D. Rafael, M. Videira, D. Ferreira, A. Sosnik, B. Sarmento, Nanotechnology and pulmonary delivery to overcome resistance in infectious diseases, Advanced Drug Delivery Reviews, 65 (2013) 1816-1827.
37. M. D. I. Manunta, R. J. McAnulty, A. McDowell, J. Jin, D. Ridout, J. Fleming, S.E-*---. Bottoms, L. Tossici-Bolt, G. J. Laurent, L. Biassoni, C. O'Callaghan, S. L. Hart, Airway deposition of nebulized gene delivery nanocomplexes monitored by radioimaging agents, American Journal of Respiratory Cell and Molecular Biology, 49 (2013) 471-480.
38. J. McCaskill, R. Singhania, M. Burgess, R. Allavena, S. Wu, A. Blumenthal, N. A. J. McMillan, Efficient biodistribution and gene silencing in the lung epithelium via intravenous liposomal delivery of siRNA, Molecular Therapy Nucleic Acids, 2 (2013) e96.
39. G. Shim, H.-w. Choi, S. Lee, J. Choi, Y. H. Yu, D.-E. Park, Y. Choi, C.-W. Kim, Y.-K. Oh, Enhanced Intrapulmonary Delivery of Anticancer siRNA for Lung Cancer Therapy Using Cationic Ethylphosphocholine-based Nanolipoplexes, Molecular Therapy, 21 (2013) 816-824.
40. C. Sawaengsak, Y. Mori, K. Yamanishi, P. Srimanote, W. Chaicumpa, A. Mitrevej, N. Sinchaipanid, Intranasal chitosan-DNA vaccines that protect across influenza virus subtypes, International Journal of Pharmaceutics, 473 (2014) 113-125.
41. J. S. Suk, A. J. Kim, K. Trehan, C. S. Schneider, L. Cebotaru, O. M. Woodward, N. J. Boylan, M. P. Boyle, S. K. Lai, W. B. Guggino, J. Hanes, Lung gene therapy with highly compacted DNA nanoparticles that overcome the mucus barrier, Journal of Controlled Release, 178 (2014) 8-17.
42. M. Bivas-Benita, K. E. van Meijgaarden, K. L. M. C. Franken, H. E. Junginger, G. Borchard, T. H. M. Ottenhoff, A. Geluk, Pulmonary delivery of chitosan-DNA nanoparticles enhances the immunogenicity of a DNA vaccine encoding HLA-A*0201-restricted T-cell epitopes of *Mycobacterium tuberculosis*, Vaccine, 22 (2004) 1609-1615.

43. J. F. S. Mann, P. F. McKay, S. Arokiasamy, R. K. Patel, K. Klein, R. J. Shattock, Pulmonary delivery of DNA vaccine constructs using deacylated PEI elicits immune responses and protects against viral challenge infection, Journal of Controlled Release, 170 (2013) 452-459.
44. V. Weissig, T. K. Pettinger, N. Murdock, Nanopharmaceuticals (part 1): products on the market, International Journal of Nanomedicine, 9 (2014) 4357-4373.
45. V. Gerdts, G. K. Mutwiri, S. K. Tikoo, L. A. Babiuk, Mucosal delivery of vaccines in domestic animals, Veterinary research, 37 (2006) 487-510.
46. A. Taghavi, B. Allan, G. Mutwiri, M. Foldvari, A. Van Kessel, P. Willson, L. Babiuk, A. Potter, S. Gomis, Enhancement of immunoprotective effect of CpG-ODN by formulation with polyphosphazenes against *E. coli* septicemia in neonatal chickens, Current drug delivery, 6 (2009) 76-82.
47. F. Mansoor, B. Earley, J. P. Cassidy, B. Markey, S. Doherty, M.D. Welsh, Comparing the immune response to a novel intranasal nanoparticle PLGA vaccine and a commercial BPI3V vaccine in dairy calves, BMC Veterinary Research, 11 (2015) 220.
48. A. K. Panda, Nanotechnology in vaccine development, Proceedings of the National Academy of Sciences, India Section B: Biological Sciences, 82 (2012) 13-27.
49. M.-G. Kim, J. Y. Park, Y. Shon, G. Kim, G. Shim, Y.-K. Oh, Nanotechnology and vaccine development, Asian Journal of Pharmaceutical Sciences, 9 (2014) 227-235.
50. A. Nasir, Nanotechnology in vaccine development: a step forward, Journal of Investigative Dermatology, 129 (2009) 1055-1059.
51. H. Shirota, D. M. Klinman, Recent progress concerning CpG DNA and its use as a vaccine adjuvant, Expert review of vaccines, 13 (2014) 299-312.
52. T. Negash, M. Liman, S. Rautenschlein, Mucosal application of cationic poly(D,L-lactide-co-glycolide) microparticles as carriers of DNA vaccine and adjuvants to protect chickens against infectious bursal disease, Vaccine, 31 (2013) 3656-3662.
53. M. Günbeyaz, A. Faraji, A. Özkul, N. Purli, S. Senel, Chitosan based delivery systems for mucosal immunization against bovine herpesvirus 1 (BHV-1), European Journal of Pharmaceutical Sciences, 41 (2010) 531-545.
54. E. N. T. Meeusen, J. Walker, A. Peters, P.-P. Pastoret, G. Jungersen, Current status of veterinary vaccines, Clinical Microbiology Reviews, 20 (2007) 489-510.
55. C.-J. Chiou, L.-P. Tseng, M.-C. Deng, P.-R. Jiang, S.-L. Tasi, T.-W. Chung, Y.-Y. Huang, D.-Z. Liu, Mucoadhesive liposomes for intranasal immunization with an avian influenza virus vaccine in chickens, Biomaterials, 30 (2009) 5862-5868.
56. M. A. Volkova, A. V. Irza, I. A. Chvala, S. F. Frolov, V. V. Drygin, D. R. Kapczynski, Adjuvant effects of chitosan and calcium phosphate particles in an inactivated Newcastle disease vaccine, Avian diseases, 58 (2014) 46-52.
57. L.-P. Tseng, C.-J. Chiou, C.-C. Chen, M.-C. Deng, T.-W. Chung, Y.-Y. Huang, D.-Z. Liu, Effect of lipopolysaccharide on intranasal administration of liposomal Newcastle disease virus vaccine to SPF chickens, Veterinary Immunology and Immunopathology, 131 (2009) 285-289.
58. K. Yaguchi, T. Ohgitani, T. Noro, T. Kaneshige, Y. Shimizu, Vaccination of chickens with liposomal inactivated avian pathogenic *Escherichia coli* (APEC) vaccine by eye drop or coarse spray administration, Avian diseases, 53 (2009) 245-249.
59. A. Taghavi, B. Allan, G. Mutwiri, A. Van Kessel, P. Willson, L. Babiuk, A. Potter, S. Gomis, Protection of neonatal broiler chicks against *Salmonella Typhimurium* septicemia by DNA containing CpG motifs, Avian diseases, 52 (2008) 398-406.
60. K. M. Mackinnon, H. He, C. L. Swaggerty, J. L. McReynolds, K. J. Genovese, S. E. Duke, J. R. Nerren, M. H. Kogut, In ovo treatment with CpG oligodeoxynucleotides decreases colonization of *Salmonella enteriditis* in broiler chickens, Veterinary Immunology and Immunopathology, 127 (2009) 371-375.
61. S. Gomis, L. Babiuk, D. L. Godson, B. Allan, T. Thrush, H. Townsend, P. Willson, E. Waters, R. Hecker, A. Potter, Protection of chickens against *Escherichia coli* infections by DNA containing CpG motifs, Infection and Immunity, 71 (2003) 857-863.
62. R. B. Hayter, E. L. Besch, Airborne-particle deposition in the respiratory tract of chickens, Poultry science, 53 (1974) 1507-1511.
63. E. A. Corbanie, M. G. Matthijs, J. H. van Eck, J. P. Remon, W. J. Landman, C. Vervaet, Deposition of differently sized airborne microspheres in the respiratory tract of chickens, Avian Pathol, 35 (2006) 475-485.
64. M. Look, A. Bandyopadhyay, J. S. Blum, T. M. Fahmy, Application of nanotechnologies for improved immune response against infectious diseases in the developing world, Advanced Drug Delivery Reviews, 62 (2010) 378-393.
65. S. P. Kalhari Bandara Goonewardene, Thushari Gunwardana, Suresh Tikoo, Marianna Foldvari, Philip Willson, and Susantha Gomis, Immunoprotective effects against *Escherichia coli* septicemia in neonatal broiler chickens following intrapulmonary delivery of oligodeoxynucleotides containing CpG motifs (CpG-ODN) as micro-droplets (in preparation).
66. K. B. G. Daniella Calderon, Susantha Gomis, Shelly Popowich, Thushari Gunawardana, Suresh Tikoo, Marianna Foldvari, Poultry vaccine nanoparticle design for inhalation: intrapulmonary delivery of oligodeoxynucleotides containing CpG motifs (CpG-ODN) in lipid-based and polymeric nanoparticles (in preparation).
67. K. Goonewardene, S. Popowich, T. Gunwardana, A. Gupta, S. Kurukulasuriya, R. Karunarathna, B. Chow-Lockerbie, K. A. AHMED, S. K. Tikoo, M. Foldvari, P. Willson, S. Gomis, Intrapulmonary Delivery of CPG-ODN Micro-Droplets Provides Protection against *Escherichia Coli* Septicemia in Neonatal Broiler Chickens, Avian diseases, In Press.
68. H.-Q. Mao, K. Roy, V. L. Troung-Le, K. A. Janes, K. Y. Lin, Y. Wang, J. T. August, K. W. Leong, Chitosan-DNA nanoparticles as gene carriers: synthesis, characterization and transfection efficiency, Journal of Controlled Release, 70 (2001) 399-421.
69. T. Sato, T. Ishii, Y. Okahata, In vitro gene delivery mediated by chitosan. effect of pH, serum, and molecular mass of chitosan on the transfection efficiency, Biomaterials, 22 (2001) 2075-2080.
70. P. Erbacher, S. Zou, T. Bettinger, A. M. Steffan, J. S. Remy, Chitosan-based vector/DNA complexes for gene delivery: biophysical characteristics and transfection ability, Pharmaceutical Research, 15 (1998) 1332-1339.

71. M. Huang, E. Khor, L.-Y. Lim, Uptake and cytotoxicity of chitosan molecules and nanoparticles: effects of molecular weight and degree of deacetylation, Pharmaceutical Research, 21 (2004) 344-353.
72. S. Mao, W. Sun, T. Kissel, Chitosan-based formulations for delivery of DNA and siRNA, Advanced Drug Delivery Reviews, 62 (2010) 12-27.
73. M. Koping-Hoggard, I. Tubulekas, H. Guan, K. Edwards, M. Nilsson, K. M. Varum, P. Artursson, Chitosan as a nonviral gene delivery system. Structure-property relationships and characteristics compared with polyethylenimine in vitro and after lung administration in vivo, The Journal of Gene Therapy, 8 (2001) 1108-1121.

The invention claimed is:

1. A composition comprising one or more CpG oligodeoxynucleotide(s) (CpG-ODN) complexed with nanoparticles comprising a gemini surfactant and a mucoadhesive polymer formulated for intrapulmonary use, wherein the one or more CpG-ODN is a class B CpG ODN, and the muco-adhesive polymer is selected from polyvinylpyrrolidone (PVP) carboxy methylcellulose (CMC), optionally sodium CMC (CMCNa), and combinations thereof.

2. The composition of claim 1, wherein the composition is a micro-droplet composition or nebulized composition.

3. The composition of claim 1, wherein the composition further comprises a lipid.

4. The composition of claim 1, wherein the CpG-ODN is CpG 2007.

5. The composition of claim 1, wherein the gemini surfactant has one or more of a hydrocarbon tail that is 12 to 18 carbons in length, a spacer 3 to 7 carbons in length.

6. The composition of claim 1, wherein the muco-adhesive polymer is comprised in, complexed with or in the nanoparticle.

7. The composition of claim 1, wherein the composition further comprises PEG and a phospholipid.

8. The composition of claim 7, wherein the PEG is selected from PEG 400, polyethylene glycol monomethyl ether (mPEG), and propylene glycol (PG) and combinations thereof; and the phospholipid is selected from phosphatidylcholine, preferably 1,2-Dipalmitoyl-sn-glycero-3-phosphocholine (DPPC); soybean phosphatidylcholine, egg phosphatidylcholine and/or hydrogenated phosphatidylcholine, and phosphotidylethanolamine and/or wherein the phospholipid is PEGylated.

9. The composition of claim 3, wherein, the gemini surfactant is Gemini 12-3-12 and the composition comprises phosphatidylcholine (PC); or wherein the nanoparticles comprise Gemini 12-3-12, CMCNa, PEG, and DPPC; Gemini 12-3-12, CMCNa, PEG 400, and DPPC or Gemini 12-3-12, PVP MW 10,000, PEG 400 and DPPC.

10. The composition of claim 8, wherein the amount of DPPC in a formulation is about 0.1% to 20% (m/v) of total volume of the final composition.

11. The composition of claim 1, wherein one or more of the amount of gemini surfactant used in the formulation is about 0.01% to 5% (m/v) of the total volume of the final composition; wherein the composition further comprises an excipient selected from PG or PEG and the amount of excipient is about 1% to 20% (m/v) of the total volume of the final composition; and the muco-adhesive polymer is selected from PVP MW 40,000, PVP MW 10,000 and CMCNa and the amount of muco-adhesive polymer used in the formulation is about 0.1% to 20% (m/v) of the total volume of the final composition.

12. The composition of claim 1, wherein the composition is formulated for a dosage comprising at least 25 μg up to about 500 μg of CpG-ODN, or at least 100 μg of CPG-ODN and/or comprises sufficient CpG-ODNs for about 500 to 5000 doses.

13. The composition of claim 1, wherein the composition further comprises an antigen, and wherein the composition has an average polydispersity index (PD) of less than 0.5, and/or has an average zeta potential of at least 32MV or wherein the composition is formulated for needle free intrapulmonary delivery.

14. A method for stimulating immunity in a feed animal, comprising administering to the feed animal by intrapulmonary delivery an effective amount of micro-droplets of a composition comprising one or more CpG-ODNs, wherein the composition is the composition of claim 1.

15. The method of claim 14, wherein one or more of: the composition is administered by natural inspiration, the feed animal is exposed to the composition for at least about 10 min, at least about 15 min, at least about 20 min, at least about 25 min, at least about 30 min, or at least about 35 min; and the administration is repeated.

16. The method of claim 14, wherein the feed animal is a turkey, layer hen or a broiler chicken.

17. The method of claim 14, wherein the feed animal is administered about 1 mg to about 4 mg of CpG-ODN/0.036 $m^3$ of chamber, or wherein the feed animal is administered about 25 μg to about 500 μg of CpG-ODN.

18. The method of claim 14 wherein the feed animal is administered the composition in chamber where the average temperature is about 22° C. to about 24° C.

19. The composition of claim 3, wherein the lipid is DPPC, the gemini surfactant is gemini 12-3-12, the CpG-ODN, comprises a sequence of SEQ ID NO: 1, and the composition further comprises an excipient, said excipient being propylene glycol.

20. The composition of claim 1, wherein the ratio of gemini surfactant to CpG-ODN is between 1.5:1 to 3:1.

* * * * *

UNITED STATES PATENT AND TRADEMARK OFFICE

CERTIFICATE OF CORRECTION

PATENT NO. : 11,839,652 B2
APPLICATION NO. : 16/630744
DATED : December 12, 2023
INVENTOR(S) : Susantha Gomis et al.

It is certified that error appears in the above-identified patent and that said Letters Patent is hereby corrected as shown below:

In the Claims

Column 57, Lines 2-9, should read:
1. A composition comprising one or more CpG oligodeoxynucleotide(s) (CpG-ODN) complexed with nanoparticles comprising a gemini surfactant and a mucoadhesive polymer formulated for intrapulmonary use, wherein the one or more CpG-ODN is a class B CpG ODN, and the muco-adhesive polymer is selected from polyvinylpyrrolidone (PVP), carboxy methylcellulose (CMC), optionally sodium CMC (CMCNa), and combinations thereof.

Signed and Sealed this
First Day of April, 2025

Coke Morgan Stewart
*Acting Director of the United States Patent and Trademark Office*

SEQUENCE LISTING

```
<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: Synthetic construct

<400> SEQUENCE: 1

tcgtcgttgt cgtt                                                    14


<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2

tcgtcgttgt cgttttgtcg tt                                           22


<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3

tcgtcgtttt gtcgttttgt cgtt                                         24


<210> SEQ ID NO 4
<211> LENGTH: 27
<212> TYPE: DNA
<213> ORGANISM: Artificial Sequence
<220> FEATURE:
<223> OTHER INFORMATION: Synthetic construct

<400> SEQUENCE: 4

tcgcgtgcgt tttgtcgttt tgacgtt                                      27


<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5

tcgtcgtttg tcgttttgtc gtt                                          23


<210> SEQ ID NO 6
<211> LENGTH: 54
<212> TYPE: DNA
<213> ORGANISM: Artificial Sequence
<220> FEATURE:
<223> OTHER INFORMATION: Synthetic construct
<220> FEATURE:
```

<221> NAME/KEY: misc_feature
<222> LOCATION: (1)..(25)
<223> OTHER INFORMATION: n is any nucleotide and is either present or
absent
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(54)
<223> OTHER INFORMATION: n is a, c, g, or t

<400> SEQUENCE: 6
nnnnnnnnnn nnnnnnnnnn nnnnnncgnn nnnnnnnnnn nnnnnnnnnn nnnn 54

<210> SEQ ID NO 7
<211> LENGTH: 55
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(25)
<223> OTHER INFORMATION: n is any nucleotide and is either present or
absent
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(55)
<223> OTHER INFORMATION: n is any nucleotide and is either present or
absent

<400> SEQUENCE: 7
nnnnnnnnnn nnnnnnnnnn nnnnnncgnn nnnnnnnnnn nnnnnnnnnn nnnnn 55

<210> SEQ ID NO 8
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(25)
<223> OTHER INFORMATION: n is any nucleotide and is either present or
absent
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 8
tcnnnnnnnn nnnnnnnnnn nnnnnnntnn cgnn 34